United States Patent
Collins et al.

(10) Patent No.: US 11,753,664 B2
(45) Date of Patent: Sep. 12, 2023

(54) ENZYMATIC TREATMENT OF ANTHOCYANINS

(71) Applicants: MARS, INCORPORATED, McLean, VA (US); THE REGENTS OF THE UNIVERSITY OF CALIFORNIA, Oakland, CA (US)

(72) Inventors: Thomas M. Collins, Chicago, IL (US); Rebecca J. Robbins, Chicago, IL (US); Randall Powers, Chicago, IL (US); Justin Siegel, Oakland, CA (US); Pamela Ruth Denish, Oakland, CA (US); Kathryn Gwendolyn Guggenheim, Oakland, CA (US)

(73) Assignees: MARS, INCORPORATED, McLean, VA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/711,259

(22) Filed: Apr. 1, 2022

(65) Prior Publication Data
US 2022/0340941 A1  Oct. 27, 2022

Related U.S. Application Data

(63) Continuation of application No. PCT/US2020/053849, filed on Oct. 1, 2020.

(60) Provisional application No. 62/909,106, filed on Oct. 1, 2019.

(51) Int. Cl.
| | |
|---|---|
| *C12P 19/60* | (2006.01) |
| *C12P 17/16* | (2006.01) |
| *A23L 5/43* | (2016.01) |
| *C12N 9/18* | (2006.01) |

(52) U.S. Cl.
CPC .............. *C12P 17/162* (2013.01); *A23L 5/43* (2016.08); *C12N 9/18* (2013.01); *C12P 19/60* (2013.01); *C12Y 301/01001* (2013.01); *A23V 2002/00* (2013.01)

(58) Field of Classification Search
CPC ....................................................... C12N 9/18
See application file for complete search history.

(56) References Cited

U.S. PATENT DOCUMENTS

| | | |
|---|---|---|
| 2012/0034658 A1 | 2/2012 | Yoon |
| 2013/0165531 A1 | 6/2013 | Shi |
| 2015/0208705 A1 | 7/2015 | Galaffu |
| 2015/0374009 A1 | 12/2015 | Robbins |
| 2016/0015067 A1 | 1/2016 | Robbins et al. |
| 2017/0000169 A1* | 1/2017 | Robbins .................. C09B 61/00 |
| 2017/0086486 A1 | 3/2017 | Myers et al. |

FOREIGN PATENT DOCUMENTS

| | | |
|---|---|---|
| CN | 104640461 A | 5/2015 |
| EA | 025212 B1 | 11/2016 |
| JP | S63110259 A | 5/1988 |
| JP | S63243167 A | 10/1988 |
| RU | 2025475 C1 | 12/1994 |
| RU | 2202575 C1 | 4/2003 |
| RU | 2302423 C2 | 7/2007 |
| WO | 2009005647 A2 | 1/2009 |
| WO | WO 2009/005647 A2 | 1/2009 |
| WO | 2010114568 A1 | 10/2010 |
| WO | WO 2010/114568 A1 | 10/2010 |
| WO | 2012172429 A2 | 12/2012 |
| WO | WO 2012/172429 A2 | 12/2012 |
| WO | 2014023712 A1 | 2/2014 |
| WO | WO 2014/023712 A1 | 2/2014 |
| WO | 2014150230 A1 | 9/2014 |
| WO | 2014150438 A1 | 9/2014 |
| WO | 2014152417 A2 | 9/2014 |
| WO | WO 2014/150438 A1 | 9/2014 |
| WO | WO 2014/152417 A2 | 9/2014 |
| WO | 2017004452 A1 | 1/2017 |
| WO | WO 2017/004452 A1 | 1/2017 |
| WO | 2020047276 A1 | 3/2020 |
| WO | WO 2020/047276 A1 | 3/2020 |

OTHER PUBLICATIONS

Ahmadiani et al., Molar Absorptivity (ε) and Spectral Characteristics of Cyanidin-Based Anthocyanins from Red Cabbage, Molar Absorptivity (ε) and Spectral Characteristics of Cyanidin-Based Anthocyanins from Red Cabbage, Apr. 15, 2016, 8 pgs, 197, Food Chemistry.

Kleffner et al., Foldit Standalone: a video game-derived protein structure manipulation interface using Rosetta. Bioinformatics. Sep. 1, 2017;33(17):2765-2767.

Kunkel, Thomas A. "Rapid and efficient site-specific mutagenesis without phenotypic selection." Proceedings of the National Academy of Sciences 82.2 (Jan. 1, 1985): 488-492.

Meiler et al., ROSETTALIGAND: Protein-small molecule docking with full side-chain flexibility, Proteins: Structure 65 (2006): Abstract—3pgs.

Potter, Simon C et al. "HMMER web server: 2018 update." Nucleic acids research vol. 46,W1 (2018): W200-W204. doi:10.1093/nar/gky448, 10 pgs.

(Continued)

*Primary Examiner* — Tekchand Saidha
(74) *Attorney, Agent, or Firm* — Baker Botts L.L.P.

(57) ABSTRACT

Methods for converting mixtures of anthocyanins occurring in fruit or vegetable juice or extract into particular anthocyanin molecules having desirable colorant properties are provided herein. The method of the present disclosure can be employed to increase the amount of particular anthocyanin molecules, while lowering the total number of anthocyanin molecules present in the natural juice and/or extract. The disclosure is also directed to anthocyanin molecules prepared by the methods of present disclosure and to enzymes capable of catalyzing reactions that provide such effects.

9 Claims, 4 Drawing Sheets
Specification includes a Sequence Listing.

(56) References Cited

OTHER PUBLICATIONS

Sigurdson et al., Evaluating the role of metal ions in the bathochromic and hyperchromic responses of cyanidin derivatives in acidic and alkaline pH, Food Chemistry, Mar. 29, 2016, pp. 26-34, vol. 208, Food Chemistry, Elsevier Ltd.
International Search Report and Written Opinion dated Jan. 15, 2021 in International Application No. PCT/US2020/053849, 16 pages.
Ahmadiani et al., Solid phase fractionation techniques for segregation of red cabbage anthocyanins with different colorimetric and stability properties, Food Research International, vol. 120, Jun. 2019, pp. 688-696.
Sigurdson et al., Spectral and colorimetric characteristics of metal chelates of acylated cyanidin derivatives, Food Chemistry, Elsevier Ltd, NL, vol. 221(2017), Nov. 11, 2016, pp. 1088-1095.
Uniprot: Q1QYJ5, May 16, 2006, Subname: Full=Carboxylesterase [ECO:0000313|EMBL:ABE58463.1]; ED=3.1.1.1 [ECO:0000313|EMBL:ABE58463.1], 5Pgs.
Database UniProt [Online] May 16, 2006(May 16, 2006), "SubName:Full=Carboxylesterase {ECO:00003131eMBL:ABE58463.1}; EC=3.1.1.1 {ECO:00003131EMBL:ABE5 8463.1};", XP002801507, retrieved from EBI accession No. UNIPROT:Q1QYJ5.
Ahmadiani et al., "Molar absorptivity ([epsilon]) and spectral characteristics of cyanidin-based anthocyanins from red cabbage," Food Chemistry, 191, 900-906 (2016).
Ahmadiani et al., "Solid phase fractionation techniques for segregation of red cabbage anthocyanins with different colorimetric and stabiliity properties," Food Research International, 120, 688-696 (2019).
International Search Report dated Jan. 15, 2021 in International Application No. PCT/US2020/0053849.
Kleffner et al., "Foldit Standalone: a video game-derived protein structure manipulation interface using Rosetta," Bioinformatics, 33(17): 2765-2767 (2017).
Kunkel, "Rapid and efficient site-specific mutagenesis without phenotypic selection," Proceedings of the National Academy of Sciences, 82, 488-492 (1985).
Meiler et al., "ROSETTALIGAND: Protein-small molecule docking with full side-chain flexibility," Proteins: Structure, Function, and Bioinformatics, 65, 538-548 (2006).
Potter et al., "HMMER web server: 2018 update," Nucleic Acids Research. 46, W200-W204 (2018).
Sigurdson et al., "Spectral and colorimetric characteristics of metal chelates of acylated cyanidin derivatives", Food Chemistry, 221, 1088-1095 (2017).
Sigurdson et al., "Evaluating the role of metal ions in the bathochromic and hyperchromic responses of cyanidin derivative in acidic and alkaline pH", Food Chemistry, 208, 29-34 (2016).
Denish P. R. et al., Science Advances Research Article, Discovery of a natural cyan blue: A unique food-sourced anthocyanin could replace synthetic brilliant blue, Apr. 7, 2021, p. 1-9, ., Retrieved from the Internet, URL:https://www.science.org/doi/epdf/10.11 26/sciadv.abe7871, EP.

* cited by examiner

SEQUENCE LISTING

```
<160> NUMBER OF SEQ ID NOS: 91

<210> SEQ ID NO 1
<211> LENGTH: 225
<212> TYPE: PRT
<213> ORGANISM: Chromohalobacter salexigens

<400> SEQUENCE: 1

Met Ala Asp Ser Ser Pro Leu Ile Ile Glu Pro Arg Gln Ala Arg Ala
1               5                   10                  15

Ala Asp Ala Thr Val Ile Leu Leu His Gly Leu Gly Ala Asp Gly His
                20                  25                  30

Asp Phe Glu Pro Leu Val Pro Ala Leu Pro Leu Ala Lys Asp Leu Ala
            35                  40                  45

Val Arg Phe Val Leu Pro His Ala Pro Arg Met Pro Val Thr Val Asn
        50                  55                  60

Gly Gly Met Glu Met Pro Ala Trp Tyr Asp Ile Leu Asp Met Asn Leu
65                  70                  75                  80

Gly Arg Arg Ile Asp Glu Ala Gln Leu Lys Ala Ser Ala Asp Met Val
                85                  90                  95

His Gly Leu Ile Asp Ala Glu Ile Ala Arg Gly Ile Asp Ser Arg Arg
            100                 105                 110

Ile Ile Val Ala Gly Phe Ser Gln Gly Gly Ala Val Ala Tyr His Ala
        115                 120                 125

Ala Leu Thr Tyr Pro Lys Pro Leu Gly Gly Leu Leu Ala Leu Ser Thr
    130                 135                 140

Tyr Phe Ala Thr Ala Thr Ser Ile Glu Pro Ser Glu Ala Asn Arg Ala
145                 150                 155                 160

Leu Pro Ile Glu Val His His Gly Ser Phe Asp Pro Val Val Pro Glu
                165                 170                 175

Ala Leu Gly His Glu Gly Ala Glu Arg Ala Glu Ala Leu Gly Tyr Ala
            180                 185                 190

Val Thr Tyr Arg Thr Tyr Pro Met Gln His Ala Leu Cys Pro Glu Gln
        195                 200                 205

Ile Glu Asp Ile Gly Gln Trp Leu Asn Ala Arg Leu Gly Ala Lys Glu
    210                 215                 220

Ala
225

<210> SEQ ID NO 2
<211> LENGTH: 218
```

```
<212> TYPE: PRT
<213> ORGANISM: Pseudomonas fluorescens

<400> SEQUENCE: 2

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
                20                  25                  30

Val Ala Glu Ala Leu Gln Glu Ser Leu Leu Thr Thr Arg Phe Val Leu
            35                  40                  45

Pro Gln Ala Pro Thr Arg Pro Val Thr Ile Asn Gly Gly Tyr Glu Met
        50                  55                  60

Pro Ser Trp Tyr Asp Ile Lys Ala Met Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Ile His Asp
        195                 200                 205

Ile Gly Ala Trp Leu Ala Ala Arg Leu Gly
    210                 215

<210> SEQ ID NO 3
<211> LENGTH: 218
<212> TYPE: PRT
<213> ORGANISM: Pseudomonas aeruginosa

<400> SEQUENCE: 3

Met Ser Glu Pro Leu Ile Leu Asp Ala Pro Asn Ala Asp Ala Cys Ile
1               5                   10                  15

Ile Trp Leu His Gly Leu Gly Ala Asp Arg Thr Asp Phe Lys Pro Val
                20                  25                  30

Ala Glu Ala Leu Gln Met Val Leu Pro Ser Thr Arg Phe Ile Leu Pro
            35                  40                  45

Gln Ala Pro Ser Gln Ala Val Thr Val Asn Gly Gly Trp Val Met Pro
        50                  55                  60

Ser Trp Tyr Asp Ile Leu Ala Phe Ser Pro Ala Arg Ala Ile Asp Glu
65                  70                  75                  80

Asp Gln Leu Asn Ala Ser Ala Asp Gln Val Ile Ala Leu Ile Asp Glu
                85                  90                  95

Gln Arg Ala Lys Gly Ile Ala Ala Glu Arg Ile Ile Leu Ala Gly Phe
            100                 105                 110

Ser Gln Gly Gly Ala Val Val Leu His Thr Ala Phe Arg Arg Tyr Ala
        115                 120                 125
```

```
Gln Pro Leu Gly Gly Val Leu Ala Leu Ser Thr Tyr Ala Pro Thr Phe
    130                 135                 140

Asp Asp Leu Ala Leu Asp Glu Arg His Lys Arg Ile Pro Val Leu His
145                 150                 155                 160

Leu His Gly Ser Gln Asp Val Val Asp Pro Ala Leu Gly Arg Ala
            165                 170                 175

Ala His Asp Ala Leu Gln Ala Gln Gly Val Glu Val Gly Trp His Asp
            180                 185                 190

Tyr Pro Met Gly His Glu Val Ser Leu Glu Glu Ile His Asp Ile Gly
            195                 200                 205

Ala Trp Leu Arg Lys Arg Leu Gly Gly Ser
210                 215

<210> SEQ ID NO 4
<211> LENGTH: 309
<212> TYPE: PRT
<213> ORGANISM: Sulfolobus solfataricus

<400> SEQUENCE: 4

Met Pro Leu Asp Pro Glu Val Arg Asn Phe Leu Gln Val Tyr Tyr Lys
1               5                   10                  15

Ala Asn Ile Ile Asp Phe Thr Lys Tyr Gln Phe Gln Glu Ile Arg Gln
            20                  25                  30

Lys Val Asn Glu Leu Leu Ala Lys Ala Val Pro Lys Asp Pro Val Gly
        35                  40                  45

Glu Thr Arg Asp Met Lys Ile Lys Leu Glu Asp Tyr Glu Leu Pro Ile
    50                  55                  60

Arg Ile Tyr Ser Pro Ile Lys Arg Thr Asn Asn Gly Leu Val Met His
65                  70                  75                  80

Phe His Gly Gly Ala Trp Ile Leu Gly Ser Ile Glu Thr Glu Asp Ala
                85                  90                  95

Ile Ser Arg Ile Leu Ser Asn Ser Cys Glu Cys Thr Val Ile Ser Val
            100                 105                 110

Asp Tyr Arg Leu Ala Pro Glu Tyr Lys Phe Pro Thr Ala Val Tyr Asp
        115                 120                 125

Cys Phe Asn Ala Ile Val Trp Ala Arg Asp Asn Ala Gly Glu Leu Gly
130                 135                 140

Ile Asp Lys Asp Lys Ile Ala Thr Phe Gly Ile Ser Ala Gly Gly Asn
145                 150                 155                 160

Leu Val Ala Ala Thr Ser Leu Leu Ala Arg Asp Asn Lys Leu Lys Leu
                165                 170                 175

Thr Ala Gln Val Pro Val Val Pro Phe Val Tyr Leu Asp Leu Ala Ser
            180                 185                 190

Lys Ser Met Asn Arg Tyr Arg Lys Gly Tyr Phe Leu Asp Ile Asn Leu
        195                 200                 205

Pro Val Asp Tyr Gly Val Lys Met Tyr Ile Arg Asp Glu Lys Asp Leu
    210                 215                 220

Tyr Asn Pro Leu Phe Ser Pro Leu Ile Ala Glu Asp Leu Ser Asn Leu
225                 230                 235                 240

Pro Gln Ala Ile Val Val Thr Ala Glu Tyr Asp Pro Leu Arg Asp Gln
                245                 250                 255

Gly Glu Ala Tyr Ala Tyr Arg Leu Met Glu Ser Gly Val Pro Thr Leu
            260                 265                 270

Ser Phe Arg Val Asn Gly Asn Val His Ala Phe Leu Gly Ser Pro Arg
        275                 280                 285
```

```
Thr Ser Arg Gln Val Thr Val Met Ile Gly Ala Leu Leu Lys Asp Ile
    290                 295                 300

Phe Lys Gly Ser Ser
305
```

<210> SEQ ID NO 5
<211> LENGTH: 281
<212> TYPE: PRT
<213> ORGANISM: Aspergillus niger

<400> SEQUENCE: 5

```
Met Lys Gln Phe Ser Ala Lys Tyr Ala Leu Ile Leu Ala Thr Ala
1               5                   10                  15

Gly Gln Ala Leu Ala Ala Ser Thr Gln Gly Ile Ser Glu Asp Leu Tyr
            20                  25                  30

Asn Arg Leu Val Glu Met Ala Thr Ile Ser Gln Ala Ala Tyr Ala Asp
        35                  40                  45

Leu Cys Asn Ile Pro Ser Thr Ile Ile Lys Gly Glu Lys Ile Tyr Asn
    50                  55                  60

Ala Gln Thr Asp Ile Asn Gly Trp Ile Leu Arg Asp Asp Thr Ser Lys
65                  70                  75                  80

Glu Ile Ile Thr Val Phe Arg Gly Thr Gly Ser Asp Thr Asn Leu Gln
                85                  90                  95

Leu Asp Thr Asn Tyr Thr Leu Thr Pro Phe Asp Thr Leu Pro Gln Cys
            100                 105                 110

Asn Asp Cys Glu Val His Gly Gly Tyr Tyr Ile Gly Trp Ile Ser Val
        115                 120                 125

Gln Asp Gln Val Glu Ser Leu Val Lys Gln Gln Ala Ser Gln Tyr Pro
    130                 135                 140

Asp Tyr Ala Leu Thr Val Thr Gly His Ser Leu Gly Ala Ser Met Ala
145                 150                 155                 160

Ala Leu Thr Ala Ala Gln Leu Ser Ala Thr Tyr Asp Asn Val Arg Leu
                165                 170                 175

Tyr Thr Phe Gly Glu Pro Arg Ser Gly Asn Gln Ala Phe Ala Ser Tyr
            180                 185                 190

Met Asn Asp Ala Phe Gln Val Ser Ser Pro Glu Thr Thr Gln Tyr Phe
        195                 200                 205

Arg Val Thr His Ser Asn Asp Gly Ile Pro Asn Leu Pro Pro Ala Asp
    210                 215                 220

Glu Gly Tyr Ala His Gly Gly Val Glu Tyr Trp Ser Val Asp Pro Tyr
225                 230                 235                 240

Ser Ala Gln Asn Thr Phe Val Cys Thr Gly Asp Glu Val Gln Cys Cys
                245                 250                 255

Glu Ala Gln Gly Gly Gln Gly Val Asn Asp Ala His Thr Thr Tyr Phe
            260                 265                 270

Gly Met Thr Ser Gly Ala Cys Thr Trp
        275                 280
```

<210> SEQ ID NO 6
<211> LENGTH: 222
<212> TYPE: PRT
<213> ORGANISM: Francisella tularensis

<400> SEQUENCE: 6

```
Met Asn Tyr Glu Leu Met Glu Pro Ala Lys Gln Ala Arg Phe Cys Val
1               5                   10                  15
```

```
Ile Trp Leu His Gly Leu Gly Ala Asp Gly His Asp Phe Val Asp Ile
            20                  25                  30

Val Asn Tyr Phe Asp Val Ser Leu Asp Glu Ile Arg Phe Ile Phe Pro
        35                  40                  45

His Ala Asp Ile Ile Pro Val Thr Ile Asn Met Gly Met Gln Met Arg
 50                  55                  60

Ala Trp Tyr Asp Ile Lys Ser Leu Asp Ala Asn Ser Leu Asn Arg Val
 65                  70                  75                  80

Val Asp Val Glu Gly Ile Asn Ser Ser Ile Ala Lys Val Asn Lys Leu
                85                  90                  95

Ile Asp Ser Gln Val Asn Gln Gly Ile Ala Ser Glu Asn Ile Ile Leu
            100                 105                 110

Ala Gly Phe Ser Gln Gly Gly Ile Ile Ala Thr Tyr Thr Ala Ile Thr
        115                 120                 125

Ser Gln Arg Lys Leu Gly Gly Ile Met Ala Leu Ser Thr Tyr Leu Pro
130                 135                 140

Ala Trp Asp Asn Phe Lys Gly Lys Ile Thr Ser Ile Asn Lys Gly Leu
145                 150                 155                 160

Pro Ile Leu Val Cys His Gly Thr Asp Asp Gln Val Leu Pro Glu Val
                165                 170                 175

Leu Gly His Asp Leu Ser Asp Lys Leu Lys Val Ser Gly Phe Ala Asn
            180                 185                 190

Glu Tyr Lys His Tyr Val Gly Met Gln His Ser Val Cys Met Glu Glu
        195                 200                 205

Ile Lys Asp Ile Ser Asn Phe Ile Ala Lys Thr Phe Lys Ile
210                 215                 220

<210> SEQ ID NO 7
<211> LENGTH: 270
<212> TYPE: PRT
<213> ORGANISM: Unknown
<220> FEATURE:
<223> OTHER INFORMATION: Description of Unknown:
      Uncultured bacterium FLS12

<400> SEQUENCE: 7

Met Ala Leu Phe Gln Cys Asp Phe Phe Ser Asp Val Leu Gly Leu Ser
1               5                   10                  15

Thr Ser Met Thr Val Ile Leu Pro Gln Glu Thr Thr Gly Gln Ile Gly
            20                  25                  30

Met Ala Gly Gly Ser Glu Arg Arg Glu His Pro Thr Leu Phe Leu Leu
        35                  40                  45

His Gly Leu Ser Asp Asp His Thr Ile Trp Leu Arg Arg Thr Ser Ile
 50                  55                  60

Glu Arg Tyr Val Ala Glu Met Gly Leu Ala Val Val Met Pro Ala Val
 65                  70                  75                  80

His Arg Ser Phe Tyr Thr Asp Met Ala His Gly Leu Gln Tyr Trp Thr
                85                  90                  95

Phe Ile Ser Glu Glu Leu Pro Ala Leu Ala Arg Ser Phe Phe Pro Leu
            100                 105                 110

Ala Thr Ala Arg Glu Asp Thr Phe Val Ala Gly Leu Ser Met Gly Gly
        115                 120                 125

Tyr Gly Ala Leu Lys Leu Gly Met Arg His Pro Glu Arg Phe Ala Ala
130                 135                 140

Ala Ala Ser Leu Ser Gly Ala Leu Asp Ile Thr Phe Asp Pro Ala Glu
```

```
                145                 150                 155                 160
His Ile Ala Met Glu Asp Asp Val Trp Val Ala Glu Gln Arg Asn Ile
                165                 170                 175

Phe Gly Asp Leu Ala Ala Leu Pro Gly Ser Asp His Asp Leu Phe Ala
            180                 185                 190

Leu Ala Glu Arg Met Ala Gln Ser Asp Gly Pro Val Pro Lys Leu Tyr
        195                 200                 205

Gln Cys Cys Gly Thr Glu Asp Phe Leu Tyr Glu Asp Asn Val Arg Phe
    210                 215                 220

Arg Asp His Val Arg Gly Leu Gly Leu Asp Phe Met Tyr Glu Glu Ser
225                 230                 235                 240

Pro Gly Glu His Glu Trp Gly Tyr Trp Asp Ala Gln Ile Gln Arg Val
                245                 250                 255

Leu Ala Trp Leu Pro Leu Arg Pro Pro Gly Thr Ala Pro Ala
                260                 265                 270

<210> SEQ ID NO 8
<211> LENGTH: 219
<212> TYPE: PRT
<213> ORGANISM: Pelagibacterium halotolerans

<400> SEQUENCE: 8

Met Thr Glu Pro Val Lys Leu Ser Gly Pro Met Leu Pro Ala Val Ser
1               5                   10                  15

Gly Ala Ala Lys Ser Leu Val Val Leu Leu His Gly Tyr Gly Ser Asp
            20                  25                  30

Gly Arg Asp Leu Ile Ala Leu Gly Gln Phe Trp Arg Asp Ser Phe Pro
        35                  40                  45

Asp Thr Met Phe Val Ala Pro Asn Ala Pro His Val Cys Gly Gly Asn
    50                  55                  60

Pro Phe Gly Tyr Glu Trp Phe Pro Leu Asp Leu Glu Arg Asp Arg Thr
65                  70                  75                  80

Leu Ala Arg Leu Ala Gly Ala Glu Thr Ala His Pro Val Leu Asp Ala
                85                  90                  95

Phe Leu Ala Asp Leu Trp Ala Gln Thr Gly Leu Gly Pro Ala Asp Thr
            100                 105                 110

Ile Leu Val Gly Phe Ser Gln Gly Ala Met Met Ala Leu Tyr Thr Gly
        115                 120                 125

Leu Arg Leu Pro Glu Pro Leu Lys Ala Ile Ile Ala Phe Ser Gly Leu
    130                 135                 140

Ile Val Ala Pro Glu Lys Leu Glu Ala Glu Ile Ala Ser Lys Pro Pro
145                 150                 155                 160

Val Leu Leu Ile His Gly Asp Leu Asp Val Val Pro Val Ile Gly
                165                 170                 175

Ser Glu Thr Ala Leu Pro Lys Leu Ile Asp Leu Gly Ile Asp Ala Arg
            180                 185                 190

Leu His Ile Ser Gln Gly Ser Gly His Thr Ile Ala Gln Asp Gly Leu
        195                 200                 205

Asp Thr Ala Thr Ala Phe Leu Arg Glu Ile Leu
    210                 215

<210> SEQ ID NO 9
<211> LENGTH: 306
<212> TYPE: PRT
<213> ORGANISM: Sulfolobus islandicus
```

<400> SEQUENCE: 9

Met Met Pro Leu Asp Pro Arg Ile Lys Glu Leu Leu Glu Ser Gly Phe
1               5                   10                  15

Ile Val Pro Ile Gly Lys Ala Ser Val Asp Glu Val Arg Lys Ile Phe
            20                  25                  30

Arg Gln Leu Ala Ser Ala Ala Pro Lys Val Glu Val Gly Lys Val Glu
        35                  40                  45

Asp Ile Lys Ile Pro Gly Ser Glu Ala Asn Ile Asn Ala Arg Val Tyr
    50                  55                  60

Leu Pro Lys Ala Asn Gly Pro Tyr Gly Val Leu Ile Tyr Leu His Gly
65                  70                  75                  80

Gly Gly Phe Val Ile Gly Asp Val Glu Ser Tyr Asp Pro Leu Cys Arg
                85                  90                  95

Ala Ile Thr Asn Ala Cys Asn Cys Val Val Val Ser Val Asp Tyr Arg
            100                 105                 110

Leu Ala Pro Glu Tyr Lys Phe Pro Ser Ala Val Ile Asp Ser Phe Asp
        115                 120                 125

Ala Thr Asn Trp Val Tyr Asn Asn Leu Asp Lys Phe Asp Gly Lys Met
    130                 135                 140

Gly Val Ala Ile Ala Gly Asp Ser Ala Gly Gly Asn Leu Ala Ala Val
145                 150                 155                 160

Val Ala Leu Leu Ser Lys Gly Lys Leu Asn Leu Lys Tyr Gln Ile Leu
                165                 170                 175

Ile Tyr Pro Ala Val Gly Phe Asp Ser Val Ser Arg Ser Met Ile Glu
            180                 185                 190

Tyr Ser Asp Gly Phe Phe Leu Thr Arg Glu His Ile Glu Trp Phe Gly
        195                 200                 205

Ser Gln Tyr Leu Arg Ser Pro Ala Asp Leu Leu Asp Phe Arg Phe Ser
    210                 215                 220

Pro Ile Leu Ala Gln Asp Leu Ser Gly Leu Pro Pro Ala Leu Ile Ile
225                 230                 235                 240

Thr Ala Glu Tyr Asp Pro Leu Arg Asp Gln Gly Glu Ala Tyr Ala Asn
                245                 250                 255

Arg Leu Leu Gln Ala Gly Val Pro Val Thr Ser Val Arg Phe Asn Asn
            260                 265                 270

Val Ile His Gly Phe Leu Ser Phe Pro Leu Ile Glu Gln Gly Arg
        275                 280                 285

Asp Ala Ile Ser Leu Ile Gly Ser Val Leu Arg Arg Thr Phe Tyr Asp
    290                 295                 300

Lys Ser
305

<210> SEQ ID NO 10
<211> LENGTH: 221
<212> TYPE: PRT
<213> ORGANISM: Halomonas sp.

<400> SEQUENCE: 10

Met Thr Ala Pro Gly Glu Leu Ile Ile Glu Pro Lys Asp Gly Gln Pro
1               5                   10                  15

Ala Asp Ala Cys Val Phe Ile Ile His Gly Leu Gly Ala Asp Gly His
            20                  25                  30

Asp Phe Glu Pro Leu Val Pro Ala Leu Ala Leu Pro Lys Asp Ser Arg
        35                  40                  45

```
Val Arg Phe Ile Met Pro His Ala Pro Arg Leu Pro Val Thr Ile Asn
 50                  55                  60

Gly Gly Met Val Met Pro Ala Trp Tyr Asp Ile Leu Ala Met Asp Leu
 65                  70                  75                  80

Gly Arg Arg Val Asp Glu Arg Gln Leu Lys Gln Ser Ala Glu Arg Ile
                 85                  90                  95

Gln Ala Leu Ile Gln Glu Gln Ile Asp Gln Gly Ile Asp Ser Gln Arg
            100                 105                 110

Ile Ile Val Ala Gly Phe Ser Gln Gly Gly Ala Val Ala Tyr His Ala
        115                 120                 125

Ala Leu Thr Phe Pro Ala Pro Leu Gly Gly Leu Leu Ala Met Ser Thr
130                 135                 140

Tyr Phe Ala Thr Ala Asp Asn Ile Asp Leu Ala Glu Ala Asn Arg Gln
145                 150                 155                 160

Ile Pro Ile Glu Val Gln His Gly Asn Phe Asp Pro Ile Val Pro Glu
                165                 170                 175

Ser Leu Gly Arg Ser Gly Ala Asp Arg Leu Lys Glu Met Gly Tyr Ala
            180                 185                 190

Val Asn Tyr Arg Gln Tyr Pro Met Ala His Ala Leu Cys Pro Gln Gln
        195                 200                 205

Val Asn Asp Ile Gly Lys Trp Leu Ser Ala Arg Leu Asn
210                 215                 220

<210> SEQ ID NO 11
<211> LENGTH: 219
<212> TYPE: PRT
<213> ORGANISM: Ignatzschineria indica

<400> SEQUENCE: 11

Met Asp Lys Pro Ile Ile Leu Asp Pro Lys Gln Ser Ala Asp Ser Ala
 1               5                  10                  15

Val Ile Trp Leu His Gly Leu Gly Ala Thr Lys Glu Asp Phe Leu Pro
            20                  25                  30

Val Ala Gln Ile Leu Gln Arg Asp Ala Leu Pro His Thr Arg Phe Ile
        35                  40                  45

Leu Pro Gln Ala Pro Val Arg Pro Val Thr Leu Asn Asn Gly Phe Pro
 50                  55                  60

Met Pro Ser Trp Tyr Asp Ile Ile Ala Leu Thr Ser Pro Arg Glu Ile
 65                  70                  75                  80

Lys Leu Ser Glu Leu Asp Glu Ser Ser Gln Ser Ile Ile Ala Leu Ile
                 85                  90                  95

Glu Ala Glu Ile Glu Lys Gly Ile Pro Leu Glu Arg Ile Ile Leu Ala
            100                 105                 110

Gly Phe Ser Gln Gly Gly Ala Val Val Leu His Thr Ala Phe Ile Ala
        115                 120                 125

Tyr Pro Lys Asn Val Gly Val Met Ala Leu Ser Thr Tyr Ser Ala
130                 135                 140

Thr Phe Asp Glu Ala Ile Thr Leu Asp Glu Lys Lys Gln Ile Pro
145                 150                 155                 160

Thr Leu His Leu His Gly Ser Leu Asp Pro Val Val Lys Ile Glu Leu
                165                 170                 175

Gly Arg Ala Ala Glu Gln Phe Leu Lys Ala Gln Gly Ile Asp Thr Arg
            180                 185                 190

Trp His Asp Tyr Pro Met Gln His Glu Val Ile Asn Asp Glu Leu Gln
        195                 200                 205
```

```
Asp Ile Ala Lys Trp Leu Ile Glu Arg Leu Gly
    210                 215

<210> SEQ ID NO 12
<211> LENGTH: 217
<212> TYPE: PRT
<213> ORGANISM: Pseudomonas citronellolis

<400> SEQUENCE: 12

Met Ser Gln Pro Leu Leu Glu Pro Thr Gln Pro Ala Asp Ser Cys
1               5                   10                  15

Val Ile Trp Leu His Gly Leu Gly Ala Asp Arg Tyr Asp Phe Glu Pro
                20                  25                  30

Val Ala Arg Met Leu Gln Lys Val Leu Pro Arg Thr Arg Phe Ile Leu
            35                  40                  45

Pro Gln Ala Pro Thr Arg Pro Val Thr Val Phe Asn Gly Met Pro Ala
    50                  55                  60

Pro Ser Trp Tyr Asp Ile Lys Ala Met Ala Pro Ala Arg Ala Ile Asp
65                  70                  75                  80

Glu Ala Gln Leu Asp Ala Ser Ala Asp Ala Val Ile Ala Leu Ile Glu
                85                  90                  95

Gly Gln Leu Ala Glu Gly Ile Ala Gln Arg Arg Ile Val Leu Ala Gly
            100                 105                 110

Phe Ser Gln Gly Gly Ala Val Val Leu His Thr Gly Tyr Leu Arg Trp
    115                 120                 125

Pro Gly Glu Leu Gly Gly Val Met Ala Leu Ser Thr Tyr Gly Pro Thr
130                 135                 140

Phe Asp Asp Asp Leu Gln Leu Pro Glu Ala Lys Lys Gln Gln Pro Ala
145                 150                 155                 160

Leu Cys Leu His Gly Thr Tyr Asp Asp Val Val Ala Pro Ala Met Gly
                165                 170                 175

Arg Ala Ala Tyr Asp Phe Leu Gln Arg Gln Gly Val Ala Val Gln Trp
            180                 185                 190

Arg Asp Tyr Pro Met Ala His Glu Val Ser Asn Gln Glu Ile Ala Asp
        195                 200                 205

Ile Ala Ala Trp Leu Arg Glu Arg Leu
    210                 215

<210> SEQ ID NO 13
<211> LENGTH: 486
<212> TYPE: PRT
<213> ORGANISM: Myxococcus fulvus

<400> SEQUENCE: 13

Met Asn Gly Leu Arg Trp Arg Leu Thr Gly Val Val Met Ala Trp Val
1               5                   10                  15

Leu Val Ala Pro Leu Ala Glu Ala Ala Asn Val Lys Gln Glu Val Asp
                20                  25                  30

Arg Tyr Ile Ser Gly Phe His Gln Lys Gly Leu Phe Asn Gly Thr Val
            35                  40                  45

Leu Val Ala Asn Glu Arg Gly Ile Leu Leu Lys Lys Gly Tyr Gly Ala
    50                  55                  60

Ala Asn Leu Glu Trp Lys Val Pro Asn Ala Pro Asp Thr Lys Phe Arg
65                  70                  75                  80

Ile Gly Ser Ile Thr Lys Ser Phe Thr Ala Thr Val Ile Leu Gln Leu
                85                  90                  95
```

Ala Ala Glu Gly Lys Leu Gln Leu Asp Asp Pro Ile Thr Lys His Leu
            100                 105                 110

Pro Asp Tyr Arg Lys Asp Thr Gly Asp Arg Val Thr Ile Thr His Leu
        115                 120                 125

Leu Asn His Thr Ser Gly Ile Pro Ser Tyr Thr Ser Lys Pro Ala Ile
    130                 135                 140

Met Lys Asp Ala Asp Gly Phe Glu Ser Val Ala Ala Phe Val Lys Lys
145                 150                 155                 160

Ala Cys Ser Asp Asp Leu Glu Phe Glu Pro Gly Thr Lys Tyr Ala Tyr
                165                 170                 175

Asn Asn Ser Gly Tyr Phe Leu Leu Gly Ala Ile Ile Glu Lys Leu Thr
            180                 185                 190

Gly Gln Thr Tyr Ala Glu Ala Val Gln Ala Arg Ile Leu Gly Pro Leu
        195                 200                 205

Gly Met Lys Asp Thr Gly Tyr Asp Val Ser Ala Thr Val Leu Pro Lys
    210                 215                 220

Arg Ala Ser Gly Tyr Ala Gln Ala Pro Gly Gly Ile Val Asn Ala Ala
225                 230                 235                 240

Trp Leu Asp Met Asn Leu Pro Tyr Ala Ala Gly Ser Leu Tyr Ser Thr
                245                 250                 255

Val Glu Asp Leu Tyr Arg Trp Glu Arg Ala Phe His Gly Asp Thr Leu
            260                 265                 270

Leu Pro Ala Ala Leu Lys Gln Lys Met Leu Thr Pro Gly Leu Ala His
        275                 280                 285

Tyr Gly Phe Gly Trp Val Met Ser Asp Met Thr Leu His Asp Gly Lys
    290                 295                 300

Thr Lys Leu Pro Gly Ile Phe His Thr Gly Gly Ile Asn Gly Phe Ser
305                 310                 315                 320

Ser Ile Leu Val Arg Val Pro Glu Arg Lys Glu Ala Val Ile Leu Leu
                325                 330                 335

Asp Asn Met Thr His Gly Gly Leu Gln Glu Leu Ala Gly Gly Val Leu
            340                 345                 350

Ser Ile Leu His Gly Leu Thr Pro Arg Pro Ala Arg Met Pro Ile Gly
        355                 360                 365

Asn Val Met Met Glu Ser Leu Gly Lys Gly Ser Val Ala Gln Ala Ile
    370                 375                 380

Ala Thr Tyr Arg Thr Leu Lys Lys Thr Lys Gln Ala Glu Tyr Asp Phe
385                 390                 395                 400

Ser Glu Arg His Leu Asn Thr Val Gly Tyr His Leu Leu Arg Ser Gly
                405                 410                 415

Arg Ala Ala Asp Ala Ile Glu Val Phe Lys Leu Asn Val Glu Met Phe
            420                 425                 430

Pro Glu Ala Ala Asn Cys His Asp Ser Leu Gly Glu Ala Tyr Ala Ala
        435                 440                 445

His Gly Asp Lys Ala Arg Ala Ile Thr Ser Tyr Arg Lys Ala Leu Glu
    450                 455                 460

Leu Ala Pro Lys Asn Glu His Ala Val Lys Met Leu Glu Gln Leu Glu
465                 470                 475                 480

Glu Pro Ala Ala Lys Arg
                485

<210> SEQ ID NO 14
<211> LENGTH: 218

```
<212> TYPE: PRT
<213> ORGANISM: Pseudomonas saudiphocaensis

<400> SEQUENCE: 14

Met Thr Asp Pro Leu Ile Ile Glu Pro Ala Gln Thr Ala Asp Ser Cys
1               5                   10                  15

Val Ile Trp Leu His Gly Leu Gly Ala Asp Arg Tyr Asp Phe Gln Pro
            20                  25                  30

Val Ala Glu Met Leu Gln Gln Arg Leu Leu His Thr Arg Phe Val Leu
        35                  40                  45

Pro Gln Ala Pro Thr Arg Ala Val Thr Ile Asn Gly Gly Trp Ala Met
50                  55                  60

Pro Ser Trp Tyr Asp Ile Gln Ala Met Ser Pro Ala Arg Ala Ile Asp
65                  70                  75                  80

Gln Ala Gln Leu Glu Gln Ser Ala Gln Thr Val Ile Glu Leu Ile Glu
                85                  90                  95

Gln Gln Arg Asp Ser Gly Ile Asp Pro Arg Arg Ile Phe Leu Ala Gly
            100                 105                 110

Phe Ser Gln Gly Gly Ala Val Val Tyr His Thr Ala Phe Leu Arg Trp
        115                 120                 125

Ala Gly Pro Leu Gly Gly Val Leu Ala Leu Ser Thr Tyr Ala Pro Thr
    130                 135                 140

Phe Gly Asp Asp Leu Lys Leu Ser Pro Leu Gln Ala Gly Leu Pro Val
145                 150                 155                 160

Leu Cys Leu His Gly Ser Arg Asp Asp Val Val Pro Pro Ala Met Gly
                165                 170                 175

Arg Ala Ala His Asp Cys Leu Gln Gln Asn Gln Val Gln Thr Gln Trp
            180                 185                 190

Lys Glu Tyr Pro Met Ala His Glu Val Gln Pro Thr Glu Ile Gln Asp
        195                 200                 205

Ile Gly Asp Trp Leu Ala Ser Arg Leu Gly
    210                 215

<210> SEQ ID NO 15
<211> LENGTH: 222
<212> TYPE: PRT
<213> ORGANISM: Ventosimonas gracilis

<400> SEQUENCE: 15

Met Thr Glu Pro Leu Ile Ile Glu Pro Ser Gln Pro Ala Asp Ser Ala
1               5                   10                  15

Val Ile Trp Leu His Gly Leu Gly Ala Asp Arg Phe Asp Phe Glu Pro
            20                  25                  30

Val Ala Arg Leu Leu Gly Gln His Leu Pro Ser Thr Arg Phe Ile Leu
        35                  40                  45

Pro Gln Ala Pro Thr Arg Pro Val Thr Phe Asn Met Gly His Ala Met
50                  55                  60

Pro Ser Trp Tyr Asp Ile Leu Ala Leu Asp Gly Ser Glu Arg Ala Ile
65                  70                  75                  80

Asn Pro Ala Asp Leu Glu Ala Ser Ser Glu Thr Leu Ile Ala Leu Ile
                85                  90                  95

Asn Ala Gln Gln Gln Ser Gly Ile Asp Ser Lys Arg Ile Val Leu Ala
            100                 105                 110

Gly Phe Ser Gln Gly Gly Ala Val Val Leu His Thr Ala Leu Leu Arg
        115                 120                 125
```

```
Phe Asp Glu Lys Leu Ala Gly Val Leu Ala Leu Ser Thr Tyr Ala Pro
    130                 135                 140

Thr Phe Asn Ala Glu Thr Gln Phe Ala Glu Ser Lys Gln Asn Leu Pro
145                 150                 155                 160

Val Leu Cys Met His Gly Ser Glu Asp Ala Val Leu Pro Ile Ser Met
                165                 170                 175

Gly Arg Ala Val Tyr Asp Lys Leu Ser Glu Gln Gly Ile Lys Ala Asn
                180                 185                 190

Trp Arg Asp Tyr Pro Met Gly His Glu Val Arg Pro Glu Gln Leu Arg
                195                 200                 205

Asp Ile Leu Asp Trp Leu Lys Asn Thr Leu Pro Ser Leu Pro
210                 215                 220
```

```
<210> SEQ ID NO 16
<211> LENGTH: 218
<212> TYPE: PRT
<213> ORGANISM: Pseudomonas fluorescens

<400> SEQUENCE: 16

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
                20                  25                  30

Val Ala Glu Ala Leu Gln Glu Ser Leu Leu Thr Thr Arg Phe Val Leu
                35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala His Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
                100                 105                 110

Phe Ser Gln Gly Gly Ala Val Val Phe His Thr Ala Phe Ile Asn Trp
            115                 120                 125

Gln Gly Pro Leu Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
                180                 185                 190

Gln Glu Tyr Pro Met Gly His Glu Val Leu Pro Gln Glu Ile His Asp
                195                 200                 205

Ile Gly Ala Trp Leu Ala Ala Arg Leu Gly
    210                 215
```

```
<210> SEQ ID NO 17
<211> LENGTH: 218
<212> TYPE: PRT
<213> ORGANISM: Pseudomonas fluorescens

<400> SEQUENCE: 17

Met Thr Glu Pro Leu Ile Leu Gln Pro Ala Lys Pro Ala Asp Ala Cys
1               5                   10                  15
```

```
Val Ile Trp Leu His Gly Leu Gly Ala Asp Arg Tyr Gly Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala Met Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
                100                 105                 110

Phe Ser Gln Gly Gly Ala Val Val Phe His Thr Ala Phe Ile Asn Trp
            115                 120                 125

Gln Gly Pro Leu Gly Gly Val Ile Ala Leu Ser Thr Tyr Ala Pro Thr
        130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
                180                 185                 190

Gln Glu Tyr Pro Met Gly His Glu Val Leu Pro Gln Glu Ile His Asp
                195                 200                 205

Ile Gly Ala Trp Leu Ala Ala Arg Leu Gly
            210                 215

<210> SEQ ID NO 18
<211> LENGTH: 218
<212> TYPE: PRT
<213> ORGANISM: Pseudomonas fluorescens

<400> SEQUENCE: 18

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala Val Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
                100                 105                 110

Phe Ser Gln Gly Gly Ala Val Val Phe His Thr Ala Phe Ile Asn Trp
            115                 120                 125

Gln Gly Pro Leu Gly Gly Val Ile Ala Leu Ser Thr Tyr Ala Pro Thr
        130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175
```

```
Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
        210                 215

<210> SEQ ID NO 19
<211> LENGTH: 218
<212> TYPE: PRT
<213> ORGANISM: Pseudomonas fluorescens

<400> SEQUENCE: 19

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala Met Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Ser Val Leu Pro Gln Glu Ile His Asp
        195                 200                 205

Ile Gly Ala Trp Leu Ala Ala Arg Leu Gly
    210                 215

<210> SEQ ID NO 20
<211> LENGTH: 218
<212> TYPE: PRT
<213> ORGANISM: Pseudomonas fluorescens

<400> SEQUENCE: 20

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60
```

Pro Ser Trp Tyr Asp Ile Lys Ala Met Ser Pro Ala Arg Ser Ile Ser
65                  70                  75                  80

Leu Glu Glu Leu Glu Val Ser Ala Lys Met Val Thr Asp Leu Ile Glu
            85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
            115                 120                 125

Gln Gly Pro Leu Gly Gly Val Ile Ala Leu Ser Thr Tyr Ala Pro Thr
            130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
            165                 170                 175

Arg Ser Ala Phe Glu His Leu Lys Ser Arg Gly Val Thr Val Thr Trp
            180                 185                 190

Gln Glu Tyr Pro Met Gly His Thr Val Leu Pro Gln Glu Ile His Asp
            195                 200                 205

Ile Gly Ala Trp Leu Ala Ala Arg Leu Gly
            210                 215

<210> SEQ ID NO 21
<211> LENGTH: 218
<212> TYPE: PRT
<213> ORGANISM: Pseudomonas fluorescens

<400> SEQUENCE: 21

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30

Val Ala Glu Ala Leu Gln Glu Ser Leu Leu Thr Thr Arg Phe Val Leu
            35                  40                  45

Pro Gln Ala Pro Thr Arg Pro Val Thr Ile Asn Gly Gly Tyr Glu Met
50                  55                  60

Ser Ser Trp Tyr Asp Ile Lys Ala His Ser Pro Ala Arg Ser Ile Ser
65                  70                  75                  80

Leu Glu Glu Leu Glu Val Ser Ala Lys Met Val Thr Asp Leu Ile Glu
            85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
            115                 120                 125

Gln Gly Pro Leu Gly Gly Val Ile Ala Leu Ser Thr Tyr Ala Pro Thr
            130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
            165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
            195                 200                 205

Ile Gly Ala Trp Leu Ala Ala Arg Leu Gly

<210> SEQ ID NO 22
<211> LENGTH: 218
<212> TYPE: PRT
<213> ORGANISM: Pseudomonas fluorescens

<400> SEQUENCE: 22

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Asp Met
    50                  55                  60

Pro Ser Trp Tyr Asp Ile Lys Ala Met Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
    210                 215

<210> SEQ ID NO 23
<211> LENGTH: 218
<212> TYPE: PRT
<213> ORGANISM: Pseudomonas fluorescens

<400> SEQUENCE: 23

Met Thr Glu Pro Leu Ile Leu Gln Pro Ala Lys Pro Ala Asp Ala Cys
1               5                   10                  15

Val Ile Trp Leu His Gly Leu Gly Gly Asp Arg Tyr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Leu Lys Ala Val Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly

```
                 100                 105                 110
Phe Ser Gln Gly Gly Ala Val Val Phe His Thr Ala Phe Ile Asn Trp
            115                 120                 125
Gln Gly Pro Leu Gly Gly Val Ile Ala Leu Ser Thr Tyr Ala Pro Thr
        130                 135                 140
Phe Gly Asp Glu Leu Glu Leu Ser Ala Ser Gln Gln Arg Ile Pro Ala
145                 150                 155                 160
Leu Cys Leu His Gly Gln Tyr Asp Asp Val Val Gln Asn Ala Met Gly
                165                 170                 175
Arg Ser Ala Phe Glu His Leu Lys Ser Arg Gly Val Thr Val Thr Trp
            180                 185                 190
Gln Glu Tyr Pro Met Gly His Glu Val Leu Pro Gln Glu Ile His Asp
        195                 200                 205
Ile Gly Ala Trp Leu Ala Ala Arg Leu Gly
210                 215

<210> SEQ ID NO 24
<211> LENGTH: 218
<212> TYPE: PRT
<213> ORGANISM: Pseudomonas fluorescens

<400> SEQUENCE: 24

Met Thr Glu Pro Leu Ile Leu Gln Pro Ala Lys Pro Ala Asp Ala Cys
1               5                   10                  15
Val Ile Trp Leu His Gly Leu Gly Ala Asp Arg Tyr Asp Phe Met Pro
            20                  25                  30
Val Ala Glu Ala Leu Gln Glu Ser Leu Leu Thr Thr Arg Phe Val Leu
        35                  40                  45
Pro Gln Ala Pro Thr Arg Pro Val Thr Ile Asn Gly Gly Tyr Glu Met
    50                  55                  60
Pro Ser Trp Tyr Asp Leu Lys Ala Val Ser Pro Ala Arg Ser Ile Ser
65                  70                  75                  80
Leu Glu Glu Leu Glu Val Ser Ala Lys Met Val Thr Asp Leu Ile Glu
                85                  90                  95
Ala Gln Lys Arg Thr Gly Ile Asp Ala Ser Arg Ile Phe Leu Ala Gly
            100                 105                 110
Phe Ser Gln Gly Gly Ala Val Val Phe His Thr Ala Phe Ile Asn Trp
        115                 120                 125
Gln Gly Pro Leu Gly Gly Val Ile Ala Leu Ser Thr Tyr Ala Pro Thr
    130                 135                 140
Phe Gly Asp Glu Leu Glu Leu Ser Ala Ser Gln Gln Arg Ile Pro Ala
145                 150                 155                 160
Leu Cys Leu His Gly Gln Tyr Asp Asp Val Val Gln Asn Ala Met Gly
                165                 170                 175
Arg Ser Ala Phe Glu His Leu Lys Ser Arg Gly Val Thr Val Thr Trp
            180                 185                 190
Gln Glu Tyr Pro Met Gly His Ser Val Leu Pro Gln Glu Ile His Asp
        195                 200                 205
Ile Gly Ala Trp Leu Ala Ala Arg Leu Gly
210                 215

<210> SEQ ID NO 25
<211> LENGTH: 218
<212> TYPE: PRT
<213> ORGANISM: Pseudomonas fluorescens
```

<400> SEQUENCE: 25

```
Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala Met Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Thr Ile Leu Pro Gln Glu Ile His Asp
        195                 200                 205

Ile Gly Ala Trp Leu Ala Ala Arg Leu Gly
    210                 215
```

<210> SEQ ID NO 26
<211> LENGTH: 218
<212> TYPE: PRT
<213> ORGANISM: Pseudomonas fluorescens

<400> SEQUENCE: 26

```
Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala Val Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140
```

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Ser Val Leu Pro Gln Glu Ile His Asp
        195                 200                 205

Ile Gly Ala Trp Leu Ala Ala Arg Leu Gly
    210                 215

<210> SEQ ID NO 27
<211> LENGTH: 218
<212> TYPE: PRT
<213> ORGANISM: Pseudomonas fluorescens

<400> SEQUENCE: 27

Met Thr Glu Pro Leu Ile Leu Gln Pro Ala Lys Pro Ala Asp Ala Cys
1               5                   10                  15

Val Ile Trp Leu His Gly Leu Gly Ala Gly Arg Thr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Leu Lys Ala Val Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
    210                 215

<210> SEQ ID NO 28
<211> LENGTH: 218
<212> TYPE: PRT
<213> ORGANISM: Pseudomonas fluorescens

<400> SEQUENCE: 28

Met Thr Glu Pro Leu Ile Leu Gln Pro Ala Lys Pro Ala Asp Ala Cys
1               5                   10                  15

Val Ile Trp Leu His Gly Leu Gly Ala Gly Arg Thr Ser His Arg Pro
            20                  25                  30

-continued

```
Val Ala Glu Ala Leu Gln Glu Ser Leu Leu Thr Thr Arg Phe Val Leu
             35                  40                  45

Pro Gln Ala Pro Thr Arg Pro Val Thr Ile Asn Gly Gly Tyr Glu Met
 50                  55                  60

Pro Ser Trp Tyr Asp Ile Lys Ala Met Ser Pro Ala Arg Ser Ile Ser
 65                  70                  75                  80

Leu Glu Glu Leu Glu Val Ser Ala Lys Met Val Thr Asp Leu Ile Glu
                 85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
    210                 215

<210> SEQ ID NO 29
<211> LENGTH: 218
<212> TYPE: PRT
<213> ORGANISM: Pseudomonas fluorescens

<400> SEQUENCE: 29

Met Thr Glu Pro Leu Ile Leu Gln Pro Ala Lys Pro Ala Asp Ala Cys
 1               5                  10                  15

Val Ile Trp Leu His Gly Leu Gly Ala Asp Arg Tyr Asp Phe Lys Pro
             20                  25                  30

Val Ala Glu Ala Leu Gln Glu Ser Leu Leu Thr Thr Arg Phe Val Leu
             35                  40                  45

Pro Gln Ala Pro Thr Arg Pro Val Thr Ile Asn Gly Gly Tyr Glu Met
 50                  55                  60

Pro Ser Trp Tyr Asp Ile Lys Ala Met Ser Pro Ala Arg Ser Ile Ser
 65                  70                  75                  80

Leu Glu Glu Leu Glu Val Ser Ala Lys Met Val Thr Asp Leu Ile Glu
                 85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190
```

Gln Glu Tyr Pro Met Gly His Glu Val Leu Pro Gln Glu Ile His Asp
        195                 200                 205

Ile Gly Ala Trp Leu Ala Ala Arg Leu Gly
        210                 215

<210> SEQ ID NO 30
<211> LENGTH: 218
<212> TYPE: PRT
<213> ORGANISM: Pseudomonas fluorescens

<400> SEQUENCE: 30

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Arg Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala Met Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
        210                 215

<210> SEQ ID NO 31
<211> LENGTH: 218
<212> TYPE: PRT
<213> ORGANISM: Pseudomonas fluorescens

<400> SEQUENCE: 31

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Leu Lys Ala Met Ser Pro Ala Arg Ser Ile Ser
65                  70                  75                  80

```
Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
                100                 105                 110

Phe Ser Gln Gly Gly Ala Val Val Phe His Thr Ala Phe Ile Asn Trp
                115                 120                 125

Gln Gly Pro Leu Gly Gly Val Ile Ala Leu Ser Thr Tyr Ala Pro Thr
            130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
                180                 185                 190

Gln Glu Tyr Pro Met Gly His Glu Val Leu Pro Gln Glu Ile His Asp
                195                 200                 205

Ile Gly Ala Trp Leu Ala Ala Arg Leu Gly
            210                 215

<210> SEQ ID NO 32
<211> LENGTH: 218
<212> TYPE: PRT
<213> ORGANISM: Pseudomonas fluorescens

<400> SEQUENCE: 32

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
                20                  25                  30

Val Ala Glu Ala Leu Gln Glu Ser Leu Leu Thr Thr Arg Phe Val Leu
                35                  40                  45

Pro Gln Ala Pro Thr Arg Pro Val Thr Ile Asn Gly Gly Tyr Glu Met
            50                  55                  60

Pro Ser Trp Tyr Asp Ile Lys Ala Leu Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
                100                 105                 110

Phe Ser Gln Gly Gly Ala Val Val Phe His Thr Ala Phe Ile Asn Trp
                115                 120                 125

Gln Gly Pro Leu Gly Gly Val Ile Ala Leu Ser Thr Tyr Ala Pro Thr
            130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
                180                 185                 190

Gln Glu Tyr Pro Met Gly His Glu Val Leu Pro Gln Glu Ile His Asp
                195                 200                 205

Ile Gly Ala Trp Leu Ala Ala Arg Leu Gly
            210                 215
```

```
<210> SEQ ID NO 33
<211> LENGTH: 218
<212> TYPE: PRT
<213> ORGANISM: Pseudomonas fluorescens

<400> SEQUENCE: 33
```

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Thr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala Val Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
    210                 215

```
<210> SEQ ID NO 34
<211> LENGTH: 218
<212> TYPE: PRT
<213> ORGANISM: Pseudomonas fluorescens

<400> SEQUENCE: 34
```

Met Thr Glu Pro Leu Ile Leu Gln Pro Ala Lys Pro Ala Asp Ala Cys
1               5                   10                  15

Val Ile Trp Leu His Gly Leu Gly Ala Gly Arg Tyr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala Val Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp

```
                    115                 120                 125
Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
    210                 215

<210> SEQ ID NO 35
<211> LENGTH: 218
<212> TYPE: PRT
<213> ORGANISM: Pseudomonas fluorescens

<400> SEQUENCE: 35

Met Thr Glu Pro Leu Ile Leu Gln Pro Ala Lys Pro Ala Asp Ala Cys
1               5                   10                  15

Val Ile Trp Leu His Gly Leu Gly Asp Arg Thr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala Met Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
    210                 215

<210> SEQ ID NO 36
<211> LENGTH: 218
<212> TYPE: PRT
<213> ORGANISM: Pseudomonas fluorescens

<400> SEQUENCE: 36

Met Thr Glu Pro Leu Ile Leu Gln Pro Ala Lys Pro Ala Asp Ala Cys
```

```
                1               5                    10                   15
Val Ile Trp Leu His Gly Leu Gly Ala Asp Arg Tyr Asp Phe Met Pro
                20                   25                   30

Val Ala Glu Ala Leu Gln Glu Ser Leu Leu Thr Thr Arg Phe Val Leu
                35                   40                   45

Pro Gln Ala Pro Thr Arg Pro Val Thr Ile Asn Gly Gly Tyr Glu Met
                50                   55                   60

Pro Ser Trp Tyr Asp Leu Lys Ala Ser Pro Ala Arg Ser Ile Ser
65                  70                   75                   80

Leu Glu Glu Leu Glu Val Ser Ala Lys Met Val Thr Asp Leu Ile Glu
                        85                   90                   95

Ala Gln Lys Arg Thr Gly Ile Asp Ala Ser Arg Ile Phe Leu Ala Gly
                    100                  105                  110

Phe Ser Gln Gly Gly Ala Val Val Phe His Thr Ala Phe Ile Asn Trp
                    115                  120                  125

Gln Gly Pro Leu Gly Gly Val Ile Ala Leu Ser Thr Tyr Ala Pro Thr
                    130                  135                  140

Phe Gly Asp Glu Leu Glu Leu Ser Ala Ser Gln Gln Arg Ile Pro Ala
145                  150                  155                  160

Leu Cys Leu His Gly Gln Tyr Asp Asp Val Val Gln Asn Ala Met Gly
                    165                  170                  175

Arg Ser Ala Phe Glu His Leu Lys Ser Arg Gly Val Thr Val Thr Trp
                    180                  185                  190

Gln Glu Tyr Pro Met Gly His Glu Val Leu Pro Gln Glu Ile His Asp
                    195                  200                  205

Ile Gly Ala Trp Leu Ala Ala Arg Leu Gly
                    210                  215

<210> SEQ ID NO 37
<211> LENGTH: 218
<212> TYPE: PRT
<213> ORGANISM: Pseudomonas fluorescens

<400> SEQUENCE: 37

Met Thr Glu Pro Leu Ile Leu Gln Pro Ala Lys Pro Ala Asp Ala Cys
1               5                    10                   15

Val Ile Trp Leu His Gly Leu Gly Ala Asp Arg Tyr Asp Phe Met Pro
                20                   25                   30

Val Ala Glu Ala Leu Gln Glu Ser Leu Leu Thr Thr Arg Phe Val Leu
                35                   40                   45

Pro Gln Ala Pro Thr Arg Pro Val Thr Ile Asn Gly Gly Tyr Glu Met
                50                   55                   60

Pro Ser Trp Tyr Asp Leu Lys Ala Leu Ser Pro Ala Arg Ser Ile Ser
65                  70                   75                   80

Leu Glu Glu Leu Glu Val Ser Ala Lys Met Val Thr Asp Leu Ile Glu
                        85                   90                   95

Ala Gln Lys Arg Thr Gly Ile Asp Ala Ser Arg Ile Phe Leu Ala Gly
                    100                  105                  110

Phe Ser Gln Gly Gly Ala Val Val Phe His Thr Ala Phe Ile Asn Trp
                    115                  120                  125

Gln Gly Pro Leu Gly Gly Val Ile Ala Leu Ser Thr Tyr Ala Pro Thr
                    130                  135                  140

Phe Gly Asp Glu Leu Glu Leu Ser Ala Ser Gln Gln Arg Ile Pro Ala
145                  150                  155                  160
```

```
Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
    210                 215

<210> SEQ ID NO 38
<211> LENGTH: 218
<212> TYPE: PRT
<213> ORGANISM: Pseudomonas fluorescens

<400> SEQUENCE: 38

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp His Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala Met Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
    210                 215

<210> SEQ ID NO 39
<211> LENGTH: 218
<212> TYPE: PRT
<213> ORGANISM: Pseudomonas fluorescens

<400> SEQUENCE: 39

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30

Val Ala Glu Ala Leu Gln Glu Ser Leu Leu Thr Thr Arg Phe Val Leu
        35                  40                  45
```

```
Pro Gln Ala Pro Thr Arg Pro Val Thr Ile Asn Gly Gly Tyr Glu Met
        50                  55                  60

Pro Ser Trp Tyr Asp Ile Lys Ala Met Ser Pro Ala Arg Ser Ile Ser
 65                  70                  75                  80

Leu Glu Glu Leu Glu Val Ser Ala Lys Met Val Thr Asp Leu Ile Glu
                 85                  90                  95

Ala Gln Lys Arg Thr Gly Ile Asp Ala Ser Arg Ile Phe Leu Ala Gly
                100                 105                 110

Phe Ser Gln Gly Gly Ala Val Val Phe His Thr Ala Phe Ile Asn Trp
            115                 120                 125

Gln Gly Pro Leu Gly Gly Val Ile Ala Val Asn Thr Tyr Ala Pro Thr
        130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
                180                 185                 190

Gln Glu Tyr Pro Met Gly His Glu Val Leu Pro Gln Glu Ile His Asp
            195                 200                 205

Ile Gly Ala Trp Leu Ala Ala Arg Leu Gly
        210                 215

<210> SEQ ID NO 40
<211> LENGTH: 218
<212> TYPE: PRT
<213> ORGANISM: Pseudomonas fluorescens

<400> SEQUENCE: 40

Met Thr Glu Pro Leu Ile Leu Gln Pro Ala Lys Pro Ala Asp Ala Cys
 1               5                  10                  15

Val Ile Trp Leu His Gly Leu Gly Gly Asp Arg Tyr Asp Phe Met Pro
                 20                  25                  30

Val Ala Glu Ala Leu Gln Glu Ser Leu Leu Thr Thr Arg Phe Val Leu
             35                  40                  45

Pro Gln Ala Pro Thr Arg Pro Val Thr Ile Asn Gly Gly Tyr Glu Met
        50                  55                  60

Pro Ser Trp Tyr Asp Ile Lys Ala Met Ser Pro Ala Arg Ser Ile Ser
 65                  70                  75                  80

Leu Glu Glu Leu Glu Val Ser Ala Lys Met Val Thr Asp Leu Ile Glu
                 85                  90                  95

Ala Gln Lys Arg Thr Gly Ile Asp Ala Ser Arg Ile Phe Leu Ala Gly
                100                 105                 110

Phe Ser Gln Gly Gly Ala Val Val Phe His Thr Ala Phe Ile Asn Trp
            115                 120                 125

Gln Gly Pro Leu Gly Gly Val Ile Ala Leu Ser Thr Tyr Ala Pro Thr
        130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
                180                 185                 190

Gln Glu Tyr Pro Met Gly His Glu Val Leu Pro Gln Glu Ile His Asp
            195                 200                 205
```

Ile Gly Ala Trp Leu Ala Ala Arg Leu Gly
    210                 215

<210> SEQ ID NO 41
<211> LENGTH: 218
<212> TYPE: PRT
<213> ORGANISM: Pseudomonas fluorescens

<400> SEQUENCE: 41

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Leu Lys Ala Val Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
    210                 215

<210> SEQ ID NO 42
<211> LENGTH: 218
<212> TYPE: PRT
<213> ORGANISM: Pseudomonas fluorescens

<400> SEQUENCE: 42

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Leu Lys Ala Ser Ser Pro Ala Arg Ser Ile Ser
65                  70                  75                  80

Leu Glu Glu Leu Glu Val Ser Ala Lys Met Val Thr Asp Leu Ile Glu
                85                  90                  95

-continued

```
Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
        195                 200                 205

Ile Gly Ala Trp Leu Ala Ala Arg Leu Gly
    210                 215

<210> SEQ ID NO 43
<211> LENGTH: 218
<212> TYPE: PRT
<213> ORGANISM: Pseudomonas fluorescens

<400> SEQUENCE: 43

Met Thr Glu Pro Leu Ile Leu Gln Pro Ala Lys Pro Ala Asp Ala Cys
1               5                   10                  15

Val Ile Trp Leu His Gly Leu Gly Ala Gly Arg Thr Ser His Arg Pro
            20                  25                  30

Val Ala Glu Ala Leu Gln Glu Ser Leu Leu Thr Thr Arg Phe Val Leu
        35                  40                  45

Pro Gln Ala Pro Thr Arg Pro Val Thr Ile Asn Gly Gly Tyr Glu Met
    50                  55                  60

Pro Ser Trp Tyr Asp Ile Lys Ala Met Ser Pro Ala Arg Ser Ile Ser
65                  70                  75                  80

Leu Glu Glu Leu Glu Val Ser Ala Lys Met Val Thr Asp Leu Ile Glu
                85                  90                  95

Ala Gln Lys Arg Thr Gly Ile Asp Ala Ser Arg Ile Phe Leu Ala Gly
            100                 105                 110

Phe Ser Gln Gly Gly Ala Val Val Phe His Thr Ala Phe Ile Asn Trp
        115                 120                 125

Gln Gly Pro Leu Gly Gly Val Ile Ala Leu Ser Thr Tyr Ala Pro Thr
    130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Thr Ile Leu Pro Gln Glu Ile His Asp
        195                 200                 205

Ile Gly Ala Trp Leu Ala Ala Arg Leu Gly
    210                 215

<210> SEQ ID NO 44
<211> LENGTH: 236
<212> TYPE: PRT
```

<213> ORGANISM: Chromohalobacter salexigens

<400> SEQUENCE: 44

Met Ala Asp Ser Ser Pro Leu Ile Ile Glu Pro Arg Gln Ala Arg Ala
1               5                   10                  15

Ala Asp Ala Thr Val Ile Leu Leu His Gly Leu Gly Ala Asp Gly His
            20                  25                  30

Asp Phe Glu Pro Leu Val Pro Ala Leu Pro Leu Ala Lys Asp Leu Ala
        35                  40                  45

Val Arg Phe Val Leu Pro His Ala Pro Arg Met Pro Val Thr Val Asn
50                  55                  60

Gly Gly Met Glu Met Pro Ala Trp Tyr Asp Ile Leu Asp Met Asn Leu
65                  70                  75                  80

Gly Arg Arg Ile Asp Glu Ala Gln Leu Lys Ala Ser Ala Asp Met Val
                85                  90                  95

His Gly Leu Ile Asp Ala Glu Ile Ala Arg Gly Ile Asp Ser Arg Arg
            100                 105                 110

Ile Ile Val Ala Gly Phe Ser Gln Gly Gly Ala Val Ala Tyr His Ala
        115                 120                 125

Ala Leu Thr Tyr Pro Lys Pro Leu Gly Gly Leu Leu Ala Leu Ser Thr
    130                 135                 140

Tyr Phe Ala Thr Ala Thr Ser Ile Glu Pro Ser Glu Ala Asn Arg Ala
145                 150                 155                 160

Leu Pro Ile Glu Val His His Gly Ser Phe Asp Pro Val Val Pro Glu
                165                 170                 175

Ala Leu Gly His Glu Gly Ala Glu Arg Ala Glu Ala Leu Gly Tyr Ala
            180                 185                 190

Val Thr Tyr Arg Thr Tyr Pro Met Gln His Ala Leu Cys Pro Glu Gln
        195                 200                 205

Ile Glu Asp Ile Gly Gln Trp Leu Asn Ala Arg Leu Gly Ala Lys Glu
    210                 215                 220

Ala Gly Gly Ser Leu Glu His His His His His
225                 230                 235

<210> SEQ ID NO 45
<211> LENGTH: 232
<212> TYPE: PRT
<213> ORGANISM: Halomonas sp.

<400> SEQUENCE: 45

Met Thr Ala Pro Gly Glu Leu Ile Ile Glu Pro Lys Asp Gly Gln Pro
1               5                   10                  15

Ala Asp Ala Cys Val Phe Ile Ile His Gly Leu Gly Ala Asp Gly His
            20                  25                  30

Asp Phe Glu Pro Leu Val Pro Ala Leu Ala Leu Pro Lys Asp Ser Arg
        35                  40                  45

Val Arg Phe Ile Met Pro His Ala Pro Arg Leu Pro Val Thr Ile Asn
50                  55                  60

Gly Gly Met Val Met Pro Ala Trp Tyr Asp Ile Leu Ala Met Asp Leu
65                  70                  75                  80

Gly Arg Arg Val Asp Glu Arg Gln Leu Lys Gln Ser Ala Glu Arg Ile
                85                  90                  95

Gln Ala Leu Ile Gln Glu Gln Ile Asp Gln Gly Ile Asp Ser Gln Arg
            100                 105                 110

Ile Ile Val Ala Gly Phe Ser Gln Gly Gly Ala Val Ala Tyr His Ala

```
                    115                 120                 125
Ala Leu Thr Phe Pro Ala Pro Leu Gly Gly Leu Leu Ala Met Ser Thr
    130                 135                 140

Tyr Phe Ala Thr Ala Asp Asn Ile Asp Leu Ala Glu Ala Asn Arg Gln
145                 150                 155                 160

Ile Pro Ile Glu Val Gln His Gly Asn Phe Asp Pro Ile Val Pro Glu
                165                 170                 175

Ser Leu Gly Arg Ser Gly Ala Asp Arg Leu Lys Glu Met Gly Tyr Ala
            180                 185                 190

Val Asn Tyr Arg Gln Tyr Pro Met Ala His Ala Leu Cys Pro Gln Gln
        195                 200                 205

Val Asn Asp Ile Gly Lys Trp Leu Ser Ala Arg Leu Asn Gly Gly Ser
    210                 215                 220

Leu Glu His His His His His His
225                 230

<210> SEQ ID NO 46
<211> LENGTH: 233
<212> TYPE: PRT
<213> ORGANISM: Francisella tularensis

<400> SEQUENCE: 46

Met Asn Tyr Glu Leu Met Glu Pro Ala Lys Gln Ala Arg Phe Cys Val
1               5                   10                  15

Ile Trp Leu His Gly Leu Gly Ala Asp Gly His Asp Phe Val Asp Ile
            20                  25                  30

Val Asn Tyr Phe Asp Val Ser Leu Asp Glu Ile Arg Phe Ile Phe Pro
        35                  40                  45

His Ala Asp Ile Ile Pro Val Thr Ile Asn Met Gly Met Gln Met Arg
    50                  55                  60

Ala Trp Tyr Asp Ile Lys Ser Leu Asp Ala Asn Ser Leu Asn Arg Val
65                  70                  75                  80

Val Asp Val Glu Gly Ile Asn Ser Ser Ile Ala Lys Val Asn Lys Leu
                85                  90                  95

Ile Asp Ser Gln Val Asn Gln Gly Ile Ala Ser Glu Asn Ile Ile Leu
            100                 105                 110

Ala Gly Phe Ser Gln Gly Gly Ile Ile Ala Thr Tyr Thr Ala Ile Thr
        115                 120                 125

Ser Gln Arg Lys Leu Gly Gly Ile Met Ala Leu Ser Thr Tyr Leu Pro
    130                 135                 140

Ala Trp Asp Asn Phe Lys Gly Lys Ile Thr Ser Ile Asn Lys Gly Leu
145                 150                 155                 160

Pro Ile Leu Val Cys His Gly Thr Asp Asp Gln Val Leu Pro Glu Val
                165                 170                 175

Leu Gly His Asp Leu Ser Asp Lys Leu Lys Val Ser Gly Phe Ala Asn
            180                 185                 190

Glu Tyr Lys His Tyr Val Gly Met Gln His Ser Val Cys Met Glu Glu
        195                 200                 205

Ile Lys Asp Ile Ser Asn Phe Ile Ala Lys Thr Phe Lys Ile Gly Gly
    210                 215                 220

Ser Leu Glu His His His His His His
225                 230

<210> SEQ ID NO 47
<211> LENGTH: 304
```

<212> TYPE: PRT
<213> ORGANISM: Sphingobium sp.

<400> SEQUENCE: 47

Met Thr Asn Asp Glu Arg Ile Leu Ser Trp Asn Glu Thr Pro Ser Lys
1               5                   10                  15

Pro Arg Tyr Thr Pro Pro Gly Ala Ile Asp Ala His Cys His Val
            20                  25                  30

Phe Gly Pro Met Ala Gln Phe Pro Phe Ser Pro Lys Ala Lys Tyr Leu
            35                  40                  45

Pro Arg Asp Ala Gly Pro Asp Met Leu Phe Ala Leu Arg Asp His Leu
50                  55                  60

Gly Phe Ala Arg Asn Val Ile Val Gln Ala Ser Cys His Gly Thr Asp
65                  70                  75                  80

Asn Ala Ala Thr Leu Asp Ala Ile Ala Arg Ala Gln Gly Lys Ala Arg
                85                  90                  95

Gly Ile Ala Val Val Asp Pro Ala Ile Asp Glu Ala Glu Leu Ala Ala
                100                 105                 110

Leu His Glu Gly Gly Met Arg Gly Ile Arg Phe Asn Phe Leu Lys Arg
            115                 120                 125

Leu Val Asp Asp Ala Pro Lys Asp Lys Phe Leu Glu Val Ala Gly Arg
130                 135                 140

Leu Pro Ala Gly Trp His Val Val Ile Tyr Phe Glu Ala Asp Ile Leu
145                 150                 155                 160

Glu Glu Leu Arg Pro Phe Met Asp Ala Ile Pro Val Pro Ile Val Ile
                165                 170                 175

Asp His Met Gly Arg Pro Asp Val Arg Gln Gly Pro Asp Gly Ala Asp
            180                 185                 190

Met Lys Ala Phe Arg Arg Leu Leu Asp Ser Arg Glu Asp Ile Trp Phe
            195                 200                 205

Lys Ala Thr Cys Pro Asp Arg Leu Asp Pro Ala Gly Pro Pro Trp Asp
210                 215                 220

Asp Phe Ala Arg Ser Val Ala Pro Leu Val Ala Asp Tyr Ala Asp Arg
225                 230                 235                 240

Val Ile Trp Gly Thr Asp Trp Pro His Pro Asn Met Gln Asp Ala Ile
                245                 250                 255

Pro Asp Asp Gly Leu Val Val Asp Met Ile Pro Arg Ile Ala Pro Thr
            260                 265                 270

Pro Glu Leu Gln His Lys Met Leu Val Thr Asn Pro Met Arg Leu Tyr
            275                 280                 285

Trp Ser Glu Glu Met Gly Gly Ser Leu Glu His His His His His His
            290                 295                 300

<210> SEQ ID NO 48
<211> LENGTH: 247
<212> TYPE: PRT
<213> ORGANISM: Pseudomonas putida

<400> SEQUENCE: 48

Met Leu Thr Glu Gly Ile Ser Ile Gln Ser Tyr Asp Gly His Thr Phe
1               5                   10                  15

Gly Ala Leu Val Gly Ser Pro Ala Lys Ala Pro Ala Pro Val Ile Val
            20                  25                  30

Ile Ala Gln Glu Ile Phe Gly Val Asn Ala Phe Met Arg Glu Thr Val
            35                  40                  45

```
Ser Trp Leu Val Asp Gln Gly Tyr Ala Ala Val Cys Pro Asp Leu Tyr
 50                  55                  60

Ala Arg Gln Ala Pro Gly Thr Ala Leu Asp Pro Gln Asp Glu Arg Gln
 65                  70                  75                  80

Arg Glu Gln Ala Tyr Lys Leu Trp Gln Ala Phe Asp Met Glu Ala Gly
                 85                  90                  95

Val Gly Asp Leu Glu Ala Ala Ile Arg Tyr Ala Arg His Gln Pro Tyr
            100                 105                 110

Ser Asn Gly Lys Val Gly Leu Val Gly Tyr Cys Leu Gly Gly Ala Leu
        115                 120                 125

Ala Phe Leu Val Ala Ala Lys Gly Tyr Val Asp Arg Ala Val Gly Tyr
130                 135                 140

Tyr Gly Val Gly Leu Glu Lys Gln Leu Lys Lys Val Pro Glu Val Lys
145                 150                 155                 160

His Pro Ala Leu Phe His Met Gly Gly Gln Asp His Phe Val Pro Ala
                165                 170                 175

Pro Ser Arg Gln Leu Ile Thr Glu Gly Phe Gly Ala Asn Pro Leu Leu
            180                 185                 190

Gln Val His Trp Tyr Glu Glu Ala Gly His Ser Phe Ala Arg Thr Ser
        195                 200                 205

Ser Ser Gly Tyr Val Ala Ser Ala Ala Ala Leu Ala Asn Glu Arg Arg
    210                 215                 220

Leu Asp Phe Leu Ala Pro Leu Gln Ser Lys Lys Pro Gly Gly Ser Leu
225                 230                 235                 240

Glu His His His His His His
                245

<210> SEQ ID NO 49
<211> LENGTH: 257
<212> TYPE: PRT
<213> ORGANISM: Geobacillus stearothermophilus

<400> SEQUENCE: 49

Met Lys Ile Val Pro Pro Lys Pro Phe Phe Phe Glu Ala Gly Glu Arg
 1               5                  10                  15

Ala Val Leu Leu Leu His Gly Phe Thr Gly Asn Ser Ala Asp Val Arg
                20                  25                  30

Met Leu Gly Arg Phe Leu Glu Ser Lys Gly Tyr Thr Cys His Ala Pro
            35                  40                  45

Ile Tyr Lys Gly His Gly Val Pro Pro Glu Glu Leu Val His Thr Gly
 50                  55                  60

Pro Asp Asp Trp Trp Gln Asp Val Met Asn Gly Tyr Glu Phe Leu Lys
 65                  70                  75                  80

Asn Lys Gly Tyr Glu Lys Ile Ala Val Ala Gly Leu Ser Leu Gly Gly
                 85                  90                  95

Val Phe Ser Leu Lys Leu Gly Tyr Thr Val Pro Ile Glu Gly Ile Val
            100                 105                 110

Thr Met Cys Ala Pro Met Tyr Ile Lys Ser Glu Glu Thr Met Tyr Glu
        115                 120                 125

Gly Val Leu Glu Tyr Ala Arg Glu Tyr Lys Lys Arg Glu Gly Lys Ser
130                 135                 140

Glu Glu Gln Ile Glu Gln Glu Met Glu Lys Phe Lys Gln Thr Pro Met
145                 150                 155                 160

Lys Thr Leu Lys Ala Leu Gln Glu Leu Ile Ala Asp Val Arg Asp His
                165                 170                 175
```

```
Leu Asp Leu Ile Tyr Ala Pro Thr Phe Val Gln Ala Arg His Asp
            180                 185                 190

Glu Met Ile Asn Pro Asp Ser Ala Asn Ile Ile Tyr Asn Glu Ile Glu
        195                 200                 205

Ser Pro Val Lys Gln Ile Lys Trp Tyr Glu Gln Ser Gly His Val Ile
    210                 215                 220

Thr Leu Asp Gln Glu Lys Asp Gln Leu His Glu Asp Ile Tyr Ala Phe
225                 230                 235                 240

Leu Glu Ser Leu Asp Trp Gly Gly Ser Leu Glu His His His His
                245                 250                 255

His

<210> SEQ ID NO 50
<211> LENGTH: 281
<212> TYPE: PRT
<213> ORGANISM: Unknown
<220> FEATURE:
<223> OTHER INFORMATION: Description of Unknown:
      Uncultured bacterium FLS12

<400> SEQUENCE: 50

Met Ala Leu Phe Gln Cys Asp Phe Phe Ser Asp Val Leu Gly Leu Ser
1               5                   10                  15

Thr Ser Met Thr Val Ile Leu Pro Gln Glu Thr Thr Gly Gln Ile Gly
            20                  25                  30

Met Ala Gly Gly Ser Glu Arg Arg Glu His Pro Thr Leu Phe Leu Leu
        35                  40                  45

His Gly Leu Ser Asp Asp His Thr Ile Trp Leu Arg Arg Thr Ser Ile
    50                  55                  60

Glu Arg Tyr Val Ala Glu Met Gly Leu Ala Val Val Met Pro Ala Val
65                  70                  75                  80

His Arg Ser Phe Tyr Thr Asp Met Ala His Gly Leu Gln Tyr Trp Thr
                85                  90                  95

Phe Ile Ser Glu Glu Leu Pro Ala Leu Ala Arg Ser Phe Phe Pro Leu
            100                 105                 110

Ala Thr Ala Arg Glu Asp Thr Phe Val Ala Gly Leu Ser Met Gly Gly
        115                 120                 125

Tyr Gly Ala Leu Lys Leu Gly Met Arg His Pro Glu Arg Phe Ala Ala
    130                 135                 140

Ala Ala Ser Leu Ser Gly Ala Leu Asp Ile Thr Phe Asp Pro Ala Glu
145                 150                 155                 160

His Ile Ala Met Glu Asp Asp Val Trp Val Ala Glu Gln Arg Asn Ile
                165                 170                 175

Phe Gly Asp Leu Ala Ala Leu Pro Gly Ser Asp His Asp Leu Phe Ala
            180                 185                 190

Leu Ala Glu Arg Met Ala Gln Ser Asp Gly Pro Val Pro Lys Leu Tyr
        195                 200                 205

Gln Cys Cys Gly Thr Glu Asp Phe Leu Tyr Glu Asp Asn Val Arg Phe
    210                 215                 220

Arg Asp His Val Arg Gly Leu Gly Leu Asp Phe Met Tyr Glu Glu Ser
225                 230                 235                 240

Pro Gly Glu His Glu Trp Gly Tyr Trp Asp Ala Gln Ile Gln Arg Val
                245                 250                 255

Leu Ala Trp Leu Pro Leu Arg Pro Pro Gly Thr Ala Pro Ala Gly Gly
            260                 265                 270
```

```
Ser Leu Glu His His His His His
        275                 280

<210> SEQ ID NO 51
<211> LENGTH: 259
<212> TYPE: PRT
<213> ORGANISM: Bradyrhizobium sp.

<400> SEQUENCE: 51

Met Ala Thr Glu Thr Ile Ala Met Asp Trp Val Asp Ile Gly Thr Asn
1               5                   10                  15

Gly Glu Ser Arg Leu Ala Tyr Leu Ala Arg Pro Val Val Thr Gly Arg
            20                  25                  30

Leu Pro Ala Val Ile Val Met Pro Ala Ile His Gly Ile Asn Thr Tyr
        35                  40                  45

Ile Lys Asp Val Ala Ile Asp Leu Ala Lys Ala Gly Phe Val Ala Leu
    50                  55                  60

Leu Ile Asp Ile His Ser Pro Glu Gln Glu Pro Asp Leu Ser Asn Ala
65                  70                  75                  80

Glu Lys Ile Gln Ile Ala Val Glu Thr Leu Asp Asp Arg Lys Val Leu
                85                  90                  95

Lys Asp Val Asp Ala Ala Val Arg Tyr Leu Glu Gln His Ala Ala Val
            100                 105                 110

Arg Ala Asp Arg Leu Gly Ile Leu Gly Phe Cys Val Gly Gly Thr Tyr
        115                 120                 125

Ala Leu Leu Ala Ala Arg Thr Pro Ala Ile Arg Val Ser Val Gly Phe
    130                 135                 140

Tyr Gly Leu Leu Glu Tyr Gln Ser Arg Thr Asp Asn Lys Pro Val Ser
145                 150                 155                 160

Pro Leu Asp Ser Val Ala Gln Phe Thr Ala Pro Ile Leu Phe His Val
                165                 170                 175

Gly Asp Lys Asp Pro Trp Ile Asp Ser Lys Met Leu Ala Glu Phe Thr
            180                 185                 190

Lys Arg Met Gln Gln His Gln Lys Ser Tyr Glu Leu Cys Ile Tyr Arg
        195                 200                 205

Gly Ala Gly His Ala Phe His Glu His Phe Arg Asp Ala Tyr Arg Pro
    210                 215                 220

Ile Ala Ala Gln Ser Ala Trp Asn Asn Thr Leu Ile Tyr Leu Arg Trp
225                 230                 235                 240

His Leu Cys Gly Lys Arg Thr Val Gly Gly Ser Leu Glu His His His
                245                 250                 255

His His His

<210> SEQ ID NO 52
<211> LENGTH: 497
<212> TYPE: PRT
<213> ORGANISM: Myxococcus fulvus

<400> SEQUENCE: 52

Met Asn Gly Leu Arg Trp Arg Leu Thr Gly Val Val Met Ala Trp Val
1               5                   10                  15

Leu Val Ala Pro Leu Ala Glu Ala Ala Asn Val Lys Gln Glu Val Asp
            20                  25                  30

Arg Tyr Ile Ser Gly Phe His Gln Lys Gly Leu Phe Asn Gly Thr Val
        35                  40                  45
```

```
Leu Val Ala Asn Glu Arg Gly Ile Leu Leu Lys Lys Gly Tyr Gly Ala
 50                  55                  60

Ala Asn Leu Glu Trp Lys Val Pro Asn Ala Pro Asp Thr Lys Phe Arg
 65                  70                  75                  80

Ile Gly Ser Ile Thr Lys Ser Phe Thr Ala Thr Val Ile Leu Gln Leu
                 85                  90                  95

Ala Ala Glu Gly Lys Leu Gln Leu Asp Asp Pro Ile Thr Lys His Leu
                100                 105                 110

Pro Asp Tyr Arg Lys Asp Thr Gly Asp Arg Val Thr Ile Thr His Leu
            115                 120                 125

Leu Asn His Thr Ser Gly Ile Pro Ser Tyr Thr Ser Lys Pro Ala Ile
130                 135                 140

Met Lys Asp Ala Asp Gly Phe Glu Ser Val Ala Ala Phe Val Lys Lys
145                 150                 155                 160

Ala Cys Ser Asp Asp Leu Glu Phe Glu Pro Gly Thr Lys Tyr Ala Tyr
                165                 170                 175

Asn Asn Ser Gly Tyr Phe Leu Leu Gly Ala Ile Ile Glu Lys Leu Thr
            180                 185                 190

Gly Gln Thr Tyr Ala Glu Ala Val Gln Ala Arg Ile Leu Gly Pro Leu
        195                 200                 205

Gly Met Lys Asp Thr Gly Tyr Asp Val Ser Ala Thr Val Leu Pro Lys
210                 215                 220

Arg Ala Ser Gly Tyr Ala Gln Ala Pro Gly Gly Ile Val Asn Ala Ala
225                 230                 235                 240

Trp Leu Asp Met Asn Leu Pro Tyr Ala Ala Gly Ser Leu Tyr Ser Thr
                245                 250                 255

Val Glu Asp Leu Tyr Arg Trp Glu Arg Ala Phe His Gly Asp Thr Leu
            260                 265                 270

Leu Pro Ala Ala Leu Lys Gln Lys Met Leu Thr Pro Gly Leu Ala His
        275                 280                 285

Tyr Gly Phe Gly Trp Val Met Ser Asp Met Thr Leu His Asp Gly Lys
290                 295                 300

Thr Lys Leu Pro Gly Ile Phe His Thr Gly Gly Ile Asn Gly Phe Ser
305                 310                 315                 320

Ser Ile Leu Val Arg Val Pro Glu Arg Lys Glu Ala Val Ile Leu Leu
                325                 330                 335

Asp Asn Met Thr His Gly Gly Leu Gln Glu Leu Ala Gly Gly Val Leu
            340                 345                 350

Ser Ile Leu His Gly Leu Thr Pro Arg Pro Ala Arg Met Pro Ile Gly
        355                 360                 365

Asn Val Met Met Glu Ser Leu Gly Lys Gly Ser Val Ala Gln Ala Ile
370                 375                 380

Ala Thr Tyr Arg Thr Leu Lys Lys Thr Lys Gln Ala Glu Tyr Asp Phe
385                 390                 395                 400

Ser Glu Arg His Leu Asn Thr Val Gly Tyr His Leu Leu Arg Ser Gly
                405                 410                 415

Arg Ala Ala Asp Ala Ile Glu Val Phe Lys Leu Asn Val Glu Met Phe
            420                 425                 430

Pro Glu Ala Ala Asn Cys His Asp Ser Leu Gly Glu Ala Tyr Ala Ala
        435                 440                 445

His Gly Asp Lys Ala Arg Ala Ile Thr Ser Tyr Arg Lys Ala Leu Glu
450                 455                 460

Leu Ala Pro Lys Asn Glu His Ala Val Lys Met Leu Glu Gln Leu Glu
```

```
                465                 470                 475                 480
Glu Pro Ala Ala Lys Arg Gly Gly Ser Leu Glu His His His His
                    485                 490                 495

His

<210> SEQ ID NO 53
<211> LENGTH: 279
<212> TYPE: PRT
<213> ORGANISM: Mesorhizobium japonicum

<400> SEQUENCE: 53

Met Ser Asp Thr Lys Val Tyr Leu Leu Asp Gly Gly Ser Leu Val Leu
1               5                   10                  15

Asp Gly Tyr His Val Phe Trp Asn Arg Gly Pro Gly Gly Glu Val Arg
            20                  25                  30

Phe Pro Val Tyr Ser Ile Leu Ile Glu His Ala Glu Gly Arg Phe Leu
        35                  40                  45

Ile Asp Thr Gly Tyr Asp Tyr Asp His Val Met Lys Val Leu Pro Phe
    50                  55                  60

Glu Lys Pro Ile Gln Glu Lys His Gln Thr Ile Pro Gly Ala Leu Gly
65                  70                  75                  80

Leu Leu Gly Leu Glu Pro Arg Asp Ile Asp Val Val Asn Ser His
                85                  90                  95

Phe His Phe Asp His Cys Gly Gly Asn Lys Tyr Phe Pro His Ala Lys
            100                 105                 110

Lys Ile Cys His Arg Ser Glu Val Pro Gln Ala Cys Asn Pro Gln Pro
        115                 120                 125

Phe Glu His Leu Gly Tyr Ser Asp Leu Ser Phe Ser Ala Glu Ala Ala
    130                 135                 140

Glu Ala Arg Gly Ala Thr Ala Gln Leu Leu Glu Gly Thr Thr Arg Ala
145                 150                 155                 160

Asn Ser Thr Phe Glu Gly Ile Asp Gly Asp Val Asp Leu Ala Arg Gly
                165                 170                 175

Val Lys Leu Ile Ser Thr Pro Gly His Ser Ile Gly His Tyr Ser Leu
            180                 185                 190

Leu Val Glu Phe Pro Arg Arg Lys Pro Ile Leu Phe Thr Ile Asp Ala
        195                 200                 205

Ala Tyr Thr Gln Lys Ser Leu Glu Thr Leu Cys Gln Ala Ala Phe His
    210                 215                 220

Ile Asp Pro Val Ala Gly Val Asn Ser Met Arg Lys Val Lys Lys Leu
225                 230                 235                 240

Ala Glu Asp His Gly Ala Glu Leu Met Tyr Ser His Asp Met Asp Asn
                245                 250                 255

Phe Lys Thr Tyr Arg Thr Gly Thr Gln Phe Tyr Gly Gly Ser Leu
            260                 265                 270

Glu His His His His His His
        275

<210> SEQ ID NO 54
<211> LENGTH: 310
<212> TYPE: PRT
<213> ORGANISM: Rhizobium radiobacter

<400> SEQUENCE: 54

Met Leu Pro Ala Asp Gln Ala Gly Ile Pro Pro Cys Gln Gly Pro Arg
1               5                   10                  15
```

Ala Arg Ser Ala Pro Ile Ser Phe Ala Ile Pro Lys Gly Ala Trp Asp
            20                  25                  30

Thr His Leu His Val Phe Gly Pro Thr Ala Val Phe Pro Tyr Ala Glu
            35                  40                  45

Lys Arg Pro Tyr Thr Pro Pro Asp Ser Pro Leu Glu Asp Tyr Leu Ala
 50                      55                  60

Leu Met Glu Arg Leu Gly Ile Glu Arg Gly Val Cys Val His Pro Asn
 65                  70                  75                  80

Val His Gly Ile Asp Asn Ser Val Thr Ile Asp Ala Val Glu Arg Ser
                    85                  90                  95

Asp Arg Arg Leu Leu Gly Ile Ile Lys Pro His Arg Val Met Thr Phe
                100                 105                 110

Thr Glu Leu Arg Asp Leu Lys Thr Arg Gly Val Arg Gly Val Arg Phe
            115                 120                 125

Ala Phe Asn Pro Gln His Gly Ser Gly Ala Leu Asp Thr Glu Leu Phe
130                 135                 140

Glu Arg Met His Gly Trp Cys Arg Glu Leu Asp Trp Cys Ile Asn Met
145                 150                 155                 160

His Phe Ala Pro Asp Ala Leu Glu Gly Leu Cys Asp Leu Ile Ala Gly
                165                 170                 175

Ala Glu Thr Pro Ile Ile Ile Asp His Phe Gly Arg Val Glu Thr Ala
            180                 185                 190

Ala Gly Val Asn Gln Leu Pro Phe Lys Ile Leu Arg Asp Leu Ala Thr
            195                 200                 205

Leu Asp His Val Trp Ile Lys Leu Thr Gly Ala Asp Arg Ile Ser His
210                 215                 220

Ser Gly Val Pro Tyr Asp Asp Val Val Pro Phe Ala His Ala Leu Ser
225                 230                 235                 240

Glu Ile Ala Pro Asp Arg Leu Leu Trp Gly Ser Asp Trp Pro His Ser
                245                 250                 255

Gly Tyr Phe Asp Pro Lys Arg Met Pro Asp Asp Gly Asp Leu Leu Asn
                260                 265                 270

Leu Val Ala Arg Phe Ala Pro Asp Val Ala Leu Arg His Lys Ile Leu
            275                 280                 285

Val Asp Asn Pro Ala Arg Leu Phe Gly Val Ile Gly Gly Ser Leu Glu
290                 295                 300

His His His His His His
305                 310

<210> SEQ ID NO 55
<211> LENGTH: 393
<212> TYPE: PRT
<213> ORGANISM: Aeromonas enteropelogenes

<400> SEQUENCE: 55

Met Lys Gln Arg Ile Ala Leu Ser Leu Leu Ala Leu Gly Pro Leu Leu
 1                   5                  10                  15

Leu Val Pro Arg Val Tyr Ala Ala Ala Asp Glu Pro Met Ala Asn Ile
            20                  25                  30

Val Glu Lys Ala Val Gln Pro Leu Glu Glu Tyr Arg Ile Pro Gly
            35                  40                  45

Met Ala Val Ala Val Leu Lys Glu Gly Lys Pro His Tyr Phe Asn Tyr
 50                  55                  60

Gly Val Ala Asn Arg Glu Ser Gly Arg Arg Ile Ser Glu Arg Thr Leu

```
                65                  70                  75                  80
        Phe Glu Ile Gly Ser Val Ser Lys Thr Phe Thr Ala Thr Leu Gly Thr
                        85                  90                  95

Tyr Ala Val Val Lys Gly Gly Phe Arg Leu Asp Asp Lys Val Ser Gln
                        100                 105                 110

His Ala Pro Trp Leu Gln Asn Ser Ala Phe Asp Arg Val Thr Met Ala
                        115                 120                 125

Gln Leu Ala Thr Tyr Ser Ala Gly Gly Leu Pro Leu Gln Phe Pro Asp
                130                 135                 140

Ala Val Asp Ser Asn Glu Arg Met Arg Gln Tyr Tyr Arg Gln Trp Ser
        145                 150                 155                 160

Pro Leu Tyr Ala Ala Gly Thr His Arg Glu Tyr Ser Asn Pro Ser Ile
                        165                 170                 175

Gly Leu Phe Gly His Leu Ala Ala Ser Thr Leu Gly Pro Phe Arg
                        180                 185                 190

Gln Leu Met Ser Gln Thr Leu Leu Pro Lys Leu Asp Leu Gln His Thr
                        195                 200                 205

Tyr Leu Glu Val Pro Asp Ala Ala Met Val Asp Tyr Ala Tyr Gly Tyr
                210                 215                 220

Ser Lys Glu Asp Lys Pro Val Arg Val Asn Pro Gly Val Leu Ala Asp
        225                 230                 235                 240

Glu Ala Tyr Gly Ile Lys Thr Ser Ala Ala Asp Leu Ile Lys Phe Val
                        245                 250                 255

Gly Ala Asn Met Thr Gly Ser Gly Asp Lys Ala Val Gln Gln Ala Leu
                        260                 265                 270

Ala Met Thr Arg Thr Gly Phe Tyr Ser Val Gly Glu Met Thr Gln Gly
                        275                 280                 285

Leu Gly Trp Glu Ser Tyr Ala Tyr Pro Val Thr Glu Gln Ala Leu Leu
                        290                 295                 300

Ala Gly Asn Ser Pro Ala Val Ser Phe Lys Ala Asn Pro Val Lys Pro
        305                 310                 315                 320

Phe Val Ala Pro Arg Val Met Gly Asn Glu Arg Leu Tyr Asn Lys Thr
                        325                 330                 335

Gly Ser Thr Asn Gly Phe Gly Ala Tyr Val Val Phe Val Pro Ala Arg
                        340                 345                 350

Gly Val Gly Ile Val Met Leu Ala Asn Arg Asn Tyr Pro Ile Glu Ala
                        355                 360                 365

Arg Val Lys Ala Ala Tyr Ala Ile Met Arg His Leu Ala Pro Gly Gly
                        370                 375                 380

Ser Leu Glu His His His His His His
        385                 390

<210> SEQ ID NO 56
<211> LENGTH: 388
<212> TYPE: PRT
<213> ORGANISM: Escherichia coli

<400> SEQUENCE: 56

Met Phe Lys Thr Thr Leu Cys Ala Leu Leu Ile Thr Ala Ser Cys Ser
        1               5                   10                  15

Thr Phe Ala Ala Pro Gln Gln Ile Asn Asp Ile Val His Arg Thr Ile
                        20                  25                  30

Thr Pro Leu Ile Glu Gln Gln Lys Ile Pro Gly Met Ala Val Ala Val
                        35                  40                  45
```

```
Ile Tyr Gln Gly Lys Pro Tyr Phe Thr Trp Gly Tyr Ala Asp Ile
 50                  55                  60

Ala Lys Lys Gln Pro Val Thr Gln Gln Thr Leu Phe Glu Leu Gly Ser
 65                  70                  75                  80

Val Ser Lys Thr Phe Thr Gly Val Leu Gly Gly Asp Ala Ile Ala Arg
                 85                  90                  95

Gly Glu Ile Lys Leu Ser Asp Pro Thr Thr Lys Tyr Trp Pro Glu Leu
            100                 105                 110

Thr Ala Lys Gln Trp Asn Gly Ile Thr Leu Leu His Leu Ala Thr Tyr
            115                 120                 125

Thr Ala Gly Gly Leu Pro Leu Gln Val Pro Asp Glu Val Lys Ser Ser
130                 135                 140

Ser Asp Leu Leu Arg Phe Tyr Gln Asn Trp Gln Pro Ala Trp Ala Pro
145                 150                 155                 160

Gly Thr Gln Arg Leu Tyr Ala Asn Ser Ser Ile Gly Leu Phe Gly Ala
                165                 170                 175

Leu Ala Val Lys Pro Ser Gly Leu Ser Phe Glu Gln Ala Met Gln Thr
            180                 185                 190

Arg Val Phe Gln Pro Leu Lys Leu Asn His Thr Trp Ile Asn Val Pro
            195                 200                 205

Pro Ala Glu Glu Lys Asn Tyr Ala Trp Gly Tyr Arg Glu Gly Lys Ala
210                 215                 220

Val His Val Ser Pro Gly Ala Leu Asp Ala Glu Ala Tyr Gly Val Lys
225                 230                 235                 240

Ser Thr Ile Glu Asp Met Ala Arg Trp Val Gln Ser Asn Leu Lys Pro
                245                 250                 255

Leu Asp Ile Asn Glu Lys Thr Leu Gln Gln Gly Ile Gln Leu Ala Gln
            260                 265                 270

Ser Arg Tyr Trp Gln Thr Gly Asp Met Tyr Gln Gly Leu Gly Trp Glu
            275                 280                 285

Met Leu Asp Trp Pro Val Asn Pro Asp Ser Ile Ile Asn Gly Ser Asp
290                 295                 300

Asn Lys Ile Ala Leu Ala Ala Arg Pro Val Lys Ala Ile Thr Pro Pro
305                 310                 315                 320

Thr Pro Ala Val Arg Ala Ser Trp Val His Lys Thr Gly Ala Thr Gly
                325                 330                 335

Gly Phe Gly Ser Tyr Val Ala Phe Ile Pro Glu Lys Glu Leu Gly Ile
            340                 345                 350

Val Met Leu Ala Asn Lys Asn Tyr Pro Asn Pro Ala Arg Val Asp Ala
            355                 360                 365

Ala Trp Gln Ile Leu Asn Ala Leu Gln Gly Gly Ser Leu Glu His His
370                 375                 380

His His His His
385

<210> SEQ ID NO 57
<211> LENGTH: 347
<212> TYPE: PRT
<213> ORGANISM: Scheffersomyces stipitis

<400> SEQUENCE: 57

Met Ser Lys Tyr Lys Ile Leu Asp Ser His Ile His Leu Tyr Ser Leu
 1                   5                  10                  15

Ala Asn Ile Pro Leu Leu His Trp Asp Glu Gly Asn Pro Leu His Gly
                 20                  25                  30
```

```
Asn Arg Arg Leu Asp Glu Tyr Ile Glu Asn Ser Gln Ser Thr Gln Phe
            35                  40                  45

Asp Val Glu Gly Val Val Trp Ile Glu Cys Asp Ala Lys Ile Asp Leu
 50                  55                  60

Thr Gln Gly Leu Lys Gly Leu Glu Asn Pro Ile Glu Glu Tyr Leu Tyr
 65                  70                  75                  80

Ile Cys Arg Asn Ile Asn Gly Lys Leu Leu Pro Glu Glu Gly Val Ser
                 85                  90                  95

Thr Pro Phe Lys Arg Arg Leu Ile Lys Ala Met Ile Pro Phe Ala Pro
            100                 105                 110

Met Pro Leu Gly Ser Ala Gly Val Glu Glu Tyr Val Lys Ala Leu Lys
            115                 120                 125

Thr Arg Asn Ser Ser Glu Phe His Leu Val Lys Gly Phe Arg Tyr Leu
130                 135                 140

Ile Gln Asp Lys Pro Pro Leu Thr Ile Ser Asp Pro His Phe Val Ser
145                 150                 155                 160

Ser Phe Gln Trp Leu Asp Ser Asn Gly Tyr Val Phe Asp Leu Gly Ile
                165                 170                 175

Asp Met Arg Ser Gly Gly Leu Trp Gln Phe Lys Glu Thr Leu Glu Val
            180                 185                 190

Phe Lys Lys Val Pro Asn Leu Lys Tyr Ile Ile Asn His Leu Thr Lys
            195                 200                 205

Pro Cys Leu Asp Phe Asp Pro Glu Thr Ile Asp Ser Asn Pro Asp Phe
            210                 215                 220

Leu Ser Trp Lys Arg Leu Val Thr Glu Met Tyr Ile Thr Thr Pro Asn
225                 230                 235                 240

Ser Tyr Met Lys Leu Ser Gly Gly Phe Ser Glu Val Glu Gln Asp Val
                245                 250                 255

Ala Leu Asp Val Thr Ser Thr Ser Arg His Val Tyr Pro Trp Phe Lys
            260                 265                 270

Val Val Tyr Glu Leu Trp Gly Pro Glu Arg Thr Ile Phe Ala Ser Asn
            275                 280                 285

Trp Pro Val Cys Ala Ile Pro Ala Gly Gln Asn Leu Thr Glu Lys Trp
            290                 295                 300

Phe Gln Val Cys Glu Thr Leu Phe Asp Ser Ile Gly Met Asp Glu Asp
305                 310                 315                 320

Thr Arg Arg Lys Ile Tyr Tyr Ser Asn Ala Phe Lys Ala Tyr Asn Ile
                325                 330                 335

Gly Gly Ser Leu Glu His His His His His
            340                 345

<210> SEQ ID NO 58
<211> LENGTH: 452
<212> TYPE: PRT
<213> ORGANISM: Escherichia coli

<400> SEQUENCE: 58

Met Ser Glu Ile Ser Arg Gln Glu Phe Gln Arg Arg Gln Ala Leu
1               5                   10                  15

Val Glu Gln Met Gln Pro Gly Ser Ala Ala Leu Ile Phe Ala Ala Pro
            20                  25                  30

Glu Val Thr Arg Ser Ala Asp Ser Glu Tyr Pro Tyr Arg Gln Asn Ser
            35                  40                  45

Asp Phe Trp Tyr Phe Thr Gly Phe Asn Glu Pro Glu Ala Val Leu Val
```

```
                  50                  55                  60

Leu Ile Lys Ser Asp Asp Thr His Asn His Ser Val Leu Phe Asn Arg
 65                  70                  75                  80

Val Arg Asp Leu Thr Ala Glu Ile Trp Phe Gly Arg Arg Leu Gly Gln
                     85                  90                  95

Asp Ala Ala Pro Glu Lys Leu Gly Val Asp Arg Ala Leu Ala Phe Ser
                100                 105                 110

Glu Ile Asn Gln Gln Leu Tyr Gln Leu Leu Asn Gly Leu Asp Val Val
                115                 120                 125

Tyr His Ala Gln Gly Glu Tyr Ala Tyr Ala Asp Val Ile Val Asn Ser
                130                 135                 140

Ala Leu Glu Lys Leu Arg Lys Gly Ser Arg Gln Asn Leu Thr Ala Pro
145                 150                 155                 160

Ala Thr Met Ile Asp Trp Arg Pro Val His Glu Met Arg Leu Phe
                     165                170                  175

Lys Ser Pro Glu Glu Ile Ala Val Leu Arg Arg Ala Gly Glu Ile Thr
                180                  185                190

Ala Met Ala His Thr Arg Ala Met Glu Lys Cys Arg Pro Gly Met Phe
                195                  200                205

Glu Tyr His Leu Glu Gly Glu Ile His His Glu Phe Asn Arg His Gly
                210                  215                220

Ala Arg Tyr Pro Ser Tyr Asn Thr Ile Val Gly Ser Glu Asn Gly
225                 230                  235                240

Cys Ile Leu His Tyr Thr Glu Asn Glu Cys Glu Met Arg Asp Gly Asp
                     245                250                 255

Leu Val Leu Ile Asp Ala Gly Cys Glu Tyr Lys Gly Tyr Ala Gly Asp
                260                  265                270

Ile Thr Arg Thr Phe Pro Val Asn Gly Lys Phe Thr Gln Ala Gln Arg
                275                  280                285

Glu Ile Tyr Asp Ile Val Leu Glu Ser Leu Gly Thr Ser Leu Arg Leu
                290                  295                300

Tyr Arg Pro Gly Thr Ser Ile Leu Glu Val Thr Gly Glu Val Val Arg
305                 310                  315                320

Ile Met Val Ser Gly Leu Val Lys Leu Gly Ile Leu Lys Gly Asp Val
                325                  330                335

Asp Glu Leu Ile Ala Gln Asn Ala His Arg Pro Phe Phe Met His Gly
                340                  345                350

Leu Ser His Trp Leu Gly Leu Asp Val His Asp Val Gly Val Tyr Gly
                355                  360                365

Gln Asp Arg Ser Arg Ile Leu Glu Pro Gly Met Val Leu Thr Val Glu
                370                  375                380

Pro Gly Leu Tyr Ile Ala Pro Asp Ala Glu Pro Glu Gln Tyr Arg
385                 390                  395                400

Gly Ile Gly Ile Arg Ile Glu Asp Asp Ile Val Ile Thr Glu Thr Gly
                     405                410                 415

Asn Glu Asn Leu Thr Ala Ser Val Val Lys Lys Pro Glu Glu Ile Glu
                420                  425                430

Ala Leu Met Val Ala Ala Arg Lys Gln Gly Gly Ser Leu Glu His His
                435                  440                445

His His His His
    450

<210> SEQ ID NO 59
```

```
<211> LENGTH: 302
<212> TYPE: PRT
<213> ORGANISM: Caulobacter vibrioides

<400> SEQUENCE: 59
```

Met Asn Ala Val Thr Cys Val Trp Asp Leu Lys Ala Thr Leu Gly Glu
1               5                   10                  15

Gly Pro Ile Trp Tyr Asp Asp Ser Leu Trp Phe Val Asp Ile Lys Ser
            20                  25                  30

His Lys Ile His Asn Tyr Asn Pro Ala Thr Asp Glu Arg Phe Ser Phe
        35                  40                  45

Asp Ala Pro Glu Pro Val Thr Phe Ile Ala Pro Leu Ala Pro Asn Ala
    50                  55                  60

Arg Ala Gly Phe Val Val Gly Leu Lys Ser Gly Leu His Arg Phe His
65                  70                  75                  80

Pro Val Met Gly Gly Phe Lys Pro Leu Ile Gln Val Glu Ser Ala Glu
                85                  90                  95

Leu Asn Asn Arg Pro Asn Asp Ala Thr Val Asp His Gly Gly Arg Leu
            100                 105                 110

Trp Phe Gly Thr Met His Asp Asp Glu Glu Ala Lys Ser Gly Ser Leu
        115                 120                 125

Tyr Arg Met Asp Ser Thr Gly Val Ala Arg Met Asp Lys Asp Ile Cys
    130                 135                 140

Ile Thr Asn Gly Pro Cys Val Ser Pro Asp Gly Lys Thr Leu Tyr His
145                 150                 155                 160

Thr Asp Thr Leu Glu Lys Ile Ile Trp Ala Tyr Asp Leu Ala Glu Asp
                165                 170                 175

Gly Thr Leu Ser Asn Lys Arg Gly Phe Val Asn Phe Gln Gly Glu Asn
            180                 185                 190

Ala Val Tyr Pro Asp Gly Ser Val Asp Ser Glu Gly Tyr Leu Trp
    195                 200                 205

Thr Ala Leu Trp Gly Gly Phe Gly Val Val Arg Ile Ser Pro Ala Gly
    210                 215                 220

Glu Leu Val Ala Arg Ile Glu Leu Pro Ala Pro Asn Val Thr Lys Pro
225                 230                 235                 240

Cys Phe Gly Gly Pro Asp Leu Lys Thr Leu Tyr Phe Thr Thr Ala Arg
                245                 250                 255

Lys Gly Leu Ser Asp Glu Thr Leu Ala Gln Tyr Pro Leu Ser Gly Gly
            260                 265                 270

Leu Phe Gly Val Arg Val Asp Val Ala Gly Gln Pro Gln His Glu Val
        275                 280                 285

Arg Leu Val Gly Gly Ser Leu Glu His His His His His
    290                 295                 300

```
<210> SEQ ID NO 60
<211> LENGTH: 230
<212> TYPE: PRT
<213> ORGANISM: Pelagibacterium halotolerans

<400> SEQUENCE: 60
```

Met Thr Glu Pro Val Lys Leu Ser Gly Pro Met Leu Pro Ala Val Ser
1               5                   10                  15

Gly Ala Ala Lys Ser Leu Val Val Leu Leu His Gly Tyr Gly Ser Asp
            20                  25                  30

Gly Arg Asp Leu Ile Ala Leu Gly Gln Phe Trp Arg Asp Ser Phe Pro
        35                  40                  45

```
Asp Thr Met Phe Val Ala Pro Asn Ala Pro His Val Cys Gly Gly Asn
     50                  55                  60

Pro Phe Gly Tyr Glu Trp Phe Pro Leu Asp Leu Glu Arg Asp Arg Thr
 65                  70                  75                  80

Leu Ala Arg Leu Ala Gly Ala Glu Thr Ala His Pro Val Leu Asp Ala
                 85                  90                  95

Phe Leu Ala Asp Leu Trp Ala Gln Thr Gly Leu Gly Pro Ala Asp Thr
                100                 105                 110

Ile Leu Val Gly Phe Ser Gln Gly Ala Met Met Ala Leu Tyr Thr Gly
            115                 120                 125

Leu Arg Leu Pro Glu Pro Leu Lys Ala Ile Ile Ala Phe Ser Gly Leu
        130                 135                 140

Ile Val Ala Pro Glu Lys Leu Glu Ala Glu Ile Ala Ser Lys Pro Pro
145                 150                 155                 160

Val Leu Leu Ile His Gly Asp Leu Asp Val Val Pro Val Ile Gly
                165                 170                 175

Ser Glu Thr Ala Leu Pro Lys Leu Ile Asp Leu Gly Ile Asp Ala Arg
                180                 185                 190

Leu His Ile Ser Gln Gly Ser Gly His Thr Ile Ala Gln Asp Gly Leu
            195                 200                 205

Asp Thr Ala Thr Ala Phe Leu Arg Glu Ile Leu Gly Gly Ser Leu Glu
        210                 215                 220

His His His His His His
225                 230

<210> SEQ ID NO 61
<211> LENGTH: 308
<212> TYPE: PRT
<213> ORGANISM: Rhodococcus erythropolis

<400> SEQUENCE: 61

Met Ser Ala Thr Asp Thr Ala Arg Ala Lys Glu Leu Leu Ala Ser Leu
 1               5                  10                  15

Val Ser Met Pro Asp Ala Thr Ile Asp Asp Phe Arg Ala Leu Tyr Glu
                20                  25                  30

Gln Val Cys Ala Thr Phe Glu Leu Pro Asp Asp Ala Gln Val Glu Pro
             35                  40                  45

Val Asp Ala Asn Gly Ala Asp Ala Leu Trp Val Ser Ala Pro Gly Val
     50                  55                  60

Ser Ala Asp Thr Val Ala Val Val His Gly Gly Gly Phe Thr Met
 65                  70                  75                  80

Gly Ser Ala His Gly Tyr Arg Glu Leu Gly Tyr Arg Leu Ser Lys Ser
                 85                  90                  95

Gly Asn Leu Arg Ala Leu Val Val Asp Tyr Arg Leu Ala Pro Glu Ser
            100                 105                 110

Pro Phe Pro Ala Pro Val Asp Asp Val Ala Ala Tyr Arg Tyr Ala
        115                 120                 125

Arg Ser Leu Asp Gly Val Glu Asn Val Phe Leu Val Gly Asp Ser Ala
        130                 135                 140

Gly Gly Gly Ile Ala Met Ser Ala Leu Ile Thr Leu Arg Asp Ala Gly
145                 150                 155                 160

Glu Gln Leu Pro Asp Ala Ala Val Val Leu Ser Pro Leu Val Asp Leu
                165                 170                 175

Ala Gly Glu Ser Pro Ser Leu Val Asp Arg Ala His Leu Asp Pro Leu
```

```
            180                 185                 190
Pro Ala Ala Val Leu Val Asn Gly Met Gly Gly Leu Tyr Leu Asn Gly
            195                 200                 205

Leu Asp Val Arg His Pro Val Ala Ser Pro Met His Gly Asp Leu Thr
            210                 215                 220

Gly Leu Pro Ala Thr Leu Val Leu Val Gly Thr Asp Glu Gly Leu His
225                 230                 235                 240

Asp Asp Ser Thr Arg Leu Val Asp Lys Leu Lys Ala Ala Asp Val Glu
                    245                 250                 255

Val Gln Leu Glu Ile Gly Glu Gly Leu Pro His Ile Trp Pro Ile Phe
                260                 265                 270

Ser Phe His Pro Asp Ala Val Ala Ala Thr Asp Arg Ile Gly Glu Phe
            275                 280                 285

Leu Arg Ser His Val Ala Ala Pro Arg Gly Gly Ser Leu Glu His His
        290                 295                 300

His His His His
305

<210> SEQ ID NO 62
<211> LENGTH: 311
<212> TYPE: PRT
<213> ORGANISM: Azospirillum brasilense

<400> SEQUENCE: 62

Met Gln Gln Ile His Pro Ala Gly Gln Ala Thr Leu Leu Ala Asp Thr
1               5                   10                  15

Arg Asn Thr Leu Gly Glu Gly Ala Thr Trp Cys Asp Arg Thr Arg Ala
            20                  25                  30

Leu Tyr Trp Val Asp Ile Glu Gly Ala Gln Leu Trp Arg Cys Arg Ala
        35                  40                  45

Asp Gly Ser Asp Leu Thr Pro Trp Pro Met Pro Glu Arg Leu Ala Cys
    50                  55                  60

Phe Ala Leu Thr Asp Asp Pro Asp Val Leu Leu Val Gly Leu Ala Thr
65                  70                  75                  80

His Leu Ala Phe Phe Asp Leu Arg Ser Gly Ala Phe Thr Arg Ile Val
                85                  90                  95

Glu Val Glu Pro Glu Leu Pro Thr Arg Leu Asn Asp Gly Arg Cys Asp
            100                 105                 110

Gly Ser Gly Ala Phe Val Phe Gly Met Lys Asp Glu Gly Ala Glu Pro
        115                 120                 125

Pro Arg Ala Val Gly Gly Phe Tyr Arg Leu Asn Ala Asp Leu Thr Leu
    130                 135                 140

Glu Arg Leu Ala Leu Pro Pro Ala Ala Ile Ala Asn Ser Ile Gly Phe
145                 150                 155                 160

Ser Pro Asp Gly Ser Lys Met Tyr Phe Cys Asp Ser Leu Val Arg Glu
                165                 170                 175

Ile Phe Val Cys Asp Tyr Arg Pro Gly Gly Glu Val Ala Asn Val Arg
            180                 185                 190

Pro Phe Ala Arg Leu Thr Asp Pro Asp Gly Pro Asp Gly Ser Ile
        195                 200                 205

Val Asp Arg Asp Gly Gly Leu Trp Asn Ala Gln Trp Gly Gly Arg Arg
    210                 215                 220

Val Val Arg Tyr Gly Pro Asp Gly Val Glu Thr Asp Arg Val Ala Val
225                 230                 235                 240
```

```
Pro Thr Ala Gln Pro Ser Cys Thr Ala Leu Asp Gly Glu Gly Arg Leu
                245                 250                 255

Tyr Val Thr Ser Ala Arg Val Gly Leu Ser Asp Asp Ala Leu Ala Asp
            260                 265                 270

Asp Pro His Ala Gly Gly Val Phe Val Ala Gln Thr Arg His Ala Gly
        275                 280                 285

Met Ala Thr Ala Arg Phe Ala Gly Thr Pro Arg Gly Gly Gly Ser Leu
290                 295                 300

Glu His His His His His His
305                 310

<210> SEQ ID NO 63
<211> LENGTH: 1088
<212> TYPE: PRT
<213> ORGANISM: Acetivibrio thermocellus

<400> SEQUENCE: 63

Met Lys Asn Lys Arg Val Leu Ala Lys Ile Thr Ala Leu Val Val Leu
1               5                   10                  15

Leu Gly Val Phe Phe Val Leu Pro Ser Asn Ile Ser Gln Leu Tyr Ala
            20                  25                  30

Asp Tyr Glu Val Val His Asp Thr Phe Glu Val Asn Phe Asp Gly Trp
        35                  40                  45

Cys Asn Leu Gly Val Asp Thr Tyr Leu Thr Ala Val Glu Asn Glu Gly
    50                  55                  60

Asn Asn Gly Thr Arg Gly Met Met Val Ile Asn Arg Ser Ser Ala Ser
65                  70                  75                  80

Asp Gly Ala Tyr Ser Glu Lys Gly Phe Tyr Leu Asp Gly Gly Val Glu
                85                  90                  95

Tyr Lys Tyr Ser Val Phe Val Lys His Asn Gly Thr Gly Thr Glu Thr
            100                 105                 110

Phe Lys Leu Ser Val Ser Tyr Leu Asp Ser Glu Thr Glu Glu Glu Asn
        115                 120                 125

Lys Glu Val Ile Ala Thr Lys Asp Val Val Ala Gly Glu Trp Thr Glu
130                 135                 140

Ile Ser Ala Lys Tyr Lys Ala Pro Lys Thr Ala Val Asn Ile Thr Leu
145                 150                 155                 160

Ser Ile Thr Thr Asp Ser Thr Val Asp Phe Ile Phe Asp Asp Val Thr
                165                 170                 175

Ile Thr Arg Lys Gly Met Ala Glu Ala Asn Thr Val Tyr Ala Ala Asn
            180                 185                 190

Ala Val Leu Lys Asp Met Tyr Ala Asn Tyr Phe Arg Val Gly Ser Val
        195                 200                 205

Leu Asn Ser Gly Thr Val Asn Asn Ser Ile Lys Ala Leu Ile Leu
210                 215                 220

Arg Glu Phe Asn Ser Ile Thr Cys Glu Asn Glu Met Lys Pro Asp Ala
225                 230                 235                 240

Thr Leu Val Gln Ser Gly Ser Thr Asn Thr Asn Ile Arg Val Ser Leu
                245                 250                 255

Asn Arg Ala Ala Ser Ile Leu Asn Phe Cys Ala Gln Asn Asn Ile Ala
            260                 265                 270

Val Arg Gly His Thr Leu Val Trp His Ser Gln Thr Pro Gln Trp Phe
        275                 280                 285

Phe Lys Asp Asn Phe Gln Asp Asn Gly Asn Trp Val Ser Gln Ser Val
290                 295                 300
```

```
Met Asp Gln Arg Leu Glu Ser Tyr Ile Lys Asn Met Phe Ala Glu Ile
305                 310                 315                 320

Gln Arg Gln Tyr Pro Ser Leu Asn Leu Tyr Ala Tyr Asp Val Val Asn
            325                 330                 335

Glu Ala Val Ser Asp Asp Ala Asn Arg Thr Arg Tyr Tyr Gly Gly Ala
            340                 345                 350

Arg Glu Pro Gly Tyr Gly Asn Gly Arg Ser Pro Trp Val Gln Ile Tyr
            355                 360                 365

Gly Asp Asn Lys Phe Ile Glu Lys Ala Phe Thr Tyr Ala Arg Lys Tyr
            370                 375                 380

Ala Pro Ala Asn Cys Lys Leu Tyr Tyr Asn Asp Tyr Asn Glu Tyr Trp
385                 390                 395                 400

Asp His Lys Arg Asp Cys Ile Ala Ser Ile Cys Ala Asn Leu Tyr Asn
            405                 410                 415

Lys Gly Leu Leu Asp Gly Val Gly Met Gln Ser His Ile Asn Ala Asp
            420                 425                 430

Met Asn Gly Phe Ser Gly Ile Gln Asn Tyr Lys Ala Ala Leu Gln Lys
            435                 440                 445

Tyr Ile Asn Ile Gly Cys Asp Val Gln Ile Thr Glu Leu Asp Ile Ser
450                 455                 460

Thr Glu Asn Gly Lys Phe Ser Leu Gln Gln Ala Asp Lys Tyr Lys
465                 470                 475                 480

Ala Val Phe Gln Ala Ala Val Asp Ile Asn Arg Thr Ser Ser Lys Gly
            485                 490                 495

Lys Val Thr Ala Val Cys Val Trp Gly Pro Asn Asp Ala Asn Thr Trp
            500                 505                 510

Leu Gly Ser Gln Asn Ala Pro Leu Leu Phe Asn Ala Asn Asn Gln Pro
            515                 520                 525

Lys Pro Ala Tyr Asn Ala Val Ala Ser Ile Ile Pro Gln Ser Glu Trp
            530                 535                 540

Gly Asp Gly Asn Asn Pro Ala Gly Gly Gly Gly Lys Pro Glu
545                 550                 555                 560

Glu Pro Asp Ala Asn Gly Tyr Tyr Tyr His Asp Thr Phe Glu Gly Ser
            565                 570                 575

Val Gly Gln Trp Thr Ala Arg Gly Pro Ala Glu Val Leu Leu Ser Gly
            580                 585                 590

Arg Thr Ala Tyr Lys Gly Ser Glu Ser Leu Leu Val Arg Asn Arg Thr
            595                 600                 605

Ala Ala Trp Asn Gly Ala Gln Arg Ala Leu Asn Pro Arg Thr Phe Val
            610                 615                 620

Pro Gly Asn Thr Tyr Cys Phe Ser Val Val Ala Ser Phe Ile Glu Gly
625                 630                 635                 640

Ala Ser Ser Thr Thr Phe Cys Met Lys Leu Gln Tyr Val Asp Gly Ser
            645                 650                 655

Gly Thr Gln Arg Tyr Asp Thr Ile Asp Met Lys Thr Val Gly Pro Asn
            660                 665                 670

Gln Trp Val His Leu Tyr Asn Pro Gln Tyr Arg Ile Pro Ser Asp Ala
            675                 680                 685

Thr Asp Met Tyr Val Tyr Val Glu Thr Ala Asp Asp Thr Ile Asn Phe
            690                 695                 700

Tyr Ile Asp Glu Ala Ile Gly Ala Val Ala Gly Thr Val Ile Glu Gly
705                 710                 715                 720
```

| | | | | | | | | | | | |
|---|---|---|---|---|---|---|---|---|---|---|---|
|Pro|Ala|Pro|Gln|Pro|Thr|Gln|Pro|Pro|Val|Leu|Leu|Gly|Asp|Val|Asn|
| | | |725| | | |730| | | |735|

Pro Ala Pro Gln Pro Thr Gln Pro Pro Val Leu Leu Gly Asp Val Asn
             725         730            735

Gly Asp Gly Thr Ile Asn Ser Thr Asp Leu Thr Met Leu Lys Arg Ser
       740            745            750

Val Leu Arg Ala Ile Thr Leu Thr Asp Ala Lys Ala Arg Ala Asp
    755             760            765

Val Asp Lys Asn Gly Ser Ile Asn Ser Thr Asp Val Leu Leu Ser
770                 775                 780

Arg Tyr Leu Leu Arg Val Ile Asp Lys Phe Pro Val Ala Glu Asn Pro
785                 790                 795                 800

Ser Ser Ser Phe Lys Tyr Glu Ser Ala Val Gln Tyr Arg Pro Ala Pro
            805                 810                 815

Asp Ser Tyr Leu Asn Pro Cys Pro Gln Ala Gly Arg Ile Val Lys Glu
            820                 825                 830

Thr Tyr Thr Gly Ile Asn Gly Thr Lys Ser Leu Asn Val Tyr Leu Pro
            835                 840                 845

Tyr Gly Tyr Asp Pro Asn Lys Lys Tyr Asn Ile Phe Tyr Leu Met His
850                 855                 860

Gly Gly Gly Glu Asn Glu Asn Thr Ile Phe Ser Asn Asp Val Lys Leu
865                 870                 875                 880

Gln Asn Ile Leu Asp His Ala Ile Met Asn Gly Glu Leu Gly Pro Leu
            885                 890                 895

Ile Val Val Thr Pro Thr Phe Asn Gly Gly Asn Cys Thr Ala Gln Asn
            900                 905                 910

Phe Tyr Gln Glu Phe Arg Gln Asn Val Ile Pro Phe Val Glu Ser Lys
            915                 920                 925

Tyr Ser Thr Tyr Ala Glu Ser Thr Thr Pro Gln Gly Ile Ala Ala Ser
930                 935                 940

Arg Met His Arg Gly Phe Gly Phe Ser Met Gly Gly Leu Thr Thr
945                 950                 955                 960

Trp Tyr Val Met Val Asn Cys Leu Asp Tyr Val Ala Tyr Phe Met Pro
            965                 970                 975

Leu Ser Gly Asp Tyr Trp Tyr Gly Asn Ser Pro Gln Asp Lys Ala Asn
            980                 985                 990

Ser Ile Ala Glu Ala Ile Asn Arg Ser Gly Leu Ser Lys Arg Glu Tyr
            995                 1000                 1005

Phe Val Phe Ala Ala Thr Gly Ser Asp His Ile Ala Tyr Ala Asn
    1010                 1015                 1020

Met Asn Pro Gln Ile Glu Ala Met Lys Ala Leu Pro His Phe Asp
    1025                 1030                 1035

Tyr Thr Ser Asp Phe Ser Lys Gly Asn Phe Tyr Phe Leu Val Ala
    1040                 1045                 1050

Pro Gly Ala Thr His Trp Trp Gly Tyr Val Arg His Tyr Ile Tyr
    1055                 1060                 1065

Asp Ala Leu Pro Tyr Phe Phe His Glu Gly Gly Ser Leu Glu His
    1070                 1075                 1080

His His His His His
    1085

<210> SEQ ID NO 64
<211> LENGTH: 316
<212> TYPE: PRT
<213> ORGANISM: Xanthomonas campestris

<400> SEQUENCE: 64

```
Met Asp Ser His Cys Arg Val Arg Pro Ala Gly Pro Ala Val Pro Ala
1               5                   10                  15

Asp Cys Asp Pro Pro Arg Ile Thr His Ala Ala Leu Ala Ala Arg Leu
            20                  25                  30

Gly Asp Ala Arg Leu Leu Thr Leu Tyr Asp Gln Ala Thr Trp Ser Glu
        35                  40                  45

Gly Pro Ala Trp Trp Glu Ala Gln Arg Thr Leu Val Trp Ser Asp Leu
    50                  55                  60

Val Gly Arg Arg Val Leu Gly Trp Arg Glu Asp Gly Thr Val Asp Val
65                  70                  75                  80

Leu Leu Asp Ala Thr Ala Phe Thr Asn Gly Asn Ala Val Asp Ala Gln
                85                  90                  95

Gln Arg Leu Val His Cys Glu His Gly Arg Arg Ala Ile Thr Arg Ser
            100                 105                 110

Asp Ala Asp Gly Gln Ala His Leu Leu Val Gly Arg Tyr Ala Gly Lys
        115                 120                 125

Arg Leu Asn Ser Pro Asn Asp Leu Ile Val Ala Arg Asp Gly Ala Ile
    130                 135                 140

Trp Phe Thr Asp Pro Pro Phe Gly Leu Arg Lys Pro Ser Gln Gly Cys
145                 150                 155                 160

Pro Ala Asp Pro Glu Leu Ala His His Ser Val Tyr Arg Leu Pro Pro
                165                 170                 175

Asp Gly Ser Pro Leu Gln Arg Met Ala Asp Leu Asp His Pro Asn Gly
            180                 185                 190

Leu Ala Phe Ser Pro Asp Glu Gln Thr Leu Tyr Val Ser Gln Thr Pro
        195                 200                 205

Glu Gln Gly His Gly Ser Val Glu Ile Thr Ala Phe Ala Trp Arg Asp
    210                 215                 220

Gly Ala Leu His Asp Arg Arg His Phe Ala Ser Val Pro Asp Gly Leu
225                 230                 235                 240

Pro Asp Gly Phe Cys Val Asp Arg Gly Gly Trp Leu Trp Ser Ser Ser
                245                 250                 255

Gly Thr Gly Val Cys Val Phe Asp Ser Asp Gly Gln Leu Leu Gly His
            260                 265                 270

Ile Pro Thr Pro Gly Thr Ala Ser Asn Cys Thr Phe Asp Gln Ala Gln
        275                 280                 285

Gln Arg Leu Phe Ile Thr Gly Gly Pro Cys Leu Trp Met Leu Pro Leu
    290                 295                 300

Pro Gly Gly Ser Leu Glu His His His His His
305                 310                 315

<210> SEQ ID NO 65
<211> LENGTH: 292
<212> TYPE: PRT
<213> ORGANISM: Aspergillus niger

<400> SEQUENCE: 65

Met Lys Gln Phe Ser Ala Lys Tyr Ala Leu Ile Leu Leu Ala Thr Ala
1               5                   10                  15

Gly Gln Ala Leu Ala Ala Ser Thr Gln Gly Ile Ser Glu Asp Leu Tyr
            20                  25                  30

Asn Arg Leu Val Glu Met Ala Thr Ile Ser Gln Ala Ala Tyr Ala Asp
        35                  40                  45

Leu Cys Asn Ile Pro Ser Thr Ile Ile Lys Gly Glu Lys Ile Tyr Asn
```

```
                50                  55                  60
Ala Gln Thr Asp Ile Asn Gly Trp Ile Leu Arg Asp Asp Thr Ser Lys
 65                  70                  75                  80

Glu Ile Ile Thr Val Phe Arg Gly Thr Gly Ser Asp Thr Asn Leu Gln
                 85                  90                  95

Leu Asp Thr Asn Tyr Thr Leu Thr Pro Phe Asp Thr Leu Pro Gln Cys
            100                 105                 110

Asn Asp Cys Glu Val His Gly Gly Tyr Tyr Ile Gly Trp Ile Ser Val
            115                 120                 125

Gln Asp Gln Val Glu Ser Leu Val Lys Gln Gln Ala Ser Gln Tyr Pro
        130                 135                 140

Asp Tyr Ala Leu Thr Val Thr Gly His Ser Leu Gly Ala Ser Met Ala
145                 150                 155                 160

Ala Leu Thr Ala Ala Gln Leu Ser Ala Thr Tyr Asp Asn Val Arg Leu
                165                 170                 175

Tyr Thr Phe Gly Glu Pro Arg Ser Gly Asn Gln Ala Phe Ala Ser Tyr
            180                 185                 190

Met Asn Asp Ala Phe Gln Val Ser Ser Pro Glu Thr Thr Gln Tyr Phe
        195                 200                 205

Arg Val Thr His Ser Asn Asp Gly Ile Pro Asn Leu Pro Pro Ala Asp
    210                 215                 220

Glu Gly Tyr Ala His Gly Gly Val Glu Tyr Trp Ser Val Asp Pro Tyr
225                 230                 235                 240

Ser Ala Gln Asn Thr Phe Val Cys Thr Gly Asp Glu Val Gln Cys Cys
                245                 250                 255

Glu Ala Gln Gly Gly Gln Gly Val Asn Asp Ala His Thr Thr Tyr Phe
            260                 265                 270

Gly Met Thr Ser Gly Ala Cys Thr Trp Gly Gly Ser Leu Glu His His
        275                 280                 285

His His His His
    290

<210> SEQ ID NO 66
<211> LENGTH: 412
<212> TYPE: PRT
<213> ORGANISM: Gibberella intermedia

<400> SEQUENCE: 66

Met Pro Ser Ser Ile Ser Val Leu Ala Ala Gly Ile Leu Val Pro Val
 1               5                  10                  15

Leu Gly Ala Val Ala Ala Lys Leu Pro Pro Thr Ala Gln Ile Ile Asp
                 20                  25                  30

Gln Lys Ser Phe Asn Val Leu Lys Asp Val Pro Pro Ala Val Ala
             35                  40                  45

Asn Asp Ser Leu Val Phe Thr Trp Pro Gly Val Thr Glu Glu Ser Leu
         50                  55                  60

Val Glu Lys Pro Phe His Val Tyr Asp Glu Glu Phe Tyr Asp Val Ile
 65                  70                  75                  80

Gly Lys Asp Pro Ser Leu Thr Leu Ile Ala Thr Ser Asp Thr Asp Pro
                 85                  90                  95

Ile Phe His Glu Ala Val Val Trp Tyr Pro Pro Thr Glu Glu Val Phe
            100                 105                 110

Phe Val Gln Asn Ala Gly Ala Pro Ala Ala Gly Thr Gly Leu Asn Lys
        115                 120                 125
```

```
Ser Ser Ile Ile Gln Lys Ile Ser Leu Lys Glu Ala Asp Glu Val Arg
    130                 135                 140

Lys Gly Lys Lys Asp Glu Val Lys Val Thr Val Val Asp Ser Asn Pro
145                 150                 155                 160

Gln Val Ile Asn Pro Asn Gly Gly Thr Tyr Tyr Lys Gly Asn Ile Ile
                165                 170                 175

Phe Ala Gly Glu Gly Gln Gly Asp Asp Val Pro Ser Ala Leu Tyr Leu
            180                 185                 190

Met Asn Pro Leu Pro Pro Tyr Asn Thr Thr Leu Leu Asn Asn Tyr
        195                 200                 205

Phe Gly Arg Gln Phe Asn Ser Leu Asn Asp Val Gly Ile Asn Pro Arg
    210                 215                 220

Asn Gly Asp Leu Tyr Phe Thr Asp Thr Leu Tyr Gly Tyr Leu Gln Asp
225                 230                 235                 240

Phe Arg Pro Val Pro Gly Leu Arg Asn Gln Val Tyr Arg Tyr Asn Phe
                245                 250                 255

Asp Thr Gly Ala Val Thr Val Val Ala Asp Asp Phe Thr Leu Pro Asn
            260                 265                 270

Gly Ile Gly Phe Gly Pro Asp Gly Lys Lys Val Tyr Val Thr Asp Thr
        275                 280                 285

Gly Ile Ala Leu Gly Phe Tyr Gly Arg Asn Leu Ser Ser Pro Ala Ser
    290                 295                 300

Val Tyr Ser Phe Asp Val Asn Gln Asp Gly Thr Leu Gln Asn Arg Lys
305                 310                 315                 320

Thr Phe Ala Tyr Val Ala Ser Phe Ile Pro Asp Gly Val His Thr Asp
                325                 330                 335

Ser Lys Gly Arg Val Tyr Ala Gly Cys Gly Asp Gly Val His Val Trp
            340                 345                 350

Asn Pro Ser Gly Lys Leu Ile Gly Lys Ile Tyr Thr Gly Thr Val Ala
        355                 360                 365

Ala Asn Phe Gln Phe Ala Gly Lys Gly Arg Met Ile Ile Thr Gly Gln
    370                 375                 380

Thr Lys Leu Phe Tyr Val Thr Leu Gly Ala Ser Gly Pro Lys Leu Tyr
385                 390                 395                 400

Asp Gly Gly Ser Leu Glu His His His His His
                405                 410

<210> SEQ ID NO 67
<211> LENGTH: 318
<212> TYPE: PRT
<213> ORGANISM: Euglena gracilis

<400> SEQUENCE: 67

Met Arg Thr Leu Ala Thr Val Ala Ser Gln Thr Asp Ala Trp Thr Gly
1               5                   10                  15

Glu Gly Pro Val Trp Cys Ala Arg Arg Cys Leu Tyr Tyr Val Asp
                20                  25                  30

Leu Gly Asp Thr Arg Pro Gly Lys Leu His Val Tyr His Pro Glu Arg
            35                  40                  45

Cys Val Glu Glu Ile His Asp Leu Pro Ala Met Thr Lys Asp Phe Thr
        50                  55                  60

Gln Val Thr Ala Val Thr Val Val Gln Asn Glu Pro His Arg Leu Ala
65                  70                  75                  80

Val Ala Thr Glu Ala Gly Val Phe Leu Tyr Asp Cys Gln Ser Gly Asp
                85                  90                  95
```

-continued

```
Leu Arg Arg Leu Thr Gly Glu Leu Gln Pro Glu Leu Pro Lys Gly Ser
                100                 105                 110

Tyr Arg Ser Asn Asp Gly Lys Cys Asp Pro Arg Gly Arg Phe Leu Ile
            115                 120                 125

Gly Thr Met Leu Phe Ser Ala Asp Ala Pro Ser Gly Gly Leu Phe Ser
130                 135                 140

Val Ala Gly Ser Thr Ile Gln Gln Leu Leu Thr Gly Val Thr Ile Gly
145                 150                 155                 160

Asn Gly Leu Ala Trp Ser Ala Asn Gly Arg Thr Met Tyr Phe Ile Asp
                165                 170                 175

Ser Pro Leu Lys Arg Ile Asp Ala Phe Glu Tyr His Leu Asp Ala Gly
            180                 185                 190

Thr Leu Gly Ala Arg Arg Thr Ala Phe Asp Phe Ala Asp Tyr Phe Ala
        195                 200                 205

Gln Gln Ala Gly Trp Glu Glu Ala Ala Pro Asp Gly Met Thr Ile Asp
210                 215                 220

Ala Glu Gly Leu Leu Trp Val Ala Ile Tyr Gly Gly Ala Ala Leu
225                 230                 235                 240

Arg Val Asp Pro Ala Lys Glu Glu Val Val Cys Arg Val Asp Cys Pro
                245                 250                 255

Ala Lys Tyr Thr Thr Ser Val Ala Leu Gly Gly Pro Ala Arg Asp Thr
            260                 265                 270

Leu Tyr Ile Thr Ser Phe Arg Arg Gly Asp Ala Gly Pro Asp Ala Gly
        275                 280                 285

Ala Val Phe Gln Cys Arg Ala Pro Ala Pro Gly Pro Pro Ala Glu
        290                 295                 300

Phe Arg Leu Gly Gly Ser Leu Glu His His His His His
305                 310                 315

<210> SEQ ID NO 68
<211> LENGTH: 277
<212> TYPE: PRT
<213> ORGANISM: Pseudomonas putida

<400> SEQUENCE: 68

Met Phe Lys Leu Leu Ser Lys Leu Leu Val Tyr Leu Thr Ala Ser Ile
1               5                   10                  15

Met Ala Ile Ala Ser Pro Leu Ala Phe Ser Val Asp Ser Ser Gly Glu
                20                  25                  30

Tyr Pro Thr Val Ser Glu Ile Pro Val Gly Glu Val Arg Leu Tyr Gln
            35                  40                  45

Ile Ala Asp Gly Val Trp Ser His Ile Ala Thr Arg Ser Phe Asp Gly
50                  55                  60

Ala Val Tyr Pro Ser Asn Gly Leu Ile Val Arg Asp Gly Asp Glu Leu
65                  70                  75                  80

Leu Leu Ile Asp Thr Ala Trp Gly Ala Lys Asn Thr Ala Ala Leu Leu
                85                  90                  95

Ala Glu Ile Glu Lys Gln Ile Gly Leu Pro Val Thr Arg Ala Val Ser
            100                 105                 110

Thr His Phe His Asp Asp Arg Val Gly Gly Val Asp Val Leu Arg Ala
        115                 120                 125

Ala Gly Val Ala Thr Tyr Ala Ser Pro Ser Thr Arg Arg Leu Ala Glu
        130                 135                 140

Val Glu Gly Ser Glu Ile Pro Thr His Ser Leu Glu Gly Leu Ser Ser
```

```
                145                 150                 155                 160
        Ser Gly Asp Ala Val Arg Phe Gly Pro Val Glu Leu Phe Tyr Pro Gly
                        165                 170                 175

Ala Ala His Ser Thr Asp Asn Leu Val Val Tyr Val Pro Ser Ala Ser
                        180                 185                 190

Val Leu Tyr Gly Gly Cys Ala Ile Tyr Glu Leu Ser Arg Thr Ser Ala
                        195                 200                 205

Gly Asn Val Ala Asp Ala Asp Leu Ala Glu Trp Pro Thr Ser Ile Glu
                        210                 215                 220

Arg Ile Gln Gln His Tyr Pro Glu Ala Gln Phe Val Ile Pro Gly His
        225                 230                 235                 240

Gly Leu Pro Gly Gly Leu Asp Leu Leu Lys His Thr Thr Asn Val Val
                        245                 250                 255

Lys Ala His Thr Asn Arg Ser Val Val Glu Gly Gly Ser Leu Glu His
                        260                 265                 270

His His His His His
                        275

<210> SEQ ID NO 69
<211> LENGTH: 277
<212> TYPE: PRT
<213> ORGANISM: Pseudomonas aeruginosa

<400> SEQUENCE: 69

Met Leu Lys Val Ile Ser Ser Leu Leu Val Tyr Met Thr Ala Ser Val
1               5                   10                  15

Met Ala Val Ala Ser Pro Leu Ala His Ser Gly Glu Pro Ser Gly Glu
                20                  25                  30

Tyr Pro Thr Val Asn Glu Ile Pro Val Gly Glu Val Arg Leu Tyr Gln
                35                  40                  45

Ile Ala Asp Gly Val Trp Ser His Ile Ala Thr Gln Ser Phe Asp Gly
        50                  55                  60

Ala Val Tyr Pro Ser Asn Gly Leu Ile Val Arg Asp Gly Asp Glu Leu
65                  70                  75                  80

Leu Leu Ile Asp Thr Ala Trp Gly Ala Lys Asn Thr Ala Ala Leu Leu
                85                  90                  95

Ala Glu Ile Glu Lys Gln Ile Gly Leu Pro Val Thr Arg Ala Val Ser
                100                 105                 110

Thr His Phe His Asp Asp Arg Val Gly Gly Val Asp Val Leu Arg Ala
                115                 120                 125

Ala Gly Val Ala Thr Tyr Ala Ser Pro Ser Thr Arg Arg Leu Ala Glu
                130                 135                 140

Ala Glu Gly Asn Glu Ile Pro Thr His Ser Leu Glu Gly Leu Ser Ser
145                 150                 155                 160

Ser Gly Asp Ala Val Arg Phe Gly Pro Val Glu Leu Phe Tyr Pro Gly
                        165                 170                 175

Ala Ala His Ser Thr Asp Asn Leu Val Val Tyr Val Pro Ser Ala Asn
                        180                 185                 190

Val Leu Tyr Gly Gly Cys Ala Val His Glu Leu Ser Arg Thr Ser Ala
                        195                 200                 205

Gly Asn Val Ala Asp Ala Asp Leu Ala Glu Trp Pro Thr Ser Val Glu
                        210                 215                 220

Arg Ile Gln Lys His Tyr Pro Glu Ala Glu Val Val Ile Pro Gly His
225                 230                 235                 240
```

-continued

Gly Leu Pro Gly Gly Leu Asp Leu Leu Gln His Thr Ala Asn Val Val
            245                 250                 255

Lys Ala His Lys Asn Arg Ser Val Ala Glu Gly Gly Ser Leu Glu His
        260                 265                 270

His His His His His
        275

<210> SEQ ID NO 70
<211> LENGTH: 585
<212> TYPE: PRT
<213> ORGANISM: Rhodococcus sp.

<400> SEQUENCE: 70

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

-continued

```
Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Ser Gly Ala
            355                 360                 365

Ala Asn Thr Ser Thr Gly Gly Gly Thr Leu Ser Thr Ser Ile Ser Gly
        370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
                435                 440                 445

Leu Phe Val Ser Ser Ala Val Asp Thr Asp Phe Thr Ala Lys Leu
            450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Asn
            515                 520                 525

Phe Pro Lys Tyr Asp Arg Asn Ser Asn Thr Gly Gly Val Ile Ala Arg
            530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Gly Gly
                565                 570                 575

Ser Leu Glu His His His His His His
            580                 585
```

<210> SEQ ID NO 71
<211> LENGTH: 277
<212> TYPE: PRT
<213> ORGANISM: Trypanosoma brucei

<400> SEQUENCE: 71

```
Met Ser Phe Lys Pro Thr Ile Ser Val His Ala Thr Pro Gln Glu Leu
1               5                   10                  15

Ser Ala Ala Gly Cys Arg Lys Ile Val Glu Ile Ile Glu Ala Ser Gly
            20                  25                  30

Ser Gln Gln Trp Pro Leu Ser Ile Ala Leu Ala Gly Gly Ser Thr Pro
        35                  40                  45

Lys Met Thr Tyr Ala Arg Leu His Asp Glu His Leu Asn Leu Leu Arg
    50                  55                  60

Glu Lys Arg Ala Leu Arg Phe Phe Met Gly Asp Glu Arg Met Val Pro
65                  70                  75                  80

Ala Asp Ser Thr Asp Ser Asn Tyr Asn Met Ala Arg Glu Val Leu Leu
                85                  90                  95

His Asp Ile Pro Asp Asp Leu Val Phe Pro Phe Asp Thr Ser Ala Val
            100                 105                 110

Thr Pro Ser Ala Glu Ala Thr Ser Ala Asp Ala Met Arg Val Ala Glu
```

```
            115                 120                 125
Ala Tyr Gly Lys Gln Leu Ala Ser Leu Leu Pro Leu Lys Ser Val Gly
        130                 135                 140

Glu Ala Gly Pro Lys Val Pro Val Phe Asp Val Val Leu Leu Gly Leu
145                 150                 155                 160

Gly Ser Asp Gly His Thr Ala Ser Ile Phe Pro Gly Ser Gln Ala Glu
                165                 170                 175

Lys Glu Thr Asp Gly Lys Val Val Ser Val Gly Phe Pro Ser Glu
            180                 185                 190

Thr Met Lys Pro Lys Val Trp Arg Val Thr Leu Ser Pro Ala Thr Ile
            195                 200                 205

Met Gln Ala Arg Asn Val Ile Val Leu Ala Thr Gly Ala Glu Lys Lys
        210                 215                 220

Trp Val Val Asp Gly Ile Leu Ala Asp Thr Ala His Lys Ala Pro Val
225                 230                 235                 240

Ala Arg Phe Leu Arg Gly Cys Glu Gly Asn Val Ser Phe Leu Leu Asp
                245                 250                 255

Lys Glu Ile Ala Glu Asn Leu Ala Lys Phe Gly Gly Ser Leu Glu His
            260                 265                 270

His His His His His
        275

<210> SEQ ID NO 72
<211> LENGTH: 274
<212> TYPE: PRT
<213> ORGANISM: Paraburkholderia xenovorans

<400> SEQUENCE: 72

Met Pro Tyr Ala Ala Val Asn Gly Thr Glu Leu His Tyr Arg Ile Asp
1               5                   10                  15

Gly Glu Arg His Gly Asn Ala Pro Trp Ile Val Leu Ser Asn Ser Leu
            20                  25                  30

Gly Thr Asp Leu Ser Met Trp Ala Pro Gln Val Ala Ala Leu Ser Lys
        35                  40                  45

His Phe Arg Val Leu Arg Tyr Asp Thr Arg Gly His Gly His Ser Glu
    50                  55                  60

Ala Pro Lys Gly Pro Tyr Thr Ile Glu Gln Leu Thr Gly Asp Val Leu
65                  70                  75                  80

Gly Leu Met Asp Thr Leu Lys Ile Ala Arg Ala Asn Phe Cys Gly Leu
                85                  90                  95

Ser Met Gly Gly Leu Thr Gly Val Ala Leu Ala Ala Arg His Ala Asp
            100                 105                 110

Arg Ile Glu Arg Val Ala Leu Cys Asn Thr Ala Ala Arg Ile Gly Ser
        115                 120                 125

Pro Glu Val Trp Val Pro Arg Ala Val Lys Ala Arg Thr Glu Gly Met
    130                 135                 140

His Ala Leu Ala Asp Ala Val Leu Pro Arg Trp Phe Thr Ala Asp Tyr
145                 150                 155                 160

Met Glu Arg Glu Pro Val Val Leu Ala Met Ile Arg Asp Val Phe Val
                165                 170                 175

His Thr Asp Lys Glu Gly Tyr Ala Ser Asn Cys Glu Ala Ile Asp Ala
            180                 185                 190

Ala Asp Leu Arg Pro Glu Ala Pro Gly Ile Lys Val Pro Ala Leu Val
        195                 200                 205
```

```
Ile Ser Gly Thr His Asp Leu Ala Ala Thr Pro Ala Gln Gly Arg Glu
210                 215                 220

Leu Ala Gln Ala Ile Ala Gly Ala Arg Tyr Val Glu Leu Asp Ala Ser
225                 230                 235                 240

His Ile Ser Asn Ile Glu Arg Ala Asp Ala Phe Thr Lys Thr Val Val
                245                 250                 255

Asp Phe Leu Thr Glu Gln Lys Gly Gly Ser Leu Glu His His His His
                260                 265                 270

His His

<210> SEQ ID NO 73
<211> LENGTH: 286
<212> TYPE: PRT
<213> ORGANISM: Thermogutta terrifontis

<400> SEQUENCE: 73

Met Ala Gln Arg Val Lys Ile Thr Thr Thr Ala Thr Pro Gly Glu Ile
1               5                   10                  15

Glu Leu Ala Phe Glu Asp Thr Gly Thr Gly Leu Pro Val Leu Leu Val
                20                  25                  30

His Gly Phe Pro Leu Asp Arg Thr Met Trp Lys Ala Gln Arg Glu Glu
            35                  40                  45

Leu Cys Asp Glu Phe Arg Val Ile Val Pro Asp Leu Arg Gly Phe Gly
50                  55                  60

Glu Ser Gln Val Ile Pro Gly Val Ala Thr Met Glu Ala Met Ala Asp
65                  70                  75                  80

Asp Leu Ala Gly Leu Cys Asn His Leu Gly Leu Thr Gly Lys Ile Val
                85                  90                  95

Leu Gly Gly Leu Ser Met Gly Gly Tyr Val Ala Phe Ala Phe Ala Arg
                100                 105                 110

Lys Tyr Arg Asp Arg Leu Ala Gly Leu Ile Leu Cys Asp Thr Arg Ala
            115                 120                 125

Arg Pro Asp Ser Pro Glu Ala Lys Glu Asn Arg Arg Val Ala Glu
130                 135                 140

Arg Val Arg Arg Glu Gly Pro Gly Phe Ile Ala Glu Glu Met Ile Pro
145                 150                 155                 160

Arg Leu Cys Cys Glu Ser Thr Phe Arg Asn His Pro Glu Val Ile Glu
                165                 170                 175

Lys Ile Arg Gln Met Ile Leu Ser Ala Pro Pro Glu Gly Val Ala Ala
            180                 185                 190

Ala Ala Leu Gly Met Ala Glu Arg Pro Asp Ser Thr Asp Leu Leu Pro
        195                 200                 205

Ala Leu Ser Cys Pro Thr Leu Val Leu Val Gly Gln Phe Asp Ala Ile
210                 215                 220

Ser Pro Pro Glu Glu Met Glu Ala Met Ala Arg Thr Ile Pro Gln Ser
225                 230                 235                 240

Gln Phe Val Val Ile Pro Asp Ala Gly His Leu Pro Pro Met Glu Gln
                245                 250                 255

Pro Glu Arg Val Thr Gln Ala Ile Arg Glu Trp Leu Arg Lys Val His
            260                 265                 270

Thr Glu Ala Gly Gly Ser Leu Glu His His His His His His
        275                 280                 285

<210> SEQ ID NO 74
<211> LENGTH: 309
```

<212> TYPE: PRT
<213> ORGANISM: Streptomyces purpurascens

<400> SEQUENCE: 74

Met Ser Glu Arg Ile Val Pro Ser Gly Asp Val Glu Leu Trp Ser Asp
1               5                   10                  15

Asp Phe Gly Asp Pro Ala Asp Pro Ala Leu Leu Leu Val Met Gly Gly
                20                  25                  30

Asn Leu Ser Ala Leu Gly Trp Pro Asp Glu Phe Ala Arg Arg Leu Ala
            35                  40                  45

Asp Gly Gly Leu His Val Ile Arg Tyr Asp His Arg Asp Thr Gly Arg
        50                  55                  60

Ser Thr Thr Arg Asp Phe Ala Ala His Pro Tyr Gly Phe Gly Glu Leu
65                  70                  75                  80

Ala Ala Asp Ala Val Ala Val Leu Asp Gly Trp Gly Val Asp Arg Ala
                85                  90                  95

His Val Val Gly Leu Ser Met Gly Ala Thr Ile Thr Gln Val Ile Ala
                100                 105                 110

Leu Asp His His Asp Arg Leu Ser Ser Leu Thr Met Leu Leu Gly Gly
            115                 120                 125

Gly Leu Asp Ile Asp Phe Asp Ala Asn Ile Glu Arg Val Met Arg Gly
        130                 135                 140

Glu Pro Thr Leu Asp Gly Leu Pro Gly Pro Gln Gln Pro Phe Leu Asp
145                 150                 155                 160

Ala Leu Ala Leu Met Asn Gln Pro Ala Glu Gly Arg Ala Ala Glu Val
                165                 170                 175

Ala Lys Arg Val Ser Lys Trp Arg Ile Leu Ser Gly Thr Gly Val Pro
                180                 185                 190

Phe Asp Asp Ala Glu Tyr Ala Arg Trp Glu Arg Ala Ile Asp His
            195                 200                 205

Ala Gly Gly Val Leu Ala Glu Pro Tyr Ala His Tyr Ser Leu Thr Leu
        210                 215                 220

Pro Pro Pro Ser Arg Ala Ala Glu Leu Arg Glu Val Thr Val Pro Thr
225                 230                 235                 240

Leu Val Ile Gln Ala Glu His Asp Pro Ile Ala Pro Ala Pro His Gly
                245                 250                 255

Lys His Leu Ala Gly Leu Ile Pro Thr Ala Arg Leu Ala Glu Ile Pro
                260                 265                 270

Gly Met Gly His Ala Leu Pro Ser Ser Val His Gly Pro Leu Ala Glu
            275                 280                 285

Val Ile Leu Ala His Thr Arg Ser Ala Ala Gly Gly Ser Leu Glu His
        290                 295                 300

His His His His
305

<210> SEQ ID NO 75
<211> LENGTH: 261
<212> TYPE: PRT
<213> ORGANISM: Bacillus thuringiensis

<400> SEQUENCE: 75

Met Thr Val Lys Lys Leu Tyr Phe Ile Pro Ala Gly Arg Cys Met Leu
1               5                   10                  15

Asp His Ser Ser Val Asn Ser Ala Leu Thr Pro Gly Lys Leu Leu Asn
                20                  25                  30

Leu Pro Val Trp Cys Tyr Leu Leu Glu Thr Glu Gly Pro Ile Leu
            35                  40                  45

Val Asp Thr Gly Met Pro Glu Ser Ala Val Asn Asn Glu Gly Leu Phe
 50                  55                  60

Asn Gly Thr Phe Val Glu Gly Gln Ile Leu Pro Lys Met Thr Glu Glu
65                  70                  75                  80

Asp Arg Ile Val Asn Ile Leu Lys Arg Val Gly Tyr Glu Pro Asp Asp
                85                  90                  95

Leu Leu Tyr Ile Ile Ser Ser His Leu His Phe Asp His Ala Gly Gly
            100                 105                 110

Asn Gly Ala Phe Thr Asn Thr Pro Ile Ile Val Gln Arg Thr Glu Tyr
            115                 120                 125

Glu Ala Ala Leu His Arg Glu Glu Tyr Met Lys Glu Cys Ile Leu Pro
130                 135                 140

His Leu Asn Tyr Lys Ile Ile Glu Gly Asp Tyr Glu Val Val Pro Gly
145                 150                 155                 160

Val Gln Leu Leu Tyr Thr Pro Gly His Ser Pro Gly His Gln Ser Leu
                165                 170                 175

Phe Ile Glu Thr Glu Gln Ser Gly Ser Val Leu Leu Thr Ile Asp Ala
            180                 185                 190

Ser Tyr Thr Lys Glu Asn Phe Glu Asp Glu Val Pro Phe Ala Gly Phe
            195                 200                 205

Asp Pro Glu Leu Ala Leu Ser Ser Ile Lys Arg Leu Lys Glu Val Val
            210                 215                 220

Lys Lys Glu Lys Pro Ile Ile Phe Phe Gly His Asp Ile Glu Gln Glu
225                 230                 235                 240

Lys Ser Cys Arg Val Phe Pro Glu Tyr Ile Gly Gly Ser Leu Glu His
                245                 250                 255

His His His His His
            260

<210> SEQ ID NO 76
<211> LENGTH: 377
<212> TYPE: PRT
<213> ORGANISM: Dickeya dadantii

<400> SEQUENCE: 76

Met Leu Lys Thr Ile Ser Gly Thr Leu Ala Leu Ser Leu Ile Ile Ala
1               5                   10                  15

Ala Ser Val His Gln Ala Gln Ala Ala Thr Thr Tyr Asn Ala Val Val
            20                  25                  30

Ser Lys Ser Ser Ser Asp Gly Lys Thr Phe Lys Thr Ile Ala Asp Ala
            35                  40                  45

Ile Ala Ser Ala Pro Ala Gly Ser Thr Pro Phe Val Ile Leu Ile Lys
 50                  55                  60

Asn Gly Val Tyr Asn Glu Arg Leu Thr Ile Thr Arg Asn Asn Leu His
65                  70                  75                  80

Leu Lys Gly Glu Ser Arg Asn Gly Ala Val Ile Ala Ala Thr Ala
            85                  90                  95

Ala Gly Thr Leu Lys Ser Asp Gly Ser Lys Trp Gly Thr Ala Gly Ser
            100                 105                 110

Ser Thr Ile Thr Ile Ser Ala Lys Asp Phe Ser Ala Gln Ser Leu Thr
            115                 120                 125

Ile Arg Asn Asp Phe Asp Phe Pro Ala Asn Gln Ala Lys Ser Asp Ser
130                 135                 140

```
Asp Ser Ser Lys Ile Lys Asp Thr Gln Ala Val Ala Leu Tyr Val Thr
145                 150                 155                 160

Lys Ser Gly Asp Arg Ala Tyr Phe Lys Asp Val Ser Leu Val Gly Tyr
                165                 170                 175

Gln Asp Thr Leu Tyr Val Ser Gly Gly Arg Ser Phe Phe Ser Asp Cys
            180                 185                 190

Arg Ile Ser Gly Thr Val Asp Phe Ile Phe Gly Asp Gly Thr Ala Leu
        195                 200                 205

Phe Asn Asn Cys Asp Leu Val Ser Arg Tyr Arg Ala Asp Val Lys Ser
    210                 215                 220

Gly Asn Val Ser Gly Tyr Leu Thr Ala Pro Ser Thr Asn Ile Asn Gln
225                 230                 235                 240

Lys Tyr Gly Leu Val Ile Thr Asn Ser Arg Val Ile Arg Glu Ser Asp
                245                 250                 255

Ser Val Pro Ala Lys Ser Tyr Gly Leu Gly Arg Pro Trp His Pro Thr
            260                 265                 270

Thr Thr Phe Ser Asp Gly Arg Tyr Ala Asp Pro Asn Ala Ile Gly Gln
        275                 280                 285

Thr Val Phe Leu Asn Thr Ser Met Asp Asn His Ile Tyr Gly Trp Asp
    290                 295                 300

Lys Met Ser Gly Lys Asp Lys Asn Gly Asn Thr Ile Trp Phe Asn Pro
305                 310                 315                 320

Glu Asp Ser Arg Phe Phe Glu Tyr Lys Ser Tyr Gly Ala Gly Ala Thr
                325                 330                 335

Val Ser Lys Asp Arg Arg Gln Leu Thr Asp Ala Gln Ala Ala Glu Tyr
            340                 345                 350

Thr Gln Ser Lys Val Leu Gly Asp Trp Thr Pro Thr Leu Pro Gly Gly
        355                 360                 365

Ser Leu Glu His His His His His His
    370                 375

<210> SEQ ID NO 77
<211> LENGTH: 322
<212> TYPE: PRT
<213> ORGANISM: Archaeoglobus fulgidus

<400> SEQUENCE: 77

Met Leu Asp Met Pro Ile Asp Pro Val Tyr Tyr Gln Leu Ala Glu Tyr
1               5                   10                  15

Phe Asp Ser Leu Pro Lys Phe Asp Gln Phe Ser Ser Ala Arg Glu Tyr
            20                  25                  30

Arg Glu Ala Ile Asn Arg Ile Tyr Glu Glu Arg Asn Arg Gln Leu Ser
        35                  40                  45

Gln His Glu Arg Val Glu Arg Val Glu Asp Arg Thr Ile Lys Gly Arg
    50                  55                  60

Asn Gly Asp Ile Arg Val Arg Val Tyr Gln Gln Lys Pro Asp Ser Pro
65                  70                  75                  80

Val Leu Val Tyr Tyr His Gly Gly Gly Phe Val Ile Cys Ser Ile Glu
                85                  90                  95

Ser His Asp Ala Leu Cys Arg Arg Ile Ala Arg Leu Ser Asn Ser Thr
            100                 105                 110

Val Val Ser Val Asp Tyr Arg Leu Ala Pro Glu His Lys Phe Pro Ala
        115                 120                 125

Ala Val Tyr Asp Cys Tyr Asp Ala Thr Lys Trp Val Ala Glu Asn Ala
```

```
                130                 135                 140
Glu Glu Leu Arg Ile Asp Pro Ser Lys Ile Phe Val Gly Gly Asp Ser
145                 150                 155                 160

Ala Gly Gly Asn Leu Ala Ala Val Ser Ile Met Ala Arg Asp Ser
                165                 170                 175

Gly Glu Asp Phe Ile Lys His Gln Ile Leu Ile Tyr Pro Val Val Asn
            180                 185                 190

Phe Val Ala Pro Thr Pro Ser Leu Leu Glu Phe Gly Glu Gly Leu Trp
                195                 200                 205

Ile Leu Asp Gln Lys Ile Met Ser Trp Phe Ser Glu Gln Tyr Phe Ser
            210                 215                 220

Arg Glu Glu Asp Lys Phe Asn Pro Leu Ala Ser Val Ile Phe Ala Asp
225                 230                 235                 240

Leu Glu Asn Leu Pro Pro Ala Leu Ile Ile Thr Ala Glu Tyr Asp Pro
                245                 250                 255

Leu Arg Asp Glu Gly Glu Val Phe Gly Gln Met Leu Arg Arg Ala Gly
            260                 265                 270

Val Glu Ala Ser Ile Val Arg Tyr Arg Gly Val Leu His Gly Phe Ile
275                 280                 285

Asn Tyr Tyr Pro Val Leu Lys Ala Ala Arg Asp Ala Ile Asn Gln Ile
            290                 295                 300

Ala Ala Leu Leu Val Phe Asp Gly Gly Ser Leu Glu His His His His
305                 310                 315                 320

His His

<210> SEQ ID NO 78
<211> LENGTH: 308
<212> TYPE: PRT
<213> ORGANISM: Bacillus thuringiensis

<400> SEQUENCE: 78

Met Thr Leu Asp Leu Gln Val Gln Ser Phe Leu Ala Gln Gly Gly Asn
1               5                   10                  15

Leu Asn Thr Leu Thr Gly Glu Glu His Gly Glu Ala Lys Ala Val Phe
            20                  25                  30

Lys Val Glu Asp Phe Tyr Ile Pro Val Lys Asp Gly Glu Ile Lys Leu
        35                  40                  45

Arg Val Tyr Thr Pro Asn Glu Lys Glu Ser Leu Pro Val Phe Val Tyr
50                  55                  60

Leu His Gly Gly Gly Trp Val Ala Gly Asp Ile Gln Ala Val Asp Thr
65                  70                  75                  80

Leu Cys Gln Asn Ile Ala His Asp Ala Glu Cys Ile Val Val Ala Val
                85                  90                  95

Glu Tyr Arg Leu Ala Pro Thr His Lys Phe Pro Val Pro Leu Glu Asp
            100                 105                 110

Cys Tyr Glu Ala Thr Lys Trp Val Ala Glu Asn Ser Ser Met Leu Asn
        115                 120                 125

Ala Asp Lys Thr Lys Ile Ala Ile Gly Gly Asp Ser Ala Gly Gly Asn
130                 135                 140

Ile Ala Ala Ala Val Val Ile Met Ala Gln Lys Phe Asn Asn Leu Ser
145                 150                 155                 160

Leu Val Ala Gln Val Leu Val Tyr Pro Val Val Asp Leu Thr Leu Thr
                165                 170                 175

Phe Lys Ala Gln Ser Tyr Arg Asp Asn Ala Glu Gly Tyr Leu Leu Thr
```

```
            180                 185                 190
Thr Glu Gly Val Phe Trp Ala Thr Gln Met Tyr Leu Arg Asp Glu Ile
                195                 200                 205

Asp Arg Tyr Asn Val Phe Ala Ser Pro Ser Val Asn Asn Glu Leu Glu
    210                 215                 220

Asn Leu Pro Pro Ala Leu Ile Ile Thr Ala Glu Tyr Asp Pro Leu Arg
225                 230                 235                 240

Asp Asp Gly Ala Ala Tyr Ala Lys Arg Leu Glu Ala Ala Gly Ile Pro
                245                 250                 255

Val Glu Tyr Lys Cys Tyr Glu Gly Met Val His Gly Phe Phe Trp Met
                260                 265                 270

Ala Gly Ile Met Asp Lys Gly Leu Gln Ala Arg Leu Gln Val Ser Asn
                275                 280                 285

Tyr Leu Lys Ser Val Phe Val Gly Lys Gly Gly Ser Leu Glu His His
                290                 295                 300

His His His His
305

<210> SEQ ID NO 79
<211> LENGTH: 321
<212> TYPE: PRT
<213> ORGANISM: Alicyclobacillus acidocaldarius

<400> SEQUENCE: 79

Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
                20                  25                  30

Gln Gln Ser Leu Phe Pro Pro Val Lys Lys Glu Pro Val Ala Glu Val
            35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Leu
                165                 170                 175

Ala Phe Gln Leu Leu Ile Tyr Pro Ser Thr Gly Tyr Asp Pro Ala His
                180                 185                 190

Pro Pro Ala Ser Ile Glu Glu Asn Ala Glu Gly Tyr Leu Leu Thr Gly
            195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240
```

Leu Pro Pro Ala Tyr Ile Ala Thr Ala Gln Tyr Asp Pro Leu Arg Asp
            245                 250                 255

Val Gly Lys Leu Tyr Ala Glu Ala Leu Asn Lys Ala Gly Val Lys Val
        260                 265                 270

Glu Ile Glu Asn Phe Glu Asp Leu Ile His Gly Phe Ala Gln Phe Tyr
    275                 280                 285

Ser Leu Ser Pro Gly Ala Thr Lys Ala Leu Val Arg Ile Ala Glu Lys
290                 295                 300

Leu Arg Asp Ala Leu Ala Gly Gly Ser Leu Glu His His His His His
305                 310                 315                 320

His

<210> SEQ ID NO 80
<211> LENGTH: 317
<212> TYPE: PRT
<213> ORGANISM: Saccharolobus solfataricus

<400> SEQUENCE: 80

Met Pro Leu Asp Pro Glu Val Arg Asn Phe Leu Gln Val Tyr Tyr Lys
1               5                   10                  15

Ala Asn Ile Ile Asp Phe Thr Lys Tyr Gln Phe Gln Glu Ile Arg Gln
            20                  25                  30

Lys Val Asn Glu Leu Leu Ala Lys Ala Val Pro Lys Asp Pro Val Gly
        35                  40                  45

Glu Thr Arg Asp Met Lys Ile Lys Leu Glu Asp Tyr Glu Leu Pro Ile
    50                  55                  60

Arg Ile Tyr Ser Pro Ile Lys Arg Thr Asn Asn Gly Leu Val Met His
65                  70                  75                  80

Phe His Gly Gly Ala Trp Ile Leu Gly Ser Ile Glu Thr Glu Asp Ala
                85                  90                  95

Ile Ser Arg Ile Leu Ser Asn Ser Cys Glu Cys Thr Val Ile Ser Val
            100                 105                 110

Asp Tyr Arg Leu Ala Pro Glu Tyr Lys Phe Pro Thr Ala Val Tyr Asp
        115                 120                 125

Cys Phe Asn Ala Ile Val Trp Ala Arg Asp Asn Ala Gly Glu Leu Gly
    130                 135                 140

Ile Asp Lys Asp Lys Ile Ala Thr Phe Gly Ile Ser Ala Gly Gly Asn
145                 150                 155                 160

Leu Val Ala Ala Thr Ser Leu Leu Ala Arg Asp Asn Lys Leu Lys Leu
                165                 170                 175

Thr Ala Gln Val Pro Val Val Pro Phe Val Tyr Leu Asp Leu Ala Ser
            180                 185                 190

Lys Ser Met Asn Arg Tyr Arg Lys Gly Tyr Phe Leu Asp Ile Asn Leu
        195                 200                 205

Pro Val Asp Tyr Gly Val Lys Met Tyr Ile Arg Asp Glu Lys Asp Leu
    210                 215                 220

Tyr Asn Pro Leu Phe Ser Pro Leu Ile Ala Glu Asp Leu Ser Asn Leu
225                 230                 235                 240

Pro Gln Ala Ile Val Val Thr Ala Glu Tyr Asp Pro Leu Arg Asp Gln
                245                 250                 255

Gly Glu Ala Tyr Ala Tyr Arg Leu Met Glu Ser Gly Val Pro Thr Leu
            260                 265                 270

Ser Phe Arg Val Asn Gly Asn Val His Ala Phe Leu Gly Ser Pro Arg
        275                 280                 285

Thr Ser Arg Gln Val Thr Val Met Ile Gly Ala Leu Leu Lys Asp Ile
290                 295                 300

Phe Lys Gly Ser Ser Leu Glu His His His His His His
305                 310                 315

<210> SEQ ID NO 81
<211> LENGTH: 317
<212> TYPE: PRT
<213> ORGANISM: Sulfolobus islandicus

<400> SEQUENCE: 81

Met Met Pro Leu Asp Pro Arg Ile Lys Glu Leu Leu Glu Ser Gly Phe
1               5                   10                  15

Ile Val Pro Ile Gly Lys Ala Ser Val Asp Glu Val Arg Lys Ile Phe
                20                  25                  30

Arg Gln Leu Ala Ser Ala Ala Pro Lys Val Glu Val Gly Lys Val Glu
            35                  40                  45

Asp Ile Lys Ile Pro Gly Ser Glu Ala Asn Ile Asn Ala Arg Val Tyr
        50                  55                  60

Leu Pro Lys Ala Asn Gly Pro Tyr Gly Val Leu Ile Tyr Leu His Gly
65                  70                  75                  80

Gly Gly Phe Val Ile Gly Asp Val Glu Ser Tyr Asp Pro Leu Cys Arg
                85                  90                  95

Ala Ile Thr Asn Ala Cys Asn Cys Val Val Ser Val Asp Tyr Arg
            100                 105                 110

Leu Ala Pro Glu Tyr Lys Phe Pro Ser Ala Val Ile Asp Ser Phe Asp
        115                 120                 125

Ala Thr Asn Trp Val Tyr Asn Asn Leu Asp Lys Phe Asp Gly Lys Met
130                 135                 140

Gly Val Ala Ile Ala Gly Asp Ser Ala Gly Asn Leu Ala Ala Val
145                 150                 155                 160

Val Ala Leu Leu Ser Lys Gly Lys Leu Asn Leu Lys Tyr Gln Ile Leu
                165                 170                 175

Ile Tyr Pro Ala Val Gly Phe Asp Ser Val Ser Arg Ser Met Ile Glu
            180                 185                 190

Tyr Ser Asp Gly Phe Phe Leu Thr Arg Glu His Ile Glu Trp Phe Gly
        195                 200                 205

Ser Gln Tyr Leu Arg Ser Pro Ala Asp Leu Leu Asp Phe Arg Phe Ser
210                 215                 220

Pro Ile Leu Ala Gln Asp Leu Ser Gly Leu Pro Pro Ala Leu Ile Ile
225                 230                 235                 240

Thr Ala Glu Tyr Asp Pro Leu Arg Asp Gln Gly Glu Ala Tyr Ala Asn
                245                 250                 255

Arg Leu Leu Gln Ala Gly Val Pro Val Thr Ser Val Arg Phe Asn Asn
            260                 265                 270

Val Ile His Gly Phe Leu Ser Phe Pro Leu Ile Glu Gln Gly Arg
        275                 280                 285

Asp Ala Ile Ser Leu Ile Gly Ser Val Leu Arg Arg Thr Phe Tyr Asp
290                 295                 300

Lys Ser Gly Gly Ser Leu Glu His His His His His His
305                 310                 315

<210> SEQ ID NO 82
<211> LENGTH: 314
<212> TYPE: PRT
<213> ORGANISM: Sulfurisphaera tokodaii -continued

```
<400> SEQUENCE: 82

Met Ile Asp Pro Lys Ile Lys Lys Leu Leu Glu Ser Thr Ile Gln Leu
1               5                   10                  15

Pro Ile Gly Lys Ala Ser Val Glu Glu Ile Arg Ser Leu Phe Lys Gln
            20                  25                  30

Phe Ser Ser Leu Thr Pro Arg Glu Val Gly Lys Ile Glu Asp Ile
        35                  40                  45

Thr Ile Pro Gly Ser Glu Thr Asn Ile Lys Ala Arg Val Tyr Tyr Pro
    50                  55                  60

Lys Thr Gln Gly Pro Tyr Gly Val Leu Val Tyr Tyr His Gly Gly Gly
65                  70                  75                  80

Phe Val Leu Gly Asp Ile Glu Ser Tyr Asp Pro Leu Cys Arg Ala Ile
                85                  90                  95

Thr Asn Ser Cys Gln Cys Val Thr Ile Ser Val Asp Tyr Arg Leu Ala
            100                 105                 110

Pro Glu Asn Lys Phe Pro Ala Ala Val Val Asp Ser Phe Asp Ala Leu
        115                 120                 125

Lys Trp Val Tyr Asn Asn Ser Glu Lys Phe Asn Gly Lys Tyr Gly Ile
    130                 135                 140

Ala Val Gly Gly Asp Ser Ala Gly Gly Asn Leu Ala Ala Val Thr Ala
145                 150                 155                 160

Ile Leu Ser Lys Lys Glu Asn Ile Lys Leu Lys Tyr Gln Val Leu Ile
                165                 170                 175

Tyr Pro Ala Val Ser Phe Asp Leu Ile Thr Lys Ser Leu Tyr Asp Asn
            180                 185                 190

Gly Glu Gly Phe Phe Leu Thr Arg Glu His Ile Asp Trp Phe Gly Gln
        195                 200                 205

Gln Tyr Leu Arg Ser Phe Ala Asp Leu Leu Asp Phe Arg Phe Ser Pro
    210                 215                 220

Ile Leu Ala Asp Leu Asn Asp Leu Pro Ala Leu Ile Ile Thr Ala
225                 230                 235                 240

Glu His Asp Pro Leu Arg Asp Gln Gly Glu Ala Tyr Ala Asn Lys Leu
                245                 250                 255

Leu Gln Ser Gly Val Gln Val Thr Ser Val Arg Phe Asn Asn Val Ile
            260                 265                 270

His Gly Phe Val Ser Phe Phe Pro Phe Ile Glu Gln Gly Arg Asp Ala
        275                 280                 285

Ile Gly Leu Ile Gly Tyr Val Leu Arg Lys Val Phe Tyr Gly Lys Gly
    290                 295                 300

Gly Ser Leu Glu His His His His His His
305                 310

<210> SEQ ID NO 83
<211> LENGTH: 233
<212> TYPE: PRT
<213> ORGANISM: Ventosimonas gracilis

<400> SEQUENCE: 83

Met Thr Glu Pro Leu Ile Ile Glu Pro Ser Gln Pro Ala Asp Ser Ala
1               5                   10                  15

Val Ile Trp Leu His Gly Leu Gly Ala Asp Arg Phe Asp Phe Glu Pro
            20                  25                  30

Val Ala Arg Leu Leu Gly Gln His Leu Pro Ser Thr Arg Phe Ile Leu
        35                  40                  45
```

-continued

Pro Gln Ala Pro Thr Arg Pro Val Thr Phe Asn Met Gly His Ala Met
    50                  55                  60

Pro Ser Trp Tyr Asp Ile Leu Ala Leu Asp Gly Ser Glu Arg Ala Ile
65                  70                  75                  80

Asn Pro Ala Asp Leu Glu Ala Ser Ser Glu Thr Leu Ile Ala Leu Ile
                85                  90                  95

Asn Ala Gln Gln Gln Ser Gly Ile Asp Ser Lys Arg Ile Val Leu Ala
            100                 105                 110

Gly Phe Ser Gln Gly Gly Ala Val Leu His Thr Ala Leu Leu Arg
            115                 120                 125

Phe Asp Glu Lys Leu Ala Gly Val Leu Ala Leu Ser Thr Tyr Ala Pro
    130                 135                 140

Thr Phe Asn Ala Glu Thr Gln Phe Ala Glu Ser Lys Gln Asn Leu Pro
145                 150                 155                 160

Val Leu Cys Met His Gly Ser Glu Asp Ala Val Leu Pro Ile Ser Met
                165                 170                 175

Gly Arg Ala Val Tyr Asp Lys Leu Ser Glu Gln Gly Ile Lys Ala Asn
            180                 185                 190

Trp Arg Asp Tyr Pro Met Gly His Glu Val Arg Pro Glu Gln Leu Arg
    195                 200                 205

Asp Ile Leu Asp Trp Leu Lys Asn Thr Leu Pro Ser Leu Pro Gly Gly
    210                 215                 220

Ser Leu Glu His His His His His His
225                 230

<210> SEQ ID NO 84
<211> LENGTH: 230
<212> TYPE: PRT
<213> ORGANISM: Ignatzschineria indica

<400> SEQUENCE: 84

Met Asp Lys Pro Ile Ile Leu Asp Pro Lys Gln Ser Ala Asp Ser Ala
1               5                   10                  15

Val Ile Trp Leu His Gly Leu Gly Ala Thr Lys Glu Asp Phe Leu Pro
            20                  25                  30

Val Ala Gln Ile Leu Gln Arg Asp Ala Leu Pro His Thr Arg Phe Ile
        35                  40                  45

Leu Pro Gln Ala Pro Val Arg Pro Val Thr Leu Asn Asn Gly Phe Pro
    50                  55                  60

Met Pro Ser Trp Tyr Asp Ile Ile Ala Leu Thr Ser Pro Arg Glu Ile
65                  70                  75                  80

Lys Leu Ser Glu Leu Asp Glu Ser Ser Gln Ser Ile Ile Ala Leu Ile
                85                  90                  95

Glu Ala Glu Ile Glu Lys Gly Ile Pro Leu Glu Arg Ile Ile Leu Ala
            100                 105                 110

Gly Phe Ser Gln Gly Gly Ala Val Val Leu His Thr Ala Phe Ile Ala
            115                 120                 125

Tyr Pro Lys Asn Val Gly Gly Val Met Ala Leu Ser Thr Tyr Ser Ala
    130                 135                 140

Thr Phe Asp Glu Ala Ile Thr Leu Asp Glu Lys Lys Gln Ile Pro
145                 150                 155                 160

Thr Leu His Leu His Gly Ser Leu Asp Pro Val Val Lys Ile Glu Leu
                165                 170                 175

Gly Arg Ala Ala Glu Gln Phe Leu Lys Ala Gln Gly Ile Asp Thr Arg

```
            180                 185                 190
Trp His Asp Tyr Pro Met Gln His Glu Val Ile Asn Asp Glu Leu Gln
                195                 200                 205
Asp Ile Ala Lys Trp Leu Ile Glu Arg Leu Gly Gly Gly Ser Leu Glu
    210                 215                 220
His His His His His His
225                 230

<210> SEQ ID NO 85
<211> LENGTH: 230
<212> TYPE: PRT
<213> ORGANISM: Pseudomonas furukawaii

<400> SEQUENCE: 85

Met Ser Asp Thr Leu Ile Leu Glu Pro Thr His Arg Ala Asp Ala Cys
1               5                   10                  15
Val Ile Trp Leu His Gly Leu Gly Ala Asp Arg Tyr Asp Phe Leu Pro
            20                  25                  30
Val Ala Glu Ala Leu Gln Asp Val Leu Gly Thr Thr Arg Phe Val Leu
        35                  40                  45
Pro Gln Ala Pro Thr Arg Ala Val Thr Ile Asn Gly Gly Trp Ala Met
    50                  55                  60
Pro Ser Trp Tyr Asp Ile Leu Ala Met Ser Pro Glu Arg Ala Ile Asp
65                  70                  75                  80
Glu Ala Gln Leu Glu Ala Ser Ala Gln Gln Val Met Ala Leu Ala Gln
                85                  90                  95
Ala Gln Val Asp Gly Gly Ile Glu Pro Arg Arg Ile Phe Leu Ala Gly
            100                 105                 110
Phe Ser Gln Gly Gly Ala Val Val Leu His Thr Ala Phe Leu Arg Trp
        115                 120                 125
Glu Asp Glu Leu Gly Gly Val Leu Ala Leu Ser Thr Tyr Gly Pro Thr
    130                 135                 140
Phe Thr Asp Gly Met Thr Leu Pro Asp Ala Lys Arg Gln Leu Pro Val
145                 150                 155                 160
Leu Cys Leu His Gly Thr Leu Asp Asp Val Val Leu Pro Ala Met Gly
                165                 170                 175
Arg Ala Ala His Asp Arg Leu Ala Ala Ala Gly Val Pro Val Gly Trp
            180                 185                 190
Arg Asp Tyr Pro Met Ala His Glu Val Leu Pro Gln Gln Val Arg Asp
        195                 200                 205
Ile Gly Ala Trp Leu Val Glu Arg Leu His Ser Gly Gly Ser Leu Glu
    210                 215                 220
His His His His His His
225                 230

<210> SEQ ID NO 86
<211> LENGTH: 228
<212> TYPE: PRT
<213> ORGANISM: Pseudomonas citronellolis

<400> SEQUENCE: 86

Met Ser Gln Pro Leu Leu Leu Glu Pro Thr Gln Pro Ala Asp Ser Cys
1               5                   10                  15
Val Ile Trp Leu His Gly Leu Gly Ala Asp Arg Tyr Asp Phe Glu Pro
            20                  25                  30
Val Ala Arg Met Leu Gln Lys Val Leu Pro Arg Thr Arg Phe Ile Leu
```

```
            35                  40                  45
Pro Gln Ala Pro Thr Arg Pro Val Thr Val Phe Asn Gly Met Pro Ala
 50                  55                  60
Pro Ser Trp Tyr Asp Ile Lys Ala Met Ala Pro Ala Arg Ala Ile Asp
 65                  70                  75                  80
Glu Ala Gln Leu Asp Ala Ser Ala Asp Ala Val Ile Ala Leu Ile Glu
                 85                  90                  95
Gly Gln Leu Ala Glu Gly Ile Ala Gln Arg Arg Ile Val Leu Ala Gly
                100                 105                 110
Phe Ser Gln Gly Gly Ala Val Val Leu His Thr Gly Tyr Leu Arg Trp
            115                 120                 125
Pro Gly Glu Leu Gly Gly Val Met Ala Leu Ser Thr Tyr Gly Pro Thr
        130                 135                 140
Phe Asp Asp Asp Leu Gln Leu Pro Glu Ala Lys Lys Gln Gln Pro Ala
145                 150                 155                 160
Leu Cys Leu His Gly Thr Tyr Asp Asp Val Val Ala Pro Ala Met Gly
                165                 170                 175
Arg Ala Ala Tyr Asp Phe Leu Gln Arg Gln Gly Val Ala Val Gln Trp
            180                 185                 190
Arg Asp Tyr Pro Met Ala His Glu Val Ser Asn Gln Glu Ile Ala Asp
        195                 200                 205
Ile Ala Ala Trp Leu Arg Glu Arg Leu Gly Gly Ser Leu Glu His His
    210                 215                 220
His His His His
225

<210> SEQ ID NO 87
<211> LENGTH: 226
<212> TYPE: PRT
<213> ORGANISM: Pseudomonas aeruginosa

<400> SEQUENCE: 87

Met Ser Glu Pro Leu Ile Leu Asp Ala Pro Asn Ala Asp Ala Cys Ile
 1               5                  10                  15
Ile Trp Leu His Gly Leu Gly Ala Asp Arg Thr Asp Phe Lys Pro Val
                20                  25                  30
Ala Glu Ala Leu Gln Met Val Leu Pro Ser Thr Arg Phe Ile Leu Pro
            35                  40                  45
Gln Ala Pro Ser Gln Ala Val Thr Val Asn Gly Gly Trp Val Met Pro
 50                  55                  60
Ser Trp Tyr Asp Ile Leu Ala Phe Ser Pro Ala Arg Ala Ile Asp Glu
 65                  70                  75                  80
Asp Gln Leu Asn Ala Ser Ala Asp Gln Val Ile Ala Leu Ile Asp Glu
                 85                  90                  95
Gln Arg Ala Lys Gly Ile Ala Glu Arg Ile Ile Leu Ala Gly Phe
                100                 105                 110
Ser Gln Gly Gly Ala Val Val Leu His Thr Ala Phe Arg Arg Tyr Ala
            115                 120                 125
Gln Pro Leu Gly Gly Val Leu Ala Leu Ser Thr Tyr Ala Pro Thr Phe
        130                 135                 140
Asp Asp Leu Ala Leu Asp Glu Arg His Lys Arg Ile Pro Val Leu His
145                 150                 155                 160
Leu His Gly Ser Gln Asp Asp Val Val Asp Pro Ala Leu Gly Arg Ala
                165                 170                 175
```

```
Ala His Asp Ala Leu Gln Ala Gln Gly Val Glu Val Gly Trp His Asp
            180                 185                 190

Tyr Pro Met Gly His Glu Val Ser Leu Glu Glu Ile His Asp Ile Gly
        195                 200                 205

Ala Trp Leu Arg Lys Arg Leu Gly Gly Ser Leu Glu His His His His
        210                 215                 220

His His
225

<210> SEQ ID NO 88
<211> LENGTH: 229
<212> TYPE: PRT
<213> ORGANISM: Pseudomonas saudiphocaensis

<400> SEQUENCE: 88

Met Thr Asp Pro Leu Ile Ile Glu Pro Ala Gln Thr Ala Asp Ser Cys
1               5                   10                  15

Val Ile Trp Leu His Gly Leu Gly Ala Asp Arg Tyr Asp Phe Gln Pro
            20                  25                  30

Val Ala Glu Met Leu Gln Gln Arg Leu Leu His Thr Arg Phe Val Leu
        35                  40                  45

Pro Gln Ala Pro Thr Arg Ala Val Thr Ile Asn Gly Gly Trp Ala Met
    50                  55                  60

Pro Ser Trp Tyr Asp Ile Gln Ala Met Ser Pro Ala Arg Ala Ile Asp
65              70                  75                  80

Gln Ala Gln Leu Glu Gln Ser Ala Gln Thr Val Ile Glu Leu Ile Glu
                85                  90                  95

Gln Gln Arg Asp Ser Gly Ile Asp Pro Arg Arg Ile Phe Leu Ala Gly
            100                 105                 110

Phe Ser Gln Gly Gly Ala Val Val Tyr His Thr Ala Phe Leu Arg Trp
        115                 120                 125

Ala Gly Pro Leu Gly Gly Val Leu Ala Leu Ser Thr Tyr Ala Pro Thr
    130                 135                 140

Phe Gly Asp Asp Leu Lys Leu Ser Pro Leu Gln Ala Gly Leu Pro Val
145                 150                 155                 160

Leu Cys Leu His Gly Ser Arg Asp Asp Val Val Pro Pro Ala Met Gly
                165                 170                 175

Arg Ala Ala His Asp Cys Leu Gln Gln Asn Gln Val Gln Thr Gln Trp
            180                 185                 190

Lys Glu Tyr Pro Met Ala His Glu Val Gln Pro Thr Glu Ile Gln Asp
        195                 200                 205

Ile Gly Asp Trp Leu Ala Ser Arg Leu Gly Gly Ser Leu Glu His
    210                 215                 220

His His His His His
225

<210> SEQ ID NO 89
<211> LENGTH: 229
<212> TYPE: PRT
<213> ORGANISM: Pseudomonas fluorescens

<400> SEQUENCE: 89

Met Thr Glu Pro Leu Ile Leu Gln Pro Ala Lys Pro Ala Asp Ala Cys
1               5                   10                  15

Val Ile Trp Leu His Gly Leu Gly Ala Asp Arg Tyr Asp Phe Met Pro
            20                  25                  30
```

```
Val Ala Glu Ala Leu Gln Glu Ser Leu Leu Thr Thr Arg Phe Val Leu
             35                  40                  45

Pro Gln Ala Pro Thr Arg Pro Val Thr Ile Asn Gly Gly Tyr Glu Met
     50                  55                  60

Pro Ser Trp Tyr Asp Ile Lys Ala Met Ser Pro Ala Arg Ser Ile Ser
 65                  70                  75                  80

Leu Glu Glu Leu Glu Val Ser Ala Lys Met Val Thr Asp Leu Ile Glu
                 85                  90                  95

Ala Gln Lys Arg Thr Gly Ile Asp Ala Ser Arg Ile Phe Leu Ala Gly
                100                 105                 110

Phe Ser Gln Gly Gly Ala Val Val Phe His Thr Ala Phe Ile Asn Trp
            115                 120                 125

Gln Gly Pro Leu Gly Val Ile Ala Leu Ser Thr Tyr Ala Pro Thr
            130                 135                 140

Phe Gly Asp Glu Leu Glu Leu Ser Ala Ser Gln Gln Arg Ile Pro Ala
145                 150                 155                 160

Leu Cys Leu His Gly Gln Tyr Asp Asp Val Val Gln Asn Ala Met Gly
                165                 170                 175

Arg Ser Ala Phe Glu His Leu Lys Ser Arg Gly Val Thr Val Thr Trp
            180                 185                 190

Gln Glu Tyr Pro Met Gly His Glu Val Leu Pro Gln Glu Ile His Asp
            195                 200                 205

Ile Gly Ala Trp Leu Ala Ala Arg Leu Gly Gly Gly Ser Leu Glu His
            210                 215                 220

His His His His His
225

<210> SEQ ID NO 90
<211> LENGTH: 11
<212> TYPE: PRT
<213> ORGANISM: Artificial Sequence
<220> FEATURE:
<223> OTHER INFORMATION: Hexahistidine tag

<400> SEQUENCE: 90

Gly Gly Ser Leu Glu His His His His His His
 1               5                  10

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 91

His His His His His His
 1               5
```

ENZYMATIC TREATMENT OF ANTHOCYANINS

CROSS REFERENCE TO RELATED APPLICATIONS

This application is a continuation of International Patent Application No. PCT/US2020/053849 filed Oct. 1, 2020, which claims priority to U.S. Patent Application Ser. No. 62/909,106, filed on Oct. 1, 2019, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 10, 2022, is named 069269_0524_SL.txt and is 217,578 bytes in size.

FIELD OF THE INVENTION

The presently disclosed subject matter relates to the use of natural and modified enzymes to convert mixtures of anthocyanins occurring in fruit or vegetable juice or extract into an anthocyanin molecule having desirable colorant properties. The presently disclosed subject matter further relates to isolation of the anthocyanin molecule having desirable colorant properties and use thereof in various applications including edible products.

BACKGROUND OF THE INVENTION

The use and demand of alternatives for synthetic food colorants has been increasing due to consumer demand. However, natural food colorants have not been able to achieve the same color characteristics as their synthetic counterparts, for example, FD&C Blue No. 1. The lack of a suitable natural blue colorant has also made the development of a desirable natural green hue, from a combination of natural blue and yellow colorants, difficult.

Anthocyanins are known as natural food colorants responsible for reds and blues of fruits and vegetables. It is known in the art that anthocyanin-containing juices and extracts generally exhibit red hues at low pH with a hue shifts towards purple as the pH increases. For example, it is generally observed that the hue shifts from pink to purple when hydrogen is replaced with a hydroxyl group. International Patent Publication No. WO 2014/152417 discloses the isolation of fractions of anthocyanin molecules from vegetable and fruit extracts, including red cabbage, at select pHs to provide different color characteristics than those provided by the source vegetable or fruit.

The substitution pattern of anthocyanins also affects color. For example, the number of glycosyl (sugar) units and the number and type of acyl units are observed to affect color. However, these phenomena are not well understood or predictable.

Intermolecular and intramolecular interactions also affect anthocyanin color. The same anthocyanin may produce different hues depending on what other molecules are present. For example, it is believed that acyl groups on the anthocyanin sugars can fold in and protect the flavylium cation C-2 position from nucleophilic attack. Therefore, this intramolecular interaction prevents formation of the colorless carbinol pseudo-base structure. Similarly, it is believed that anthocyanin molecules self-associate, which is evidenced by the fact that a two-fold increase in anthocyanin concentration can cause a 300-fold increase in chroma and can change the hue and value as well. It is hypothesized that this self-association is similar to intramolecular stacking and prevents nucleophilic attack and formation of the carbinol pseudo-base structure.

Separation of a single compound from a complex mixture of compounds is often technically challenging and often requires a large volume of starting material. To date, the currently available blue colorant compositions that are produced from natural sources have not been satisfactory for commercial use in food products, either because of their color properties, or due to the high cost of their production. Additionally, the amount of fruit or vegetable juice or extract needed to isolate a single anthocyanin of interest has proven to be impractical. Therefore, there remains a need for natural blue anthocyanin colorants that provide similar color characteristics as synthetic counterparts that can be produced in large quantities.

SUMMARY OF THE INVENTION

The presently disclosed subject matter relates to compositions natural and modified enzymes and their related use for catalyzing the hydrolysis of an ester in an anthocyanin compound. The anthocyanin may occur in a solution, e.g., a fruit or vegetable juice or extract, and the catalysis can produce a compound (e.g., Compound I) having desirable colorant properties.

In one aspect, the present disclosure provides a method for selectively converting one or more diacylated anthocyanins into a monoacylated anthocyanin product, the method including: a) providing a fruit or vegetable juice or extract including a diacylated anthocyanin or a mixture of anthocyanins, wherein the mixture of anthocyanins includes one or more diacylated anthocyanins and, optionally, one or more monoacylated anthocyanins; and b) subjecting the fruit or vegetable juice or extract to an enzymatic treatment by one or more enzymes, wherein the one or more enzymes selectively hydrolyzes the one or more diacylated anthocyanins into the monoacylated anthocyanin product.

In some embodiments, the fruit or vegetable juice or extract is red cabbage juice or extract. In some embodiments, the monoacylated anthocyanin product is Compound I having the following structure:

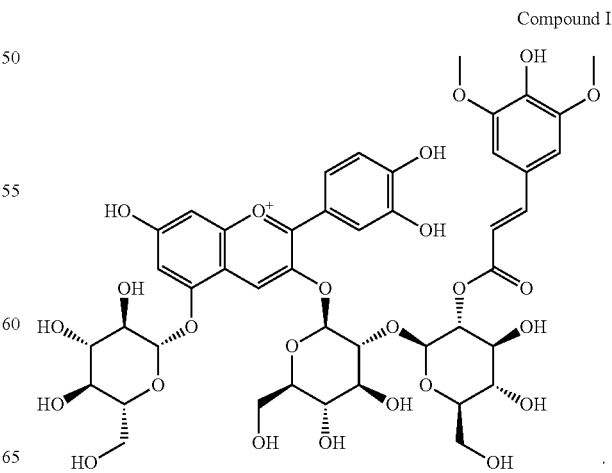

Compound I

In some embodiments, the mixture of anthocyanins comprises the one or more monoacylated anthocyanins, and the enzymatic treatment additionally converts the one or more monoacylated anthocyanins into a nonacylated anthocyanin product. In some embodiments, the nonacylated anthocyanin product is Compound II having the following structure:

Compound II

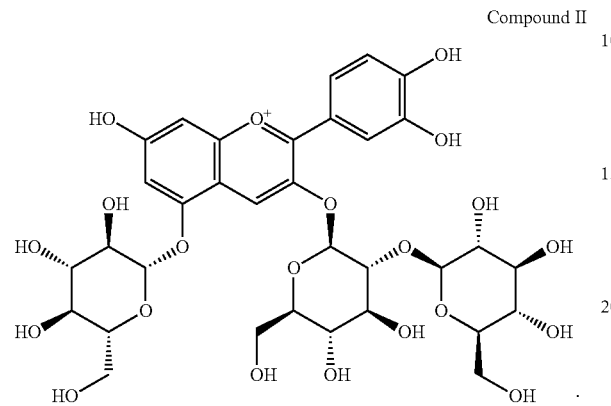

In further embodiments, the one or more enzymes comprises one or more esterases. The one or more esterases can be a naturally occurring esterase or a modified esterase.

In some embodiments, the naturally occurring esterase includes the amino acid sequence of any one of SEQ ID NO: 1-15. In some embodiments, the modified esterase is a modified carboxylesterase from Pseudomonas fluorescens. In some embodiments, the modified carboxylesterase from P. fluorescens includes one or more amino acid substitutions at position number 25, 28, 29, 30, 31, 38, 39, 63, 65, 70, 73, 200, or 201 relative to a naturally occurring carboxylesterase from P. fluorescens (e.g., the naturally occurring carboxylesterase from P. fluorescens of SEQ ID NO: 2).

In further embodiments, the one or more modified esterase is a modified carboxylesterase from Chromohalobacter salexigens. In some embodiments, the modified carboxylesterase from C. salexigens includes one or more amino acid substitutions at amino acid position number 23, 28, 75, 115, 117, 119, 121, 122, 125, 129, 168, 171, 173, 202, 209, or 212 relative to a naturally occurring carboxylesterase from C. salexigens (e.g., the naturally occurring carboxylesterase from C. salexigens of SEQ ID NO: 1).

In some embodiments, the modified esterase includes the amino acid sequence of any one of SEQ ID NO: 16-43.

In some embodiments, the monoacylated anthocyanin product is Compound I, and Compound I is isolated from the solution following the enzymatic treatment. In some embodiments, Compound I is isolated by a purification process including one or more of enzyme precipitation, solid-phase extraction, and preparatory high performance liquid chromatography (HPLC). In some embodiments, Compound I is isolated by a purification process including sequentially performing the steps of: (i) enzyme precipitation; (ii) solid-phase extraction; and, optionally, (iii) preparatory HPLC, wherein the preparatory HPLC of step (iii) is performed if the solution includes two or more anthocyanins.

In another aspect, the present disclosure features a method of producing Compound I:

Compound I

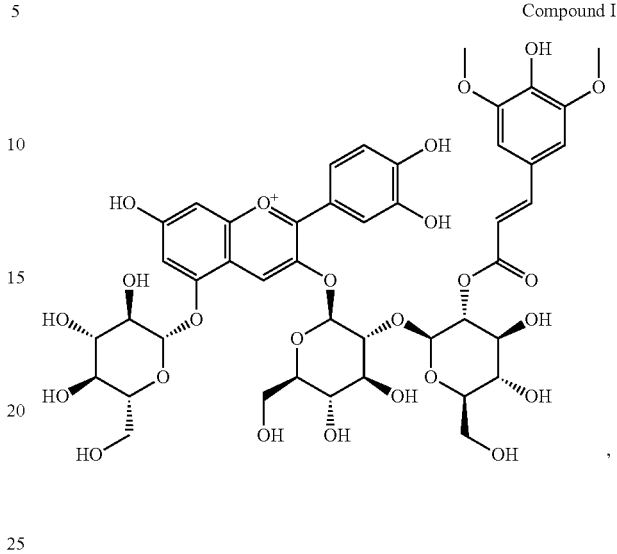

the method including contacting a solution including an anthocyanin with an enzyme, wherein the enzyme selectively hydrolyzes the anthocyanin to produce Compound I.

In some embodiments, the enzyme includes the amino acid sequence of any one of SEQ ID NO: 1-43. In some embodiments, the solution is contacted with two or more enzymes including the amino acid sequence of any one of SEQ ID NO: 1-43. In some embodiments, the solution is contacted with three or more enzymes including the amino acid sequence of any one of SEQ ID NO: 1-43. In further embodiments, the solution is contacted with four or more enzymes including the amino acid sequence of any one of SEQ ID NO: 1-43.

In some embodiments, the anthocyanin has the structure of Formula 1:

Formula 1

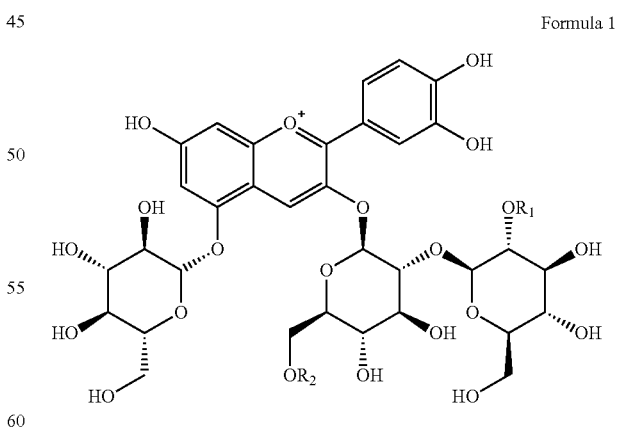

wherein $R_1$ is H or an acyl group and $R_2$ is an acyl group that is the same or different from the acyl group of $R_1$. In certain embodiments, the enzyme selectively hydrolyzes the anthocyanin to remove the acyl group of $R_2$. In some embodiments, the acyl group of $R_1$ and/or $R_2$ can be described by the structure

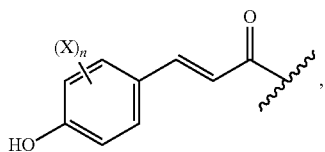

wherein X is a $C_{1-4}$ alkoxy group, and n is an integer from 0-2.

In further embodiments, the solution is a fruit or vegetable juice or extract, e.g., red cabbage juice or extract. In some embodiments, Compound I is present in an amount of from about 40% to about 100% by weight of a total anthocyanin content of the solution at least about 24 hours after the solution is contacted with the enzyme.

In another aspect, the present disclosure features a method of selectively hydrolyzing an anthocyanin of Formula 1:

Formula 1

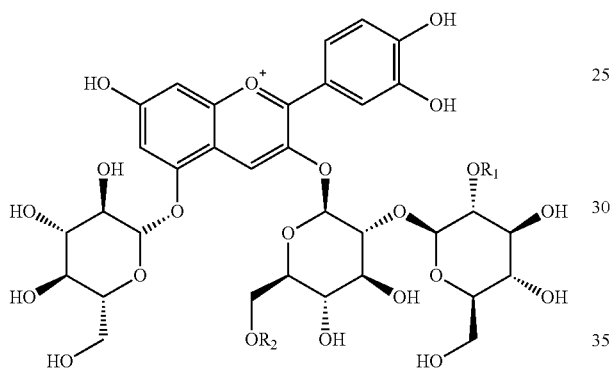

wherein $R_1$ is H or an acyl group, and $R_2$ is an acyl group that is the same or different from the acyl group of $R_1$; the method including contacting a solution including the anthocyanin of Formula 1 with an enzyme, wherein the enzyme selectively hydrolyzes the anthocyanin to remove the acyl group of $R_2$ and does not remove $R_1$. In some embodiments, the acyl group of $R_1$ and/or $R_2$ can be described by the structure

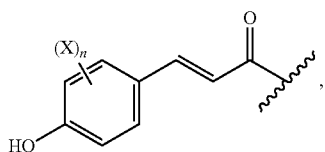

wherein X is a $C_{1-4}$ alkoxy group, and n is an integer from 0-2.

In some embodiments, the enzyme includes the amino acid sequence of any one of SEQ ID NO: 1-43. In some embodiments, the solution is contacted with two or more enzymes including the amino acid sequence of any one of SEQ ID NO: 1-43. In some embodiments, the solution is contacted with three or more enzymes including the amino acid sequence of any one of SEQ ID NO: 1-43. In further embodiments, the solution is contacted with four or more enzymes including the amino acid sequence of any one of SEQ ID NO: 1-43.

In some embodiments, the solution is a fruit or vegetable juice or extract. In some embodiments, the solution is red cabbage juice or extract.

In further embodiments, the selective hydrolysis produces Compound I and/or Compound II. In some embodiments, Compound I is present in an amount of from about 40% to about 100% by weight of a total anthocyanin content of the solution at least about 24 hours after the solution is contacted with the enzyme.

In some embodiments of any of the preceding methods, Compound I is isolated from the solution following the selective hydrolysis. In some embodiments, Compound I is isolated by a purification process including one or more of enzyme precipitation, solid-phase extraction, and preparatory HPLC. In certain embodiments, Compound I is isolated by a purification process including sequentially performing the steps of: (i) enzyme precipitation; (ii) solid-phase extraction; and, optionally, (iii) preparatory HPLC, wherein the preparatory HPLC of step (iii) is performed if the solution includes two or more anthocyanins.

In another aspect, the present disclosure features an edible colorant composition including: (a) a compound having the structure:

Compound I

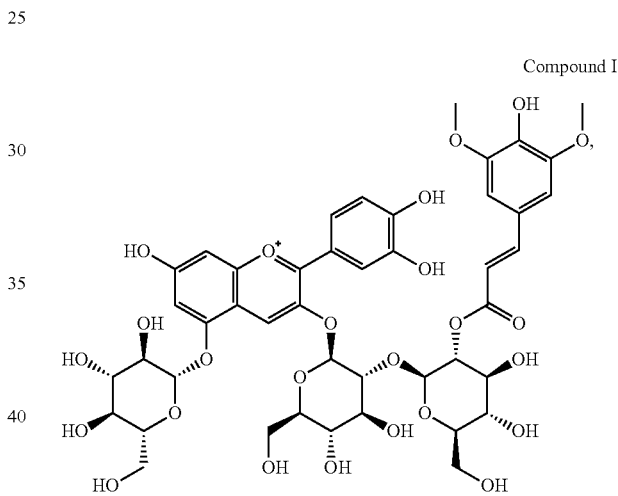

(b) a metal ion, wherein Compound I is prepared according to any one of the methods disclosed herein, e.g., by subjecting red cabbage juice or extract to an enzymatic treatment by one or more enzymes, and wherein the edible colorant composition is a solution having a pH of from about 6.0 to about 8.0.

In some embodiments of the edible colorant composition, the one or more enzymes includes one or more esterases. In some embodiments, the one or more esterase is a naturally occurring esterase, e.g., wherein the naturally occurring esterase includes the amino acid sequence of any one of SEQ ID NO: 1-15. In further embodiments, the one or more esterase is a modified esterase. In some embodiments, the modified esterase is a modified carboxylesterase from *P. fluorescens*. In some embodiments, the modified carboxylesterase from *P. fluorescens* includes one or more amino acid substitutions at position number 25, 28, 29, 30, 31, 38, 39, 63, 65, 70, 73, 200, or 201 relative to a naturally occurring carboxylesterase from *P. fluorescens*. In other embodiments, the modified esterase is a modified carboxylesterase from *C. salexigens*. In some embodiments, the modified carboxylesterase from *C. salexigens* includes one or more amino acid substitutions at amino acid position number 23, 28, 75, 115, 117, 119, 121, 122, 125, 129, 168, 171, 173, 202, 209, or 212 relative to a naturally occurring carboxylesterase from *C. salexigens*. In certain embodiments, the modified esterase includes the amino acid sequence of any one of SEQ ID NO: 16-43.

In further embodiments of the edible colorant compositions disclosed herein, Compound I is isolated from the red cabbage juice or extract following the enzymatic treatment. In some embodiments, Compound I is isolated by a purification process including one or more of enzyme precipitation, solid-phase extraction, and preparatory HPLC. In particular embodiments, Compound I is isolated by a purification process including sequentially performing the steps of: (i) enzyme precipitation; (ii) solid-phase extraction; and, optionally, (iii) preparatory HPLC, wherein the preparatory HPLC of step (iii) is performed if the solution includes two or more anthocyanins.

In some embodiments, the edible colorant composition is dried to produce a dry colorant composition. In some embodiments, the edible colorant composition is blue. In particular embodiments, the edible colorant composition has a ΔE value of less than about 17 when compared to an aqueous solution of about 50 ppm to about 100 ppm FD&C Blue No. 1, e.g., wherein the ΔE value is from about 8 to about 10.

In further embodiments, the edible colorant composition is green. In some embodiments, the edible colorant composition further includes a non-artificial yellow colorant selected from the group consisting of safflower, turmeric, beta carotene, and gardenia yellow.

In some embodiments of any of the edible colorant compositions of the present disclosure, the edible colorant composition includes from about 0.5% to about 30% (weight/weight (w/w)) of Compound I. In some embodiments, the edible colorant composition includes from about 0.5% to about 10% (w/w) of Compound I. In some embodiments, the edible colorant composition includes from about 10% to about 30% (w/w) of Compound I. In some embodiments, Compound I is present in an amount greater than about 10% of an anthocyanin chromophore content in the edible colorant composition.

In further embodiments of any of the edible colorant compositions of the present disclosure, the edible colorant composition includes from about 0.3 to about 1.0 molar equivalents of the metal ion to the monoacylated anthocyanin compound. In some embodiments, the metal ion is selected from the group consisting of aluminum ($Al^{3+}$), ferric ($Fe^{3+}$), or ferrous ($Fe^{2+}$) ions.

In another aspect, the present disclosure features an edible product comprising an edible colorant composition of the present disclosure.

In some embodiments, the edible product is a confectionery product. In further embodiments, the edible colorant composition is present in a coating applied to a surface of the confectionery product. In other embodiments, the confectionery product is a confectionery center with a soft-panned or hard-panned sugar-based coating. In some embodiments, the confectionery product is a confectionery center with a soft-panned or hard-panned polyol coating.

In some embodiments, the edible product includes from about 0.0001 to about 10% (w/w) of Compound I. In further embodiments, the edible product includes from about 0.0005 to about 1% (w/w) of Compound I. In further embodiments, the edible product includes from about 0.001 to about 0.5% (w/w) of Compound I.

In another aspect, the present disclosure features an enzyme including the amino acid sequence of any one of SEQ ID NO: 16-43.

In another aspect, the present disclosure features an enzyme including an amino acid sequence including at least one amino acid substitution relative to the amino acid sequence of any one of SEQ ID NO: 1-15. In some embodiments, the enzyme includes an active site motif having at least about 85% (e.g., about 86%, about 87%, about 88%, about 89%, about 90%, about 91%, about 92%, about 93%, about 94%, about 95%, about 96%, about 97%, about 98%, about 99%, or 100%) sequence identity relative to an active site motif of any one of SEQ ID NO: 1-15. In some embodiments, the enzyme includes at least one amino acid substitution relative to the amino acid sequence of SEQ ID NO: 1. For example, the enzyme includes at least one amino acid substitution at amino acid position number 23, 28, 75, 115, 117, 119, 121, 122, 125, 129, 168, 171, 173, 202, 209, or 212 of SEQ ID NO: 1. In other embodiments, the enzyme includes at least one amino acid substitution relative to the amino acid sequence of SEQ ID NO: 2. For example, the enzyme includes at least one amino acid substitution at amino acid position number 25, 28, 29, 30, 31, 38, 39, 63, 65, 70, 73, 200, or 201 of SEQ ID NO: 2. In certain embodiments, the enzyme includes an amino acid substitution at amino acid position number 73 of SEQ ID NO: 2. In particular embodiments, the amino acid substitution at amino acid position number 73 of SEQ ID NO: 2 is a methionine to histidine amino acid substitution.

The foregoing has outlined broadly the features and technical advantages of the present application in order that the detailed description that follows may be better understood. Additional features and advantages of the application will be described hereinafter which form the subject of the claims of the application. It should be appreciated by those skilled in the art that the conception and specific embodiments disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to the organization and method of operation, together with further objects and advantages, will be better understood from the following description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
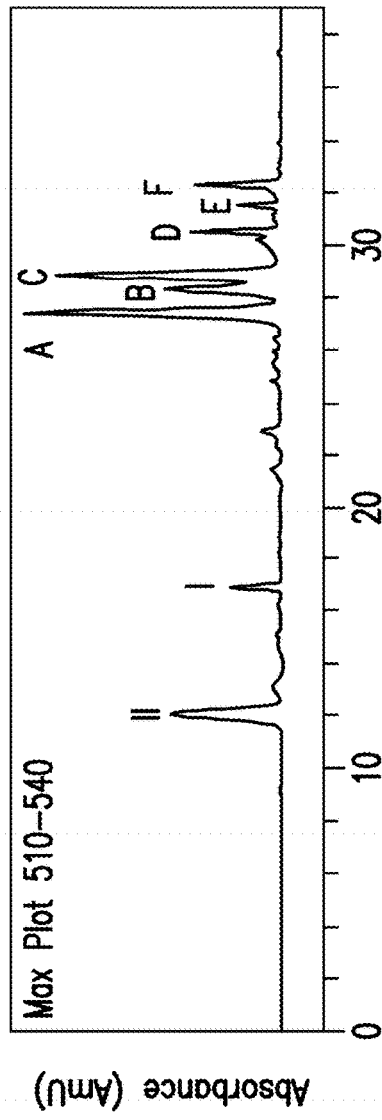
FIG. 1A provides high performance liquid chromatography (HPLC) data for red cabbage juice. Each peak corresponds to one of Compounds I, II, A, B, C, D, E, or F, as labeled in the figure.

The presently disclosed subject matter relates to, inter alia, an enzymatic treatment that converts one or more anthocyanin naturally occurring in a fruit or vegetable juice or extract into an anthocyanin molecule having desirable colorant properties, i.e., Compound I. The enzymes disclosed herein catalyze the cleavage of one or more chemical bonds in an anthocyanin, e.g., one or more acyl groups in an anthocyanin. Enzymatic treatment of a solution containing a mixture of anthocyanins, such as a fruit or vegetable juice or extract, results in the increase in the amount of one or more specific anthocyanins in the mixture, i.e., Compound I and/or Compound II. The desired compounds, i.e., Compound I, can then be separated from the other compounds, i.e., Compound II, in the solution following enzymatic treatment.

Further disclosed herein are methods for the preparation of the enzymes used in the disclosed enzymatic treatment, as well as methods for the separation and isolation of anthocyanins from a solution including a mixture of anthocyanins. Additionally, the disclosed subject matter provides for the use of an anthocyanin as a colorant in edible food products.

1. Definitions

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art.

As used herein, the term "anthocyanin" refers to a water soluble pigment that is generally red, purple or blue, depending on the pH of a solution including the anthocyanin. Anthocyanins are the glucosides of anthocyanidins. Anthocyanidins are generally flavylium cation derivatives of anthocyanins (devoid of the sugar moieties) and can include aurantinidin, cyanidin, dephininidin, europinidin, luteolinidin, pelargonidin, malvidin, peonidin, petunidin and rosinidin, for example. Cyanidin is the exemplary anthocyanidin.

As used herein, the term "acylated anthocyanin" refers to an anthocyanin molecule having one or more acyl molecules esterified to one or more sugar molecules that are attached to the anthocyanidin. Acyl molecules or groups can include cinnamate derivative and or hydroxyl benzoyl derivatives. Cinnamate derivatives can include ferulic, para coumaric or sinapic groups. Sinapic is the exemplary acyl group.

As used herein, the term "monoacylated anthocyanin" refers to an anthocyanin molecule that includes one acyl group linked by an ester bond to a sugar group of the anthocyanin molecule.

As used herein, the term "diacylated anthocyanin" refers to an anthocyanin molecule that includes two acyl groups linked by ester bonds to one or more sugar groups of the anthocyanin molecule.

As used herein, "sugar syrup" refers to a liquid material comprising at least a sugar and water. In certain embodiments, a sugar syrup can include a syrup where a sugar is dissolved in the water in an amount of at least about 60% sugar solids by weight of the syrup. In certain embodiments, other components can also be present within the sugar syrup. For example, and not by way of limitation, an edible colorant composition of the present disclosure can be used in a sugar syrup, e.g., to add a color to the sugar syrup.

As used herein, "coating layer" refers to a layer obtained by one application of a coating material, e.g., a sugar syrup, to a substrate, e.g., a food product, being coated and which is dried and crystallized.

As used herein, "coating" refers to the total amount of coating material, e.g., one or more sugar syrups, applied to a substrate, e.g., a food product, which is dried and crystallized after each application, upon completion of a coating process. In certain embodiments, the coating process can include one or more steps of applying a coating material and drying and crystallizing each applied coating layer, e.g., a sugar syrup containing one or more colorant compositions of the present disclosure, to the substrate.

As used herein, the term "colorant" refers to any substance that imparts color by absorbing or scattering light at different wavelengths.

As used herein, the term "colorant composition" refers to any composition that imparts color by absorbing or scattering light at different wavelengths.

As used herein, the term "non-artificial colorant" refers to any substance that exists in or is produced by nature, or is obtained from a non-artificial source. In certain embodiments, the term "non-artificial colorant" refers to a colorant that comprises one of more anthocyanins obtained from a non-artificial source, e.g., a vegetable, a plant, or a flower (or a flower petal).

As used herein, the term "non-artificial colorant composition" refers to any composition that comprises a colorant that exists in or is produced by nature or is obtained from a non-artificial source. In certain embodiments, the term "non-artificial colorant composition" refers to a colorant composition that comprises one of more anthocyanins obtained from a non-artificial source, e.g., a vegetable, a plant, or a flower (or a flower petal).

As used herein, "confectionery product" or "confection" refers to a sweet or candy food product. Non-limiting examples of confectionery products include cakes, cookies, pies, candies, chocolates, chewing gums, gelatins, ice creams, puddings, jams, jellies, and other condiments, cereal, and other breakfast foods, canned fruits and fruit sauces. As used herein, the confectionery products having neutral pH (e.g., about pH 5-8 or from about pH 6 to about pH 8) are particularly suitable for the colorant compositions disclosed herein.

As used herein, "maximum absorbance," "lambda max," or "$\lambda_{max}$," refers to the wavelength in nanometers at which the maximum fraction of light is absorbed by a substance, colorant and/or colorant composition.

As used herein, "FD&C Blue No. 1" includes the various names given to the identical artificial blue colorant, Brilliant Blue FCF and European Commission E133. The lambda max of FD&C Blue No. 1 is 630 nm. FD&C Blue No. 1 is used interchangeably with Cyan Blue or FD&C Blue No. 1.

As used interchangeably herein, the terms "color" and "color characteristics" refer to the color properties such as hue, chroma, purity, saturation, intensity, vividness, value, lightness, brightness and darkness, and color model system parameters used to describe these properties, such as Commission Internationale de l'Eclairage CIE 1976 CIELAB color space L*a*b* values and CIELCH color space L*C*h° values. The CIELAB and CIELCH color models provide more perceptually uniform color spaces than earlier color models. In certain embodiments, the colorants of the present disclosure can be analyzed with a spectrophotometer, and CIELAB L*a*b* and CIELCH L*C*h° values can be calculated from the spectral data, as described in greater detail below. The L*a*b* and L*C*h° values provide a means of representing color characteristics and assessing the magnitude of difference between two colors. Methods for determining the CIELAB and CIELCH values of colorants are disclosed in International Patent Publication Nos. WO 2014/150230 and WO 2014/152417, the contents of which are hereby incorporated by reference in their entireties. CIELAB color space L*a*b values and CIELCH color space L*C*h values can be expressed using three-dimensional representations and also two-dimensional representations where the $3^{rd}$ dimension is fixed. An example of the latter is a two-dimensional cross-sectional representation of the L*a*b* space at a specific L* value, for example at L*=50. Such a representation allows a useful display of colorants in the a*b* space with the caveat that some points are actually above, on or below the plane shown. The L* value is typically chosen to be at a suitable midpoint between the data points being shown.

The L*a*b* and L*C*h° values also provide a means of representing color characteristics and assessing the magnitude of difference between two colors not only of solutions, but also of products. Measurements of products are accomplished using reflectance measurements from the surface of the product, for example, the surface of a hard panned confection. In the case of reflectance measurements, the L*a*b* and L*C*h° values reported herein were calculated based on spectral data obtained with a Konica Minolta Spectrophotometer CM-3500d operated in reflectance mode with a D65 illuminant and 10° observer angle.

The term "reflectance" as used herein with respect to a material is the percentage of any incident electromagnetic radiation that reflects back from a surface. Reflectance is a function of wavelength, and the reflectance of a material can vary across the electromagnetic spectrum. A material that is a perfect reflector at a particular wavelength has a reflectance of 100% at that wavelength.

As used herein, "hue" or "hue angle" refers to the color property that gives a color its name, for example, red, blue and violet.

As used herein, "chroma" is a color property indicating the purity of a color. In certain embodiments, a higher chroma is associated with greater purity of hue and less dilution by white, gray or black.

As used herein, "value" is a color property indicating the lightness or darkness of a color wherein a higher "value" is associated with greater lightness.

As used herein "admixing," for example, "admixing a colorant composition of the present disclosure with a food product," refers to a method where a colorant composition of the present disclosure is mixed with or added to the completed product or mixed with some or all of the components of the product during product formation or some combination of these steps. When used in the context of admixing the term "product" refers to the product or any of its components. Admixing can include a process that includes adding the colorant composition to the product, spraying the colorant composition on the product, coating the colorant composition on the product, painting the colorant composition on the product, pasting the colorant composition on the product, encapsulating the product with the colorant composition, mixing the colorant composition with the product or any combination thereof. The colorant compositions, e.g., those that are admixed with the product, can be a liquid, dry powder, spray, paste, suspension or any combination thereof. In certain embodiments, the term "admixing" can refer to mixing Compound I as disclosed herein with one or more additional components to create a finished colorant.

As used herein, "solution," refers to a liquid mixture in which the minor component (the solute) is uniformly distributed within the major component (the solvent). For example, a monoacylated anthocyanin compound (Compound I) is distributed within a solution, such as a sugar syrup, to yield a blue colored coating on a confectionery substrate.

As used herein, the phrase "consumer product" or "end product" refers to composition that is in a form ready for use by the consumer for the marketed indication. A solvent suitable for use in a consumer product is a solvent that, when combined with other components of the end product, will not render the consumer product unfit for its intended consumer use.

As used herein, the term "esterase" refers to an enzyme that catalyzes the hydrolysis of an ester into an acid and an alcohol. A "modified esterase" refers to an esterase that includes modifications, e.g., one or more amino acid substitutions, relative to a naturally occurring esterase.

As used herein, the term "extract" refers to substance made by extracting a part of a raw material, such as a fruit or vegetable, by using a solvent such as but not limited to ethanol or water.

As used herein, "food grade," refers to any substance, metal ion and/or colorant composition that is of a grade acceptable for use in edible food products.

As used herein, "food product" refers to an ingestible product, such as, but not limited to, human food, animal foods and pharmaceutical compositions.

2. Anthocyanins and Their Color Properties

The present disclosure relates to the use of an anthocyanin colorant, i.e., Compound I, for use in an edible colorant composition, as well as edible food products containing the edible colorant composition. Compound I can be formed by enzymatic treatment with an enzyme as described herein of a solution including an anthocyanin or a mixture of anthocyanins, such as those naturally occurring in a fruit or vegetable juice or extract. The disclosed enzymes catalyze the hydrolysis of an ester bond to remove an acyl group from an anthocyanin, thereby resulting in the production of Compound I. Enzymatic treatment of a solution including a mixture of anthocyanins also results in the reduction of the total number of anthocyanins present in the solution, e.g., a fruit or vegetable juice or extract, thereby allowing for simplified purification of Compound I from the solution.

2.1. Anthocyanins

The anthocyanins of the present disclosure can be obtained from natural sources and/or juices or extracts thereof. For example, and not by way of limitation, the anthocyanins of the present disclosure can be obtained from vegetables (or extracts or juices thereof) such as red cabbage, purple sweet potato, red potato, blue potato, red radish, black carrot, purple carrot, purple corn, red corn, red onion, purple broccoli, red broccoli, purple cauliflower, rhubarb, black bean, red leaf lettuce, black rice, eggplant or combinations thereof. In certain embodiments, the anthocyanins can be obtained from fruits (including extracts or juices thereof) such as, but not limited to, strawberry, raspberry, cranberry, lingonberry, red grape, apple, black currant, red currant, cherry, blueberry, elderberry, bilberry, crowberry, blackberry, chokeberry, gooseberry, acai, nectarine, peach, plum, blood orange, blue tomato or combinations thereof. In certain embodiments, the anthocyanins of the present disclosure can be obtained from flower petals (including extracts or juices thereof) such as those of "Heavenly Blue" Morning Glory, "Better Times" Rose or combinations thereof.

In certain embodiments, a vegetable, fruit, and flower petal juice can be obtained by pressing liquid out of the fruit, vegetable, or flower. In certain embodiments, a vegetable, fruit, and flower petal extract can be obtained by washing a macerated fruit, vegetable, or flower with a solvent (e.g., water or alcohol). Juices and extract can contain anthocyanins as well as other naturally occurring compounds, including, for example, carbohydrates, acids, flavonoids, metal ions, phenolic acids, phenolic acid esters, and vitamins.

In certain embodiments, vegetable, fruit, and flower petal juices or extracts can include processed juices and extracts. Non-limiting examples of processed juices and extracts include reconstituted juices and extracts, deodorized juices and extracts, and juices and extracts subjected to other processes for removing specific or broad classes of compounds. In certain embodiments, the present disclosure is directed to enzymatic treatment of anthocyanins derived from red cabbage extracts, e.g., from red cabbage juice.

Figure 1B:
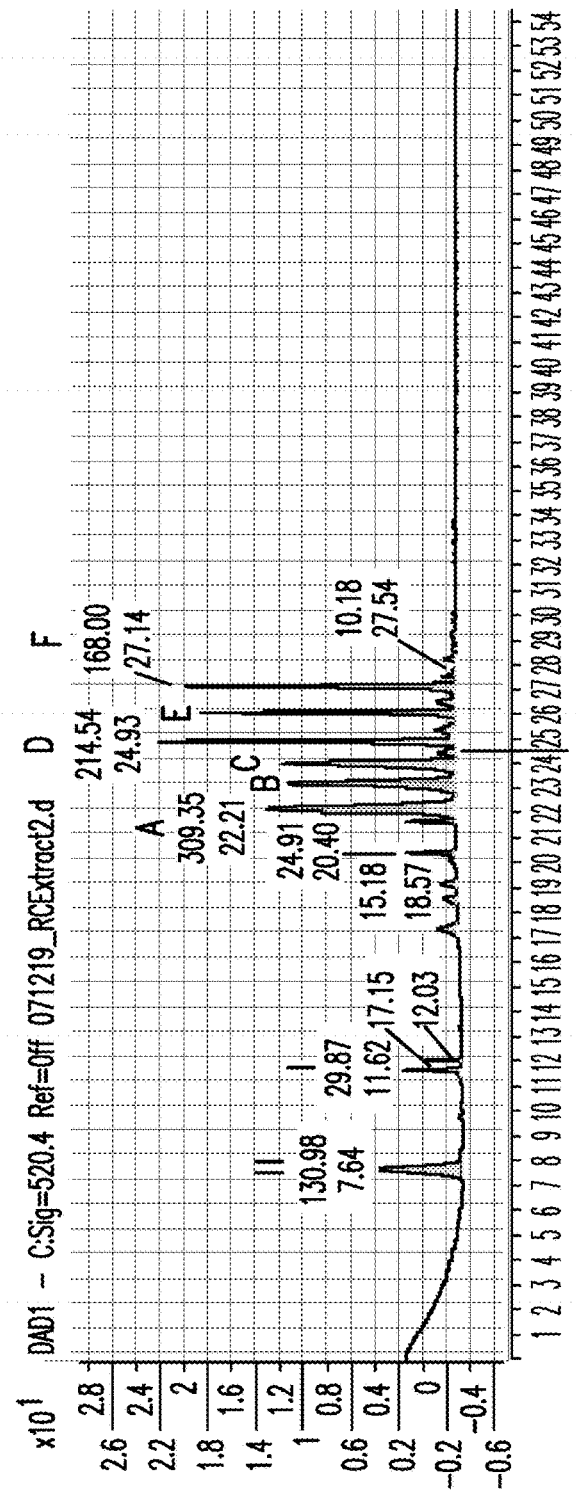
FIG. 1B provides liquid chromatography-mass spectrometry (LC-MS) data for red cabbage juice. Each peak corresponds to one of Compounds I, II, A, B, C, D, E, or F, as labeled in the figure. The area under each curve is provided below in Table 2.
Figure 2:
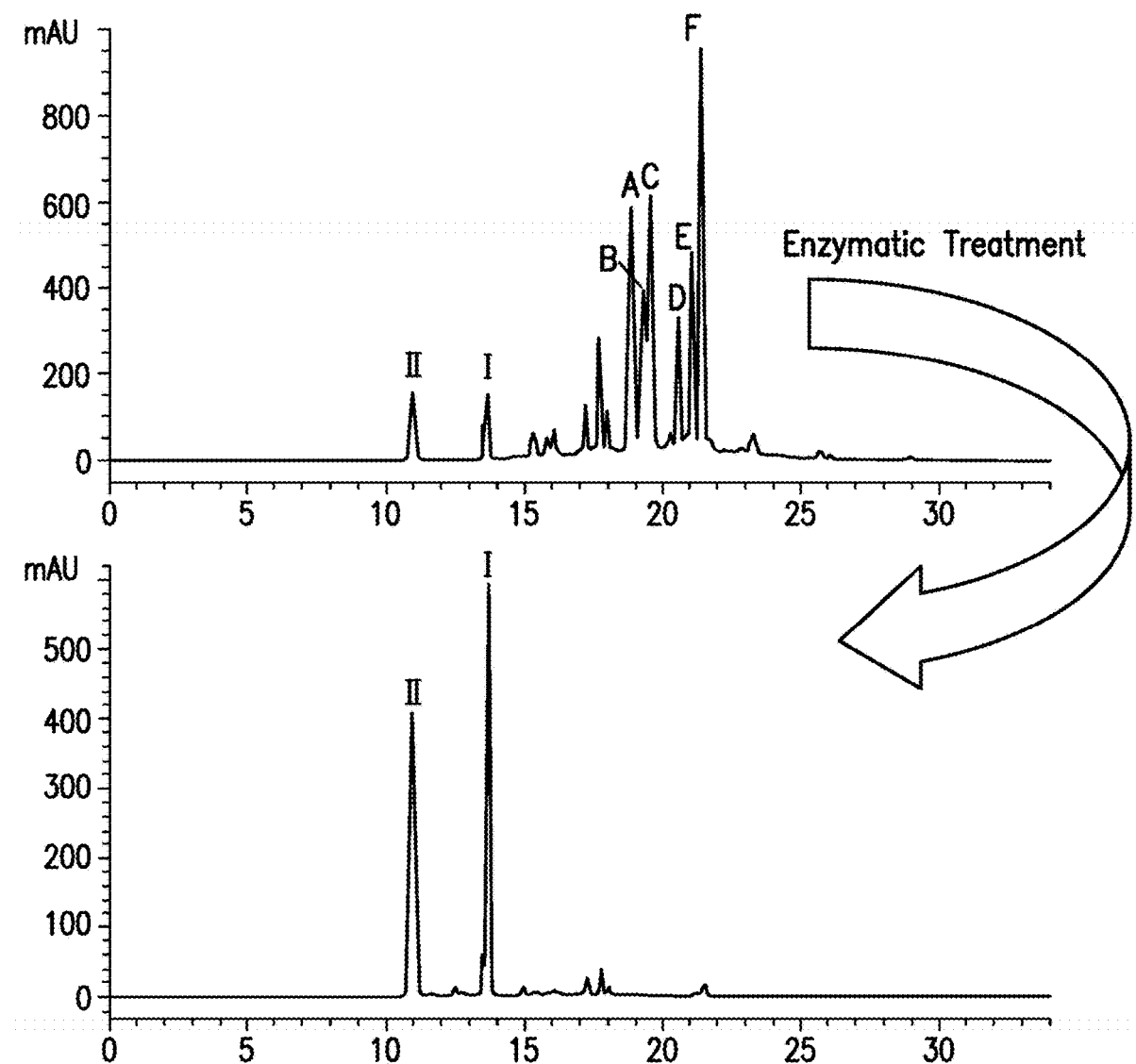
FIG. 2 provides a comparison of LC-MS data for red cabbage juice before and after enzymatic treatment.

Red cabbage juice contains a wide variety of compounds and anthocyanins as can be seen in the HPLC and LC-MS data shown in FIGS. 1A and 1B. Eight anthocyanins, referred to herein as Compounds I, II, and A-F, have been identified as naturally occurring in red cabbage juice or extract. The structures of these anthocyanins can be generally described by Formula 1:

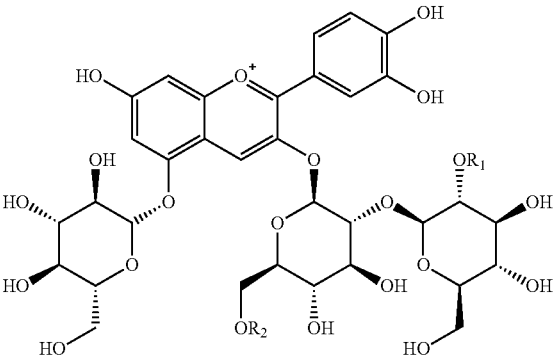

Formula 1 wherein each of $R_1$ and $R_2$ is, independently, H or an acyl group. An acyl group is generally represented by the formula R—C=O. For example, when $R_1$ and/or $R_2$ is an acyl group, the acyl group can have the structure of

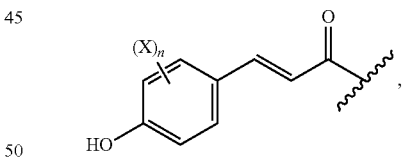

wherein X is a $C_{1-4}$ alkoxy group and n is an integer from 0-2. In some embodiments, X is a methoxy group. In some embodiments, n is 0, 1, or 2. In some embodiments, each of $R_1$ and $R_2$ is, independently, a para coumaric group, a ferulic group, or a sinapic group.

Compound II is a non-acylated anthocyanin, wherein $R_1$ and $R_2$ are both H; Compound I and Compounds A-C are monoacylated anthocyanins, i.e., wherein $R_1$ is H and $R_2$ is an acyl group selected from a para coumaric group, a ferulic group, or a sinapic group; and Compounds D-F are diacylated anthocyanins, i.e., wherein each of $R_1$ and $R_2$ is an acyl group selected from a para coumaric group, a ferulic group, or a sinapic group. The chemical structures of these compounds are provided below:

Compound A
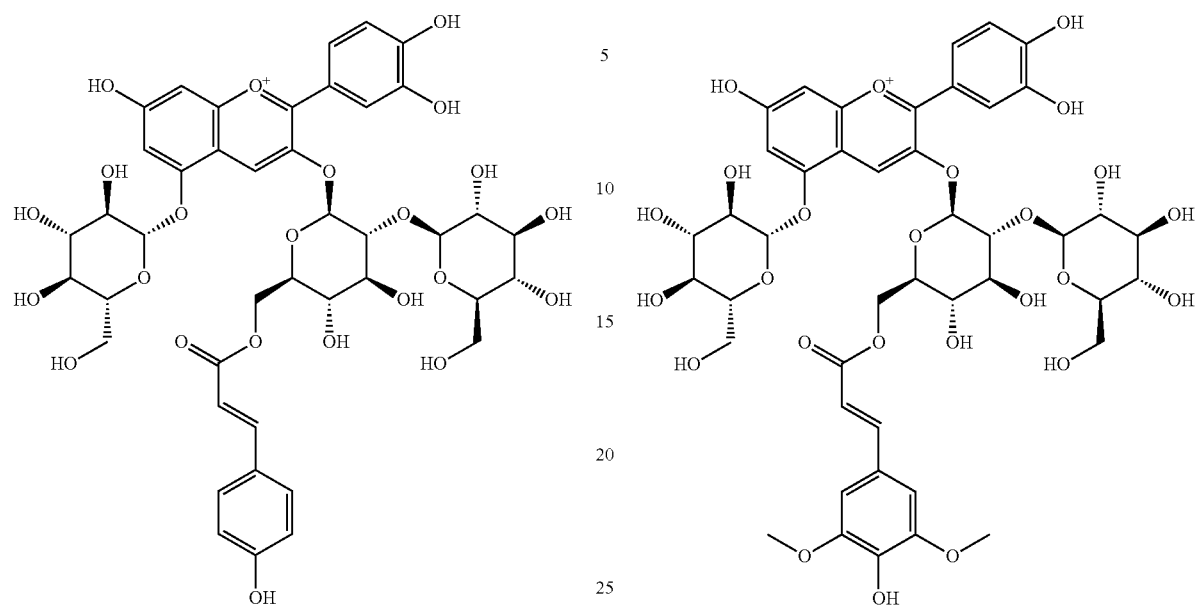
Compound C
Compound B
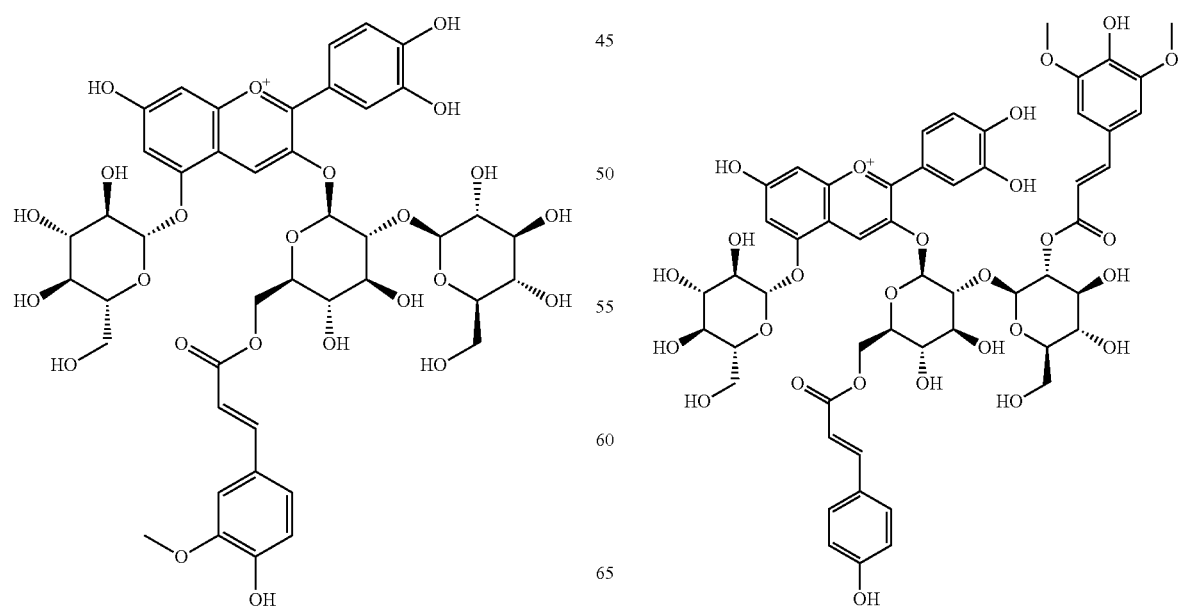
Compound D

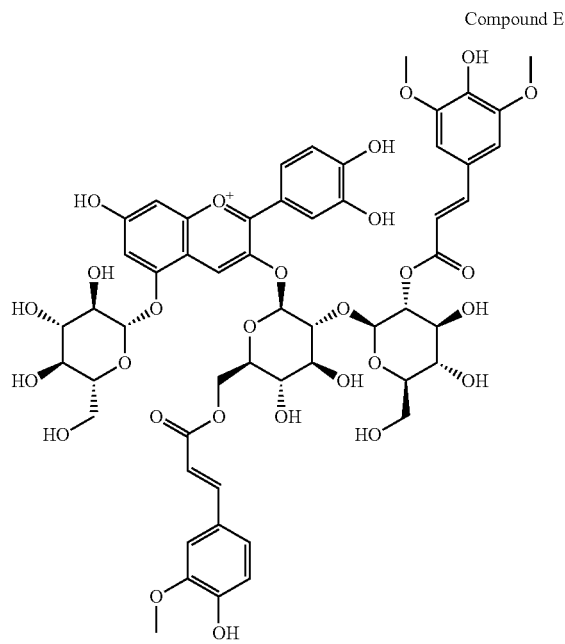

Compound E

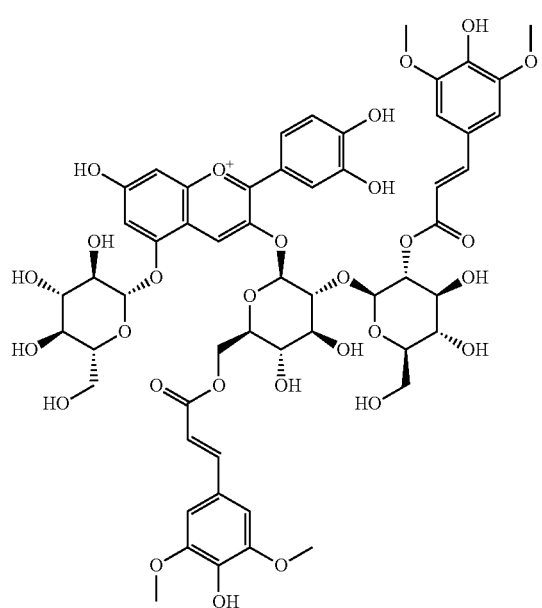

Compound F

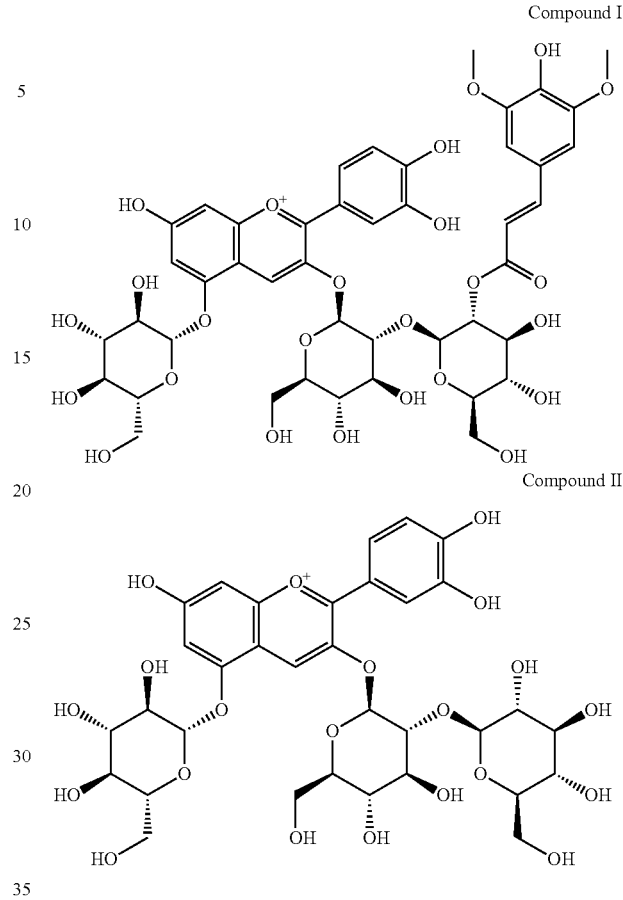

Compound I

Compound II

Compounds A-C have the same base structure as Compound II but include a single additional acyl group, such as a ferulic, a para coumaric, or a sinapic group, at the $R_2$ position. Similarly, Compounds D-F have the same base structure as Compound I, but further include an additional acyl group, such as a ferulic, a para coumaric, or a sinapic group, at the $R_2$ position. The LC-MS data and identity of Compounds I, II, and A-F are provided in Table 1.

TABLE 1

Anthocyanins present in Red Cabbage Juice

| Compound | RT (mm) | λvis (nm) | λacyl (nm) | $M^+$ | $R_1$ | $R_2$ |
|---|---|---|---|---|---|---|
| II | 12.1 | 513 | — | 773 (287) | H | H |
| I | 17.0 | 528 | 334 | 979 (287) | Sinapic | H |
| A | 27.4 | 523 | 313 | 919 (287) | H | p-Coumeric |
| B | 28.3 | 523 | 326 | 949 (287) | H | Ferulic |
| C | 28.9 | 524 | 329 | 979 (287) | H | Sinapic |
| D | 30.5 | 536 | 319 | 1125 (287) | Sinapic | p-Coumeric |
| E | 31.6 | 536 | 330 | 1155 (287) | Sinapic | Ferulic |
| F | 32.3 | 536 | 331 | 1185 (287) | Sinapic | Sinapic |

In certain embodiments, the present disclosure is directed to preparation and isolation of Compound I. The chemical name of Compound I is 3-O-(2-O-(2-O-(E)-sinapoyl-β-D-glucopyranosyl)-β-D-glucopyranosyl)-5-O-β-D-glucopyranosylcyanidin. Compound I is a monoacylated anthocyanin that demonstrates a unique ability to generate a cyan blue hue under certain conditions. It is a minor component of red cabbage juice or extract. Red cabbage juice or extract naturally only comprises from about 1% to about 4% of Compound I. The HPLC spectrum of FIG. 1A and Table 2 below show the percentage amounts of each of Compounds I, II, and A-F in one exemplary extract of red cabbage juice. In this example, Compound I is only present in an amount of about 2%.

TABLE 2

Composition of Red Cabbage Juice

| Peak (Compound) | Area | % of Total Area |
|---|---|---|
| II | 130.98 | 8.85 |
| I | 29.87 | 2.02 |
| A | 309.35 | 20.91 |
| B | 237.86 | 16.07 |
| C | 233.81 | 15.80 |
| D | 214.54 | 14.50 |
| E | 155.29 | 10.49 |
| F | 168.00 | 11.35 |
| Total | 1479.70 | |

Figure 3A:
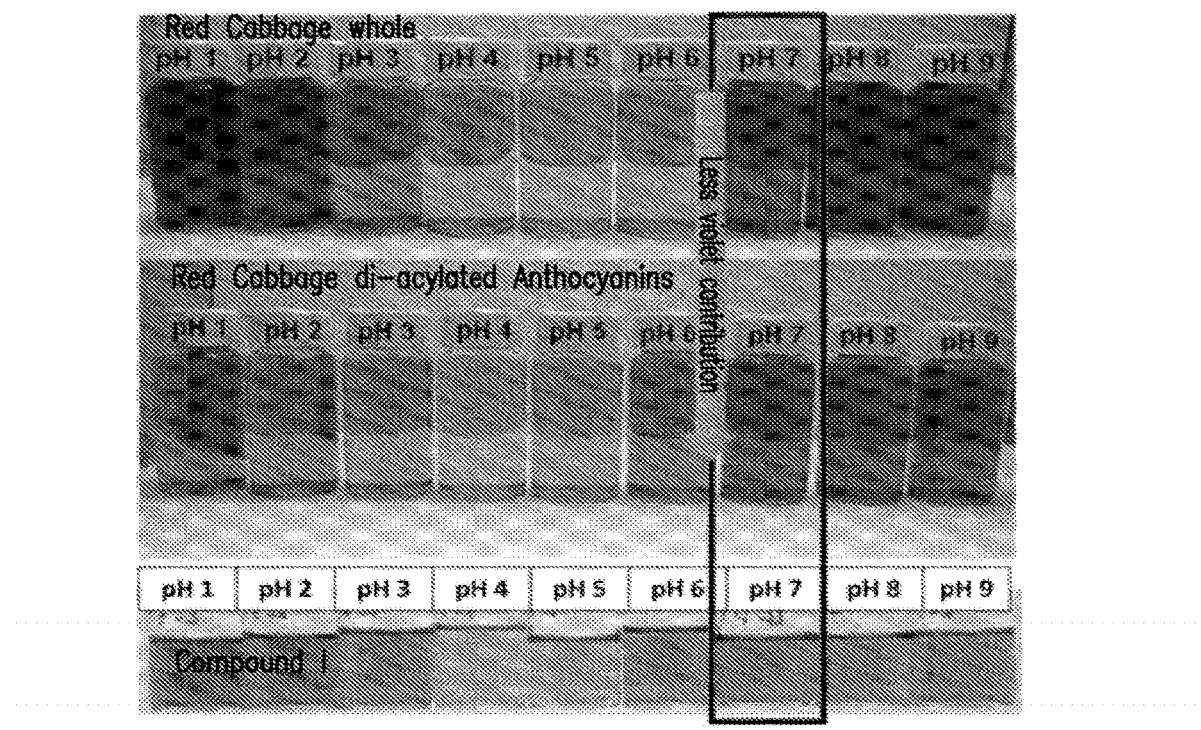
FIG. 3A provides a comparison of the colors provided by whole red cabbage extracts, red cabbage diacylated fraction and Compound I plus metal ion in aqueous solution at pH values ranging from 1 to 9, which demonstrates the lower violet color contribution, e.g., at pH 7.
Figure 3B:
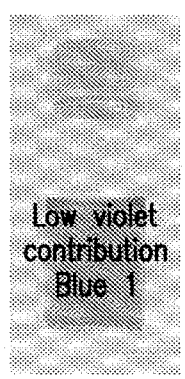
FIG. 3B provides a visual comparison of the color provided by an FD&C Blue No. 1 (Blue 1) extract in aqueous solution.
Figure 3C:
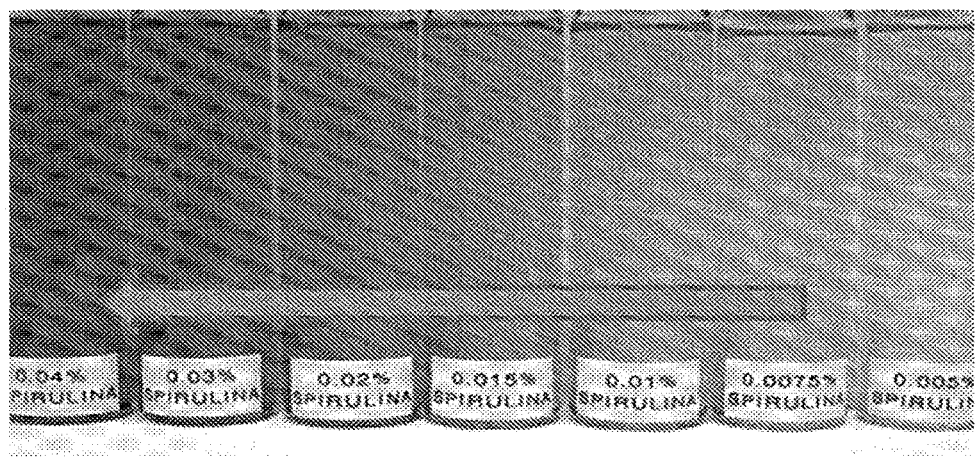
FIG. 3C provides a visual comparison of the colors provided by Spirulina Blue extracts in aqueous solution at concentrations from 0.005% to 0.04%.

Color characteristics of Compound I can change in the presence of a metal ion in a solution thereof. For instance, a colorant comprising Compound I and about 1.0 molar equivalents or about 0.3 molar equivalents of a metal ion (such as $Al^{3+}$ or $Fe^{3+}$) at about pH 5 to 8 surprisingly has less of a violet hue (i.e., lower violet contribution) than red cabbage juice at about pH 7 or 8, the diacylated anthocyanin fraction of red cabbage juice at about pH 7 or 8, and Spirulina Blue. A comparison of the color at about pH 7 for red cabbage, di-acylated red cabbage anthocyanin fraction (Compounds D-F) and Compound I with a metal ion is provided in FIG. 3A. FIG. 3A illustrates that violet contribution in the Compound I solution with metal ion is significantly reduced. By comparison, the violet contribution is higher for the Spirulina Blue solution, and the violet contribution even increases as the concentration of Spirulina Blue is increased (FIG. 3C). The solution of Compound I with metal ion is the closest to a solution of FD&C Blue No. 1 (FIG. 3B) in having a low violet contribution. Solutions of Compound I with metal ion are particularly unique in demonstrating hue angle, wavelength, and a* and b* values comparable to those of solutions of FD&C Blue No. 1.

A colorant comprising Compound I and a metal ion at about pH 5 to 8 provides significantly less violet hue in its blue color, which is critical when blending with a non-artificial yellow color to produce a bright and true green color. Other non-artificial blue colorants having a significant violet hue tend to produce undesirable green colors when mixed with non-artificial yellow colorants. These undesirable green colors are typically characterized as being a muddy green or olive-green color.

2.2 Colorant Compositions

An anthocyanin as disclosed herein, i.e., Compound I, can be used in a colorant composition. In certain embodiments, a colorant composition of the present disclosure can be a cyan blue colorant composition that includes, e.g., Compound I with a metal ion at a pH of about 6 to about 8.

In certain embodiments, one or more of the colorant compositions of the present disclosure can be added to a food product, in an amount effective to increase, enhance and/or modify the color characteristics of a food product or portion thereof. For example, and not by way of limitation, a colorant composition of the present disclosure can enhance the blue color characteristics of the food product (or portion thereof). In certain embodiments, colorant compositions of the present disclosure can be used to increase, enhance and/or modify the color characteristics of a food product (or portion thereof), such as, but not limited to, a chocolate confection. In certain embodiments, the colorant composition is a liquid. In other embodiments, the colorant composition is a solid created, for example, by drying a liquid colorant composition.

In certain embodiments, the colorant composition of the present disclosure comprises Compound I. In certain embodiments, the colorant composition comprises from about 0.005% to about 100%, or from about 0.005% to about 80%, or from about 0.005% to about 60%, or from about 0.005% to about 50%, or from about 0.005% to about 40%, or from about 0.005% to about 30%, or from about 0.005% to about 20%, or from about 0.005% to about 10%, or from about 0.5% to about 30%, or from about 0.5% to about 5%, or from about 0.5% to about 15%, or from about 10% to about 25%, or from about 20% to about 30% by weight of Compound I. In certain embodiments, the colorant composition comprises from about 1% to about 80%, or from about 10% to about 70% by weight of the colorant composition, or from about 20% to about 60% by weight of Compound I. In certain embodiments, the colorant composition comprises from about 30% to about 50% by weight of Compound I. In certain embodiments, the colorant composition comprises from about 40% to about 50% by weight of Compound I. In certain embodiments, the colorant composition comprises from about 0.005% to about 10%, from about 0.005% to about 1%, or from about 0.005% to about 0.1% by weight of Compound I. In certain embodiments, the colorant composition comprises greater than about 0.5%, greater than about 1%, greater than about 5%, greater than about 10%, greater than about 15%, greater than about 20%, greater than about 25%, or greater than about 30% by weight of Compound I.

In certain embodiments, Compound I makes up greater than about 10% of the anthocyanin chromophore portion of a colorant, preferably greater than about 20%, preferably greater than about 30%, preferably greater than about 40%, preferably greater than about 50%, preferably greater than about 60%, preferably greater than about 70%, preferably greater than about 80%, preferably greater than about 90%, preferably greater than about 95%, and most preferably about 100% of the anthocyanin chromophore portion of a colorant. In further embodiments, Compound I is present in an amount of from about 0.05% to about 0.10% (w/w) (e.g., from about 0.05% to about 0.09% (w/w), from about 0.06% to about 0.08% (w/w), or from about 0.07% to about 0.1% (w/w)) of an anthocyanin chromophore content of the colorant composition. In other embodiments, Compound I is present in an amount of from about 5% to about 35% (w/w) (e.g., from about 5% to about 15% (w/w), from about 5% to about 20% (w/w), from about 5% to about 30% (w/w), from about 10% to about 25% (w/w), from about 10% to about 35% (w/w), from about 20% to about 35% (w/w)) of an anthocyanin chromophore content of the colorant composition.

2.3 pH

In certain embodiments, the pH of the colorant composition of the present disclosure comprises at least one pH adjusting ingredient. The pH of the colorant composition can be adjusted using food grade acids or bases (e.g., food grade sodium hydroxide) and/or the pH can be adjusted with the use of food grade buffers (e.g., phosphate buffer) or food grade acids or bases can be used in combination with food grade buffers to adjust pH.

Non-limiting examples of pH adjusting ingredients include potassium and sodium-based buffers. In certain embodiments, the pH adjusting ingredient can include potassium phosphate, sodium acetate, or other food grade buffers known in the art. Another pH adjustment component can be, for example, sodium hydroxide, which is a source of an alkali metal ion.

In certain embodiments, the colorant composition has a pH of about 5.0 to about 8.0. In certain embodiments, for a blue colorant composition, the pH can be from about 5.0 to about 8.0, or from about 6.0 to about 8.0, or from about 7.0 to about 8.0. In certain non-limiting embodiments, the pH of the pH adjusting ingredient present within a colorant composition, e.g., a blue colorant composition, is about 6.0. In certain embodiments, the pH of the pH adjusting ingredient present within a colorant composition, e.g., a blue colorant composition, is about 6.5. In certain embodiments, the pH of the pH adjusting ingredient present within a colorant composition, e.g., a blue colorant composition, is about 7.0. In certain embodiments, the pH of the pH adjusting ingredient present within a colorant composition, e.g., a blue colorant composition, is about 7.5. In certain embodiments, the pH of the pH adjusting ingredient present within a colorant composition, e.g., a blue colorant composition, is about 8.0.

2.4 Metal Ions

In certain embodiments of the present disclosure, the colorant composition further comprises at least one metal ion or cation or salt form thereof. In certain embodiments, the metal ion can bind to one or more hydroxyl groups present on the B-ring of the cyanidin chromophore portion of the anthocyanin molecule. Complexation of Compound I with a metal ion, such as $Al^{3+}$, causes a bathochromic shift in the color to produce the true cyan blue color of the color composition. Other exemplary metal ions that can cause a bathochromic shift to produce a true cyan blue color include $Fe^{2+}$ and $Fe^{3+}$, as well as other metal ions disclosed herein.

In certain embodiments, the metal ion is a multivalent metal ion such as, but not limited to, a divalent metal ion or a trivalent metal ion. A non-limiting example of a divalent cation include $Fe^{2+}$. In certain embodiments, the metal cation is a trivalent cation such as $Al^{3+}$ or $Fe^{3+}$. In certain embodiments, the metal ion is $Al^{3+}$. In certain embodiments, the metal ion is $Fe^{2+}$. In certain embodiments, the metal ion is $Fe^{3+}$.

In certain embodiments, the metal ion is present in the colorant composition as a metal salt. For example, and not by way of limitation, the metal salt is $AlCl_3$, $Al_2(SO_4)_3$, $FeCl_3$, or $FeCl_2$.

In certain embodiments, there can be a food grade metal ion or salt form thereof. In certain embodiments, the metal ion or salt form thereof can be selected to be suitable for use in an edible product, e.g., $Al^{3+}$ or $Fe^{3+}$.

In certain embodiments, the molar ratio of Compound I to metal ion is about 1:100, or about 1:10, or about 1:1, or about 1:0.5, or about 1:0.3, or about 1:0.25, or about 1:0.1, or about 1:0.01, or about 1:0.001, or about 1:0.1.

2.5 Combinations of Colorant Compositions

The present disclosure also provides for colorant compositions that include a combination of colorants. In certain non-limiting examples, the blue colorant as disclosed herein can be combined with one or more different yellow colorants to obtain a bright and true green colorant. A desirable bright and true green color is obtained by the combination of FD&C Yellow No. 5 and FD&C Blue No. 1. A mixture of FD&C Yellow No. 5 and FD&C Blue No. 1 at a 4:1 ratio (by weight) in solution, when applied in food products, gives a particularly desirable green color. Such an artificial green color applied to a hard panned confection showed an $L^*=60$, $a^*=-46$, $b^*=43$, $C^*=63$, and $h°=137$, and produces a desirable and true green color in a confectionery product. Heretofore, it has been difficult to achieve a color close or similar to the color achieved with the artificial colors noted.

The color of non-artificial colored products, for example hard panned candies, can be measured and compared to values of an ideal colored product from artificial colors. It is also possible to calculate the $\Delta E$ values for non-artificial colored candies relative to the artificial reference. For example, a product colored with red cabbage at pH 8 plus turmeric has a $\Delta E$ of 52 compared to the artificial reference, while the Spirulina plus turmeric panned candy has a $\Delta E$ of 31 compared to the artificial reference candy. A panned candy colored with Spirulina plus turmeric currently represents the state of the art for producing a green color using non-artificial colorants; these data show that non-artificial products are still notably different from their artificial counterparts.

In certain embodiments, Compound I at about pH 7 plus from about 0.3 to about 1.0 mol. equiv. (e.g., about ⅓ mol. equiv. or about 1 mol. equiv.) of $Al^{3+}$, $Fe^{2+}$, or $Fe^{3+}$ provides color characteristics as discussed below that mimic closely those characteristics of FD&C Blue No. 1 (cyan blue).

Such color characteristics combined with yellow colorants can lead to a bright and true green hue. Exemplary non-artificial yellow colorants useful for the edible colorant compositions described herein include, but are not limited to, curcuminoids (e.g., from turmeric), carotenoids (e.g., from saffron, gac fruit, and gardenia), annatto (e.g., from achiote) and combinations thereof. For instance, the non-artificial yellow colorant can be turmeric, safflower (Carthamus), beta carotene, or gardenia yellow. In certain embodiments, safflower is used as the non-artificial yellow colorant to produce a bright and true green hue.

Preferably, the non-artificial yellow colorant has a hue angle of about 90° or greater. At hue angles greater than about 90°, the yellow colorant includes comparatively less red and more green in the undertones, which results in a better green colorant composition when mixed with blue. At hue angles below about 90°, the yellow colorant includes comparatively more red, which results in a muddier green due to brown undertones in the green. Exemplary non-artificial yellow colorants that may be useful for the edible colorant compositions are provided below in Table 3. Values are taken from the non-artificial yellow colorants at different concentrations on finished panned candies.

TABLE 3

Non-artificial yellow colorants on panned candies

| Different colorant powders and use rates | Hue angle of finished panned candies |
| --- | --- |
| Beta-Carotene 1 (0.5%) | 75.51 |
| Beta-Carotene 2 (0.5%) | 84.10 |
| Beta-Carotene 3 (0.01%) | 95.03 |
| Beta-Carotene 3 (0.03%) | 90.84 |
| Beta-Carotene 4 (0.1%) | 87.70 |
| Beta-Carotene 4 (0.05%) | 91.41 |
| Safflower 1 (0.8%) | 90.39 |
| Safflower 2 (1%) | 104.68 |
| Safflower 3 (1%) | 93.71 |
| Safflower 4 (2%) | 100.33 |
| Safflower 5 (2%) | 90.24 |
| Safflower 6 (1%) | 85.66 |
| Safflower 7 (0.5%) | 95.64 |
| Safflower 7 (0.25%) | 101.06 |

TABLE 3-continued

Non-artificial yellow colorants on panned candies

| Different colorant powders and use rates | Hue angle of finished panned candies |
|---|---|
| Safflower 8 (1.5%) | 92.72 |
| Lutein 1 (0.5%) | 72.26 |
| Lutein 1 (0.1%) | 87.70 |
| Lutein 1 (0.05%) | 88.81 |
| Curcumin 1 No. 26295 (1%) | 80.58 |
| Curcumin 2 (0.2%) | 90.69 |
| Curcumin 2 (0.4%) | 87.09 |
| Curcumin 3 | 93.73 |
| Curcumin 4 (0.2%) | 83.41 |
| Curcumin 4 (0.25%) | 81.98 |
| FD&C-Yellow 5 (0.2%) synthetic | 81.29 |
| FD&C-Yellow 5 (0.1%) synthetic | 86.45 |
| FD&C-Yellow 5 (0.05%) synthetic | 91.53 |
| FD&C-Yellow 5 (0.0282%) synthetic | 93.19 |
| FD&C-Yellow 5 (0.02%) synthetic | 96.26 |
| Gardenia Yellow (0.4%) | 82.40 |

Further non-artificial yellow colorants known in the art aside from those listed in the above table may also be useful for the edible colorant compositions disclosed herein.

2.6 Color Characteristics

As embodied herein, color characteristics of the presently-disclosed non-artificial blue anthocyanin-containing colorants, can be determined. Such color characteristics can include hue, chroma, purity, saturation, intensity, vividness, value, lightness, brightness and darkness, and color model system parameters used to describe these properties, such as Commission Internationale de l'Eclairage CIE 1976 CIELAB color space L*a*b* values and CIELCH color space L*C*h° values.

For example, L*a*b* values consist of a set of coordinate values defined in a three-dimensional Cartesian coordinate system. L* is the value, or lightness, coordinate. L* provides a scale of lightness from black (0 L* units) to white (100 L* units) on a vertical axis, a* and b* are coordinates related to both hue and chroma, a* provides a scale for greenness (−a* units) to redness (+a* units), with neutral at the center point (0 a* units), on a horizontal axis; b* provides a scale for blueness (−b* units) to yellowness (+b* units), with neutral at the center point (0 b* units), on a second horizontal axis perpendicular to the first horizontal axis. The three axes cross where L* has a value of 50 and a* and b* are both zero.

L*C*h° values consist of a set of coordinate values defined in a three-dimensional cylindrical coordinate system. L* is the value, or lightness, coordinate. L* provides a scale of lightness from black (0 L* units) to white (100 L* units) on a longitudinal axis. h° is the hue coordinate. h° is specified as an angle from 0° to 3600 moving counterclockwise around the L* axis. Pure red has a hue angle of 0°, pure yellow has a hue angle of 90°, pure green has a hue angle of 180°, and pure blue has a hue angle of 270°. The C* coordinate represents chroma and is specified as a radial distance from the L* axis. C* provides a scale from achromatic, i.e., neutral white, gray, or black, at the L* axis (0 C* units) to greater purity of hue as the coordinate moves away from the L* axis (up to 100 or more C* units). C* and h° can be calculated from a* and b* using Equations 1 and 2:

$$C^* = (a^{*2} + b^{*2})^{0.5} \quad (1)$$

$$h° = \arctan(b^*/a^*) \quad (2)$$

"Delta E," "$\Delta E_{ab}^*$," or "$\Delta E$" is a measure of the magnitude of total color difference between two colors represented in CIELAB L*a*b* color space. It has been reported that an experienced color observer cannot distinguish any difference between two colors when the $\Delta E$ is about 2.3 or less. The $\Delta E$ of two different colors with L*a*b* values, $L^*_1 a^*_1 b^*_1$ and $L^*_2 a^*_2 b^*_2$, is calculated using Equation 3:

$$\Delta E_{ab}^* = \sqrt{(L_1^* - L_2^*)^2 + (a_1^* - a_2^*)^2 + (b_1^* - b_2^*)^2} \quad (3)$$

The CIELAB L*a*b* and CIELCH L*C*h° values of FD&C Blue No. 1 at seven different concentrations in aqueous solution are presented in Table 4.

TABLE 4

Aqueous solutions

| Concentration | L* | a* | b* | C* | h° |
|---|---|---|---|---|---|
| 1000 ppm | 10.49 | 15.82 | −44.99 | 47.69 | 289.37 |
| 500 ppm | 24.07 | 9.80 | −58.18 | 59.00 | 279.56 |
| 100 ppm | 52.43 | −29.57 | −57.38 | 64.55 | 242.74 |
| 50 ppm | 63.64 | −43.71 | −48.31 | 65.14 | 227.86 |
| 10 ppm | 84.25 | −37.23 | −23.42 | 43.99 | 212.17 |
| 5 ppm | 90.65 | −24.40 | −14.28 | 28.27 | 210.33 |
| 1 ppm | 97.69 | −6.43 | −3.57 | 7.36 | 209.02 |

The CIELAB L*a*b* and CIELCH L*C*h° values of FD&C Blue No. 1 at six different concentrations on panned candies are presented in Table 5.

TABLE 5

Panned candies

| Concentration | L* | a* | b* | C* | h° |
|---|---|---|---|---|---|
| 0.0075% (75 ppm) | 75.53 | −31.53 | −20.34 | 37.52 | 212.82 |
| 0.01% (100 ppm) | 74.64 | −29.29 | −16.23 | 33.49 | 208.99 |
| 0.02% (200 ppm) | 66.02 | −38.22 | −26.76 | 46.65 | 214.99 |
| 0.04% (400 ppm) | 58.64 | −38.68 | −31.67 | 50.00 | 219.31 |
| 0.05% (500 ppm) | 56.29 | −38.30 | −32.44 | 50.20 | 220.27 |
| 0.1% (1000 ppm) | 47.94 | −31.89 | −36.45 | 48.43 | 228.82 |

These L*a*b* and L*C*h° values for FD&C Blue No. 1 can be used as target values for a non-artificial blue anthocyanin-containing colorant alternative to FD&C Blue No. 1. Non-artificial blue colorants having L*a*b* values that fall within a $\Delta E$ of about 2.3 (defined as the just noticeable difference (JND)) or less from these target values would be expected to provide color characteristics sufficiently similar to those provided by FD&C Blue No. 1 that a human eye could not distinguish the difference in color provided by the non-artificial colorant versus the artificial. However, non-artificial blue anthocyanin-containing colorants having L*a*b* values that fall outside a $\Delta E$ of about 2.3 can also be used as a non-artificial substitute for FD&C Blue No. 1. The closer the L*a*b* values for a non-artificial blue colorant come to the artificial target values (i.e., yielding smaller values of $\Delta E$), the better replacement the non-artificial blue anthocyanin-containing colorant will be for FD&C Blue No. 1 in an edible application.

Mathematical models can be generated to represent the color characteristics provided by FD&C Blue No. 1 at any concentration in the L*a*b* and L*C*h° color spaces. For example, the color characteristics may be represented by a segmented line model connecting the L*a*b* or L*C*h° data points of Table 3 or 4. A line (L) connecting two points (P$_1$ and P$_2$) representing two different concentrations of FD&C Blue No. 1 in L*a*b* space can be calculated with the following Equation 4:

$$L=\{P_1+t*(P_2-P_1)\} \tag{4}$$

wherein, P$_1$ is (L*$_1$, a*$_1$, b*$_1$); P$_2$ is (L*$_2$, a*$_2$, b*$_2$); and t is any real number.

Consequently, a segmented line model for FD&C Blue No. 1 in L*a*b* color space can be interpolated based on the L*a*b* values for the seven different concentration points using Equation 4 as follows.

For concentrations between 500 and 1000 ppm, 0<t<1:
L*=10.49+13.58*t
a*=15.82+−6.02*t
b*=−44.99+−13.19*t For concentrations between 100 and 500 ppm, 0<t<1:
L*=24.07+28.36*t
a*=9.80+−39.37*t
b*=−58.18+0.80*t For concentrations between 50 and 100 ppm, 0<t<1:
L*=52.43+11.21*t
a*=−29.57+−14.14*t
b*=−57.38+9.07*t For concentrations between 10 and 50 ppm, 0<t<1:
L*=63.64+20.61*t
a*=−43.71+6.48*t
b*=−48.31+24.89*t For concentrations between 5 and 10 ppm, 0<t<1:
L*=84.25+6.40*t
a*=−37.23+12.83*t
b*=−23.42+9.14*t For concentrations between 1 and 5 ppm, 0<t<1:
L*=90.65+7.04*t
a*=−24.40+17.97*t
b*=−14.28+10.71*t In addition, colors having L*a*b* values falling within a specific ΔE range of the FD&C Blue No. 1 model can be mathematically modeled in L*a*b* color space. Selecting a specific ΔE value, e.g., 15, with respect to FD&C Blue No. 1 and plotting that ΔE in L*a*b* color space results in a tube-like structure around the FD&C Blue No. 1 segmented line model.

To determine whether a point (X$_0$) in L*a*b* color space falls within a specific ΔE value from the FD&C Blue No. 1 model, the minimum distance, d$_{min}$, between the point and the model (represented by line segment X$_1$ to X$_2$) must be calculated. Equation 5 can be used to calculate d$_{min}$:

$$d_{min} = \frac{|(x_0 - x_1) \times (x_0 - x_2)|}{|x_2 - x_1|} \tag{5}$$

wherein x denotes the cross product of two vectors and vertical bars denote the magnitude of a vector expression.

If the value of d$_{min}$ is less than or equal to the chosen ΔE value, then the point in L*a*b* color space falls within that specific ΔE value from the FD&C Blue No. 1 model.

The colorant compositions disclosed herein include non-artificial blue colorant compositions comprising a fraction of anthocyanins sourced from a non-artificial product, wherein the colorant composition can provide color characteristics having a ΔE value of about 10-12, or less, compared to the color characteristics defined by the segmented line defined by the L*a*b* values of 50 ppm and 100 ppm FD&C Blue No. 1 in aqueous solution. In other embodiments the ΔE value may be less than about 17, about 16, about 15, about 14, about 13, about 12, about 11, about 10, about 9, about 8, about 7, about 6, about 5, about 4, or about 3. The colorant composition may also be measured against a plurality of segmented lines defined by different concentrations of FD&C Blue No. 1 in aqueous solution, e.g., about 1 ppm and about 5 ppm, about 5 ppm and about 10 ppm, about 10 ppm and about 50 ppm, about 100 ppm and about 500 ppm, about 500 ppm and about 1000 ppm, or any combination selected therefrom. However, if ΔE value is used to describe the colorant composition, only one segmented line is required to define the colorant composition.

2.6.1 Visible Lambda Max of Compound I

One of the ways in which a colorant is defined is via absorbance in the visible region of the absorption spectrum and the lambda max ($\lambda_{max}$), which is the wavelength corresponding to the maximal absorbance value of the visible spectra for a solution. Using a $\lambda_{max}$ value and comparison of absorbance over wavelength curves, it is possible to measure, for example, violet contributions.

Other methods can be used to capture color through measurement of solutions in a colorimeter. For example, a Konica Minolta—CM-5 Spectrophotometer can be used in conjunction with appropriate software, for example, color data software CM-S100W and/or SpectraMagic NX. L*a*b*, C, and H (hue angle) values can be obtained for each measurement, and color comparisons can be plotted on an a*b* space (cross section of a spherical color space) at a set value for L*.

In certain embodiments, a solution of the colorant (e.g., Compound I and a metal ion in a solution having a pH of from about 6.0 to about 8.0) will have a measured absorbance of between about 0.5 and about 1.0 in a cuvette having a path length of, e.g., 1 cm, or from about 0.2 mm to about 10 mm, e.g., about 0.2 mm, about 0.3 mm, about 0.5 mm, about 0.7 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, or about 10 mm, and will have an absorbance maxima (lambda max) of between about 630 nm and about 655 nm, between about 630 and about 650 nm between about 630 nm and about 647 nm, between about 635 and about 647 nm, between about 640 nm and about 647 nm, between about 635 nm and about 655 nm, between about 640 nm and about 655 nm, between about 645 and about 655 nm, between about 650 nm and about 655 nm, or between about 643 nm and about 647 nm. For example, the lambda max value can be determined from a dilute solution of the colorant, which will have an absorbance between about 0.5 and about 1.0 in a cuvette having a path length of about 0.5 cm or about 1 cm. For more concentrated solutions of the colorant, the lambda max value will need to be taken in a cuvette having a shorter path length. The path length of the cuvette is chosen by aiming for an absorbance between about 0.5 to about 1.0 so that the lambda max value can be determined.

2.6.2 Calculating the Violet Component of a Blue Colorant

Violet components of a blue colorant can be determined according to the following method. The violet region of the visible light spectrum is defined as the absorbance over the range from about 500 nm to about 600 nm. A sample solution is prepared such that the maximum absorbance in a 1 cm cuvette is about 0.75. For the methods described herein, the cuvette can have a path length of from about 0.2 mm to about 10 mm, e.g., about 0.2 mm, about 0.3 mm, about 0.5 mm, about 0.7 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, or about 10 mm, depending on the concentration of the solution. The area under the curve of absorbance over wavelength is then calculated for violet contribution. In order to compare data between different spectra, the different spectral data is normalized to allow for direct comparison.

2.6.3 Colorimetric Data for Compound I

Colorimetric data for solutions of FD&C Blue No. 1, Compound I with no metal, Compound I with 1.0 mol. eq. of $Al^{3+}$ at pH 7, and Compound I with 1.0 mol. eq. of $Al^{3+}$ at pH 8 are provided below in Table 6, showing $\lambda_{max}$ values; Table 7, showing L*a*b* values; and Table 8, showing violet contribution values.

TABLE 6

$\lambda_{max}$ values

| Material | $\lambda_{max}$ |
|---|---|
| FD&C Blue No. 1 | 630 |
| Compound I with no metal at pH 8 | 607 |
| Compound I + 1.0 mol. eq. $Al^{3+}$ at pH 7 | 636 |
| Compound I + 1.0 mol. eq. $Al^{3+}$ at pH 8 | 637 |

TABLE 7

L*a*b* and ΔE values

| Material | L* | a* | b* | ΔE (relative to control) |
|---|---|---|---|---|
| FD&C Blue No. 1 solution (control) | 90 | −28 | −15 | — |
| Spirulina solution | 80 | −27 | −29 | 17.15 |
| Compound I + 1.0 mol. eq. $Al^{3+}$ at pH 7 | 83 | −32 | −16 | 8.27 |
| Compound I + no metal at pH 8 | 75 | −20 | −30 | 22.06 |
| Compound I + 1.0 mol. eq. $Al^{3+}$ at pH 8 | 82 | −31 | −18 | 9.18 |

TABLE 8

Violet contribution

| Material | Violet Contribution |
|---|---|
| FD&C Blue No. 1 | 10.7 |
| Compound I with no metal at pH 8 | 37.5 |
| Compound I + 1.0 mol. eq. $Al^{3+}$ at pH 7 | 20.5 |
| Compound I + 1.0 mol. eq. $Al^{3+}$ at pH 8 | 22.2 |

The L* value for Compound I plus a metal ion (e.g., $Al^{3+}$, $Fe^{2+}$, or $Fe^{3+}$) at about pH 6 to about pH 8 can range from about 70 to about 90, or from about 72 to about 86, or from about 72 to about 80, or from about 73 to about 75. In a specific embodiment, the L* value is about 73.

In certain embodiments, Compound I plus a metal ion (e.g., $Al^{3+}$, $Fe^{2+}$, or $Fe^{3+}$) has a* and b* values (from L*a*b* color space) such that a* ranges from about −20 to about −47, and b* ranges from about −15 to about −30, or more preferably where a* ranges from about −25 to about −35 and b* ranges from about −15 to about −25 or most preferably where a* ranges from about −28 to about −32 and b* ranges from about −15 to about −20.

A computed ΔE value for a solution of Compound I with about 0.3 or about 1.0 mol. equiv. $Al^{3+}$ at about pH 8 or about pH 7 as compared to FD&C Blue No. 1 is less than about 17, wherein FD&C Blue No. 1 has an L* value of about 90. In certain embodiments, the computed ΔE value as compared to FD&C Blue No. 1 is less than about 17, wherein L* is about 83. In certain embodiments, the ΔE is less than about 16, or less than about 15, or less than about 14, or less than about 13, or less than about 12, or less than about 11, or less than about 10, or less than about 9, or less than about 8, or less than about 7, or less than about 6, or less than about 5, or less than about 4, or less than about 3. In certain embodiments, the ΔE can range from about 8 to about 10.

In certain embodiments, the hue angle (from L*C*h° color space) for Compound I at about pH 7 plus a metal ion can range from about 207° to about 230°, or from about 207° to about 225°, or from about 207° to about 220°, or from about 207° to about 215°, or from about 207° to about 211°, or from about 208° to about 210°.

In certain embodiments, the colorant solution has a reduced absorbance and violet contribution in the range of about 500 nm to about 600 nm. In certain embodiments, the absorbance (area under curve) in the range of about 500 nm to about 600 nm is less that about 29, less than about 28, less than about 26, less than about 24, less than about 22 or less than about 21, or less than about 20.

The violet region of visible light spectrum defined as the range from about 500 nm to about 600 nm. The violet color contribution to a blue color is measured by integrating the area under the visible absorbance curve over the wavelength range from about 500 to about 600 nm. The value calculated represents the area under the curve (area units*wavelength) and is a measure of the violet hue present in the blue color. This violet color contribution can be compared for one colorant versus another and in this case will be compared to the violet color for the spectra of a reference solution of FD&C Blue No. 1.

3. Enzymatic Treatment and Isolation of Anthocyanins

While Compound I with a metal ion (e.g., $Al^{3+}$, $Fe^{2+}$, or $Fe^{3+}$) provides unexpected and desired colorant properties, it has faced difficulties in commercial applications due to the lack of cost-efficient methods of producing Compound I. Compound I is only a minor component of the anthocyanin content in red cabbage juice or extract, as naturally occurring red cabbage juice or extract comprises only from about 1% to about 4% of Compound I. As such, even if Compound I were to be separated from other anthocyanins by fractionation methods or otherwise, large quantities of red cabbage juice would still be necessary to produce Compound I in the quantities required for commercial use. The purification procedures necessary to separate Compound I from the seven other anthocyanin compounds occurring in red cabbage juice also largely increase the costs of the process. Furthermore, there are no known synthetic procedures that would make the compound in commercial quantities. Therefore, new methods for obtaining Compound I are necessary, especially those that would be commercially viable.

As stated previously, structural review of the anthocyanins occurring in red cabbage juice revealed that Compound I is structurally similar to Compounds D-F, with an exception that Compounds D-F have an acyl group (e.g., a para coumaric group, a ferulic group, or a sinapic group) instead of H at the $R_2$ position of the general anthocyanin compound represented by Formula 1. Hydrolysis of the $R_2$ ester linkage would result in Compound I. However, a highly selective catalyst is needed for this chemical transformation, as Compound I itself includes an ester group, i.e., a sinapic group at the R₁ position. Specifically, only the acyl group from the 3-glucoside-2"-OH position of anthocyanins (i.e., the R₂ position) should be removed. If both acyl groups (i.e., R₁ and R₂) of Compounds D-F are removed, Compound II, not Compound I, is produced.

The present disclosure utilizes the high specificity of enzymatic catalysis to perform the selective conversion as shown below:

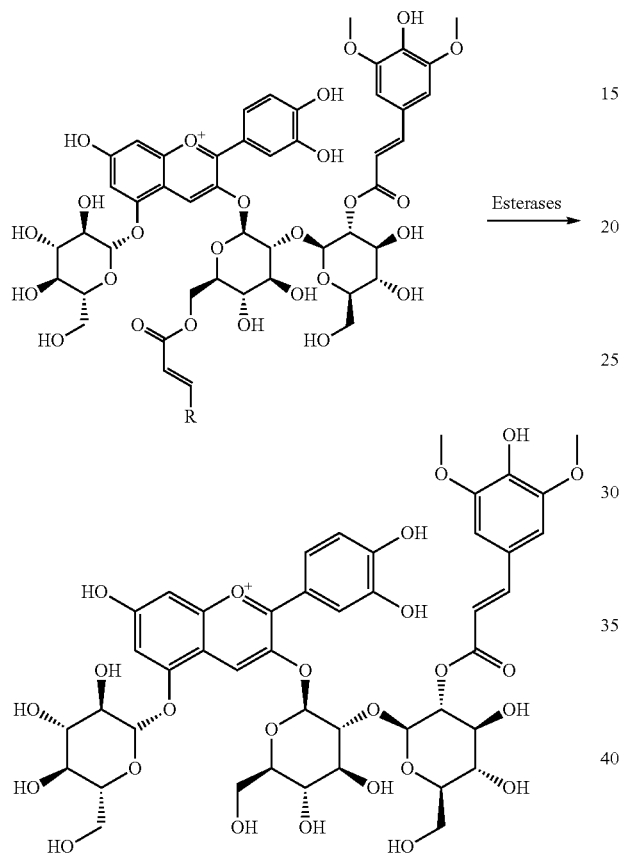

Advantageously, an esterase can be used to enzymatically treat a solution including a mixture of anthocyanins to reduce the total number of anthocyanins in the mixture, i.e., such that only Compound I, or only Compounds I and II, are the remaining anthocyanins of a total anthocyanin content in the solution. This allows for simplified isolation of the desired anthocyanin, e.g., Compound I, from the solution mixture.

3.1 Esterases

An esterase refers to a class of enzymes that catalyze the hydrolysis of an ester bond. In certain embodiments, an esterase of the present disclosure catalyzes the hydrolysis of an ester from the 3-glucose of a mono- and/or a di-acylated triglucoside anthocyanin, yielding an anthocyanin with a 3 (2"-carboxyl)-diglucoside-5-glucoside structure. In certain embodiments, an esterase of the present disclosure selectively catalyzes the hydrolysis of an ester from the 3-glucose of a mono- and/or a di-acylated triglucoside anthocyanin without catalyzing the hydrolysis of another ester bond present in the anthocyanin molecule. In certain embodiments, an esterase capable of catalyzing such a reaction is a naturally occurring esterase. In certain other embodiments, an esterase capable of catalyzing such a reaction is a modified esterase. A modified esterase may include at least one amino acid substitution relative to its naturally occurring counterpart.

3.1.1 Naturally Occurring Esterases

In certain embodiments, an esterase of the present disclosure comprises an amino acid sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15. An esterase of the present disclosure (e.g., an esterase of any one of SEQ ID NO: 1-15) can optionally be tagged at the C-terminus with a hexahistidine tag having the amino acid sequence of GGSLEHHHHHH (SEQ ID NO: 90).

In certain embodiments, the esterase of the present disclosure is carboxylesterase from *Chromohalobacter salexigens*, which has the amino acid sequence set forth in SEQ ID NO: 1, provided below.

[SEQ ID NO: 1]
MADSSPLIIEPRQARAADATVILLHGLGADGHDFE

PLVPALPLAKDLAVRFVLPHAPRMPVTVNGGMEMP

AWYDILDMNLGRRIDEAQLKASADMVHGLIDAEIA

RGIDSRRIIVAGFSQGGAVAYHAALTYPKPLGGLL

ALSTYFATATSIEPSEANRALPIEVHHGSFDPVVP

EALGHEGAERAEALGYAVTYRTYPMQHALCPEQIE

DIGQWLNARLGAKEA.

In certain embodiments, the esterase of the present disclosure is carboxylesterase from *Pseudomonas fluorescens*, which has the amino acid sequence set forth in SEQ ID NO: 2, provided below.

[SEQ ID NO: 2]
MTEPLILQPAKPADACVIWLHGLGADRYDEMPVAE

ALQESLLTTREVLPQAPTRPVTINGGYEMPSWYDI

KAMSPARSISLEELEVSAKMVTDLIEAQKRTGIDA

SRIFLAGESQGGAVVEHTAFINWQGPLGGVIALST

YAPTEGDELELSASQQRIPALCLHGQYDDVVQNAM

GRSAFEHLKSRGVTVTWQEYPMGHEVLPQEIHDIG

AWLAARLG.

In certain embodiments, the esterase of the present disclosure is carboxylesterase from *Pseudomonas aeruginosa*, which has the amino acid sequence set forth in SEQ ID NO: 3, provided below.

[SEQ ID NO: 3]
MSEPLILDAPNADACIIWLHGLGADRTDFKPVAEA

LQMVLPSTRFILPQAPSQAVTVNGGWVMPSWYDIL

AFSPARAIDEDQLNASADQVIALIDEQRAKGIAAE

RIILAGFSQGGAVVLHTAFRRYAQPLGGVLALSTY

APTEDDLALDERHKRIPVLHLHGSQDDVVDPALGR

-continued

AAHDALQAQGVEVGWHDYPMGHEVSLEEIHDIGAW

LRKRLGGS.

In certain embodiments, the esterase of the present disclosure is arylesterase from *Sulfolobus solfataricus*, which has the amino acid sequence set forth in SEQ ID NO: 4, provided below.

[SEQ ID NO: 4]
MPLDPEVRNFLQVYYKANIIDFTKYQFQEIRQKVN

ELLAKAVPKDPVGETRDMKIKLEDYELPIRIYSPI

KRTNNGLVMHFHGGAWILGSIETEDAISRILSNSC

ECTVISVDYRLAPEYKFPTAVYDCFNAIVWARDNA

GELGIDKDKIATFGISAGGNLVAATSLLARDNKLK

LTAQVPVVPFVYLDLASKSMNRYRKGYFLDINLPV

DYGVKNYIRDEKDLYNPLFSPLIAEDLSNLPQAIV

VTAEYDPLRDQGEAYAYRLMESGVPTLSFRVNGNV

HAFLGSPRTSRQVTVMIGALLKDIFKGSS.

In certain embodiments, the esterase of the present disclosure is ferulic acid esterase from *Aspergillus niger*, which has the amino acid sequence set forth in SEQ ID NO: 5, provided below.

[SEQ ID NO: 5]
MKQFSAKYALILLATAGQALAASTQGISEDLYNRL

VEMATISQAAYADLCNIPSTIIKGEKIYNAQTDIN

GWILRDDTSKEIITVERGTGSDTNLQLDTNYTLTP

FDTLPQCNDCEVHGGYYIGWISVQDQVESLVKQQA

SQYPDYALTVTGHSLGASMAALTAAQLSATYDNVR

LYTEGEPRSGNQAFASYMNDAFQVSSPETTQYFRV

THSNDGIPNLPPADEGYAHGGVEYWSVDPYSAQNT

EVCTGDEVQCCEAQGGQGVNDAHTTYFGMTSGACT

W.

In certain embodiments, the esterase of the present disclosure is carboxylesterase from *Francisella tularensis*, which has the amino acid sequence set forth in SEQ ID NO: 6, provided below.

[SEQ ID NO: 6]
MNYELMEPAKQARFCVIWLHGLGADGHDFVDIVNY

FDVSLDEIRFIFPHADIIPVTINMGMQMRAWYDIK

SLDANSLNRVVDVEGINSSIAKVNKLIDSQVNQGI

ASENIILAGFSQGGIIATYTAITSQRKLGGIMALS

TYLPAWDNFKGKITSINKGLPILVCHGTDDQVLPE

VLGHDLSDKLKVSGFANEYKHYVGMQHSVCMEEIK

DISNFIAKTFKI.

In certain embodiments, the esterase of the present disclosure is alkaline esterase from uncultured bacterium FLS12, which has the amino acid sequence set forth in SEQ ID NO: 7, provided below.

[SEQ ID NO: 7]

MALFQCDFFSDVLGLSTSMTVILPQETTGQIGMAG

GSERREHPTLFLLHGLSDDHTIWLRRTSIERYVAE

MGLAVVMPAVHRSFYTDMAHGLQYWTFISEELPAL

ARSFFPLATAREDTFVAGLSMGGYGALKLGMRHPE

RFAAAASLSGALDITFDPAEHIAMEDDVWVAEQRN

IFGDLAALPGSDHDLFALAERMAQSDGPVPKLYQC

CGTEDFLYEDNVRERDHVRGLGLDEMYEESPGEHE

WGYWDAQIQRVLAWLPLRPPGTAPA.

In certain embodiments, the esterase of the present disclosure is esterase from *Pelagibacterium halotolerans*, which has the amino acid sequence set forth in SEQ ID NO: 8, provided below.

[SEQ ID NO: 8]

MTEPVKLSGPMLPAVSGAAKSLVVLLHGYGSDGRD

LIALGQFWRDSFPDTMFVAPNAPHVCGGNPFGYEW

FPLDLERDRTLARLAGAETAHPVLDAFLADLWAQT

GLGPADTILVGFSQGAMMALYTGLRLPEPLKAIIA

FSGLIVAPEKLEAEIASKPPVLLIHGDLDDVVPVI

GSETALPKLIDLGIDARLHISQGSGHTIAQDGLDT

ATAFLREIL.

In certain embodiments, the esterase of the present disclosure is lipase carboxylesterase from *Sulfolobus islandicus*, which has the amino acid sequence set forth in SEQ ID NO: 9, provided below.

[SEQ ID NO: 9]

MMPLDPRIKELLESGFIVPIGKASVDEVRKIFRQL

ASAAPKVEVGKVEDIKIPGSEANINARVYLPKANG

PYGVLIYLHGGGFVIGDVESYDPLCRAITNACNCV

VVSVDYRLAPEYKFPSAVIDSFDATNWVYNNLDKF

DGKMGVAIAGDSAGGNLAAVVALLSKGKLNLKYQI

LIYPAVGFDSVSRSMIEYSDGFFLTREHIEWFGSQ

YLRSPADLLDFRFSPILAQDLSGLPPALIITAEYD

PLRDQGEAYANRLLQAGVPVTSVRFNNVIHGFLSF

FPLIEQGRDAISLIGSVLRRTFYDKS.

In certain embodiments, the esterase of the present disclosure is carboxylesterase from *Halomonas* sp. QHL1, which has the amino acid sequence set forth in SEQ ID NO: 10, provided below.

[SEQ ID NO: 10]
MTAPGELIIEPKDGQPADACVFIIHGLGADGHDFE

PLVPALALPKDSRVRFIMPHAPRLPVTINGGMVMP

AWYDILAMDLGRRVDERQLKQSAERIQALIQEQID

QGIDSQRIIVAGFSQGGAVAYHAALTFPAPLGGLL

AMSTYFATADNIDLAEANRQIPIEVQHGNFDPIVP

ESLGRSGADRLKEMGYAVNYRQYPMAHALCPQQVN

DIGKWLSARLN.

In certain embodiments, the esterase of the present disclosure is carboxylesterase from *Ignatzschineria indica*, which has the amino acid sequence set forth in SEQ ID NO: 11, provided below.

[SEQ ID NO: 11]
MDKPIILDPKQSADSAVIWLHGLGATKEDFLPVAQ

ILQRDALPHTRFILPQAPVRPVTLNNGFPMPSWYD

IIALTSPREIKLSELDESSQSIIALIEAEIEKGIP

LERIILAGFSQGGAVVLHTAFIAYPKNVGGVMALS

TYSATFDEAITLDEKKKQIPTLHLHGSLDPVVKIE

LGRAAEQFLKAQGIDTRWHDYPMQHEVINDELQDI

AKWLIERLG.

In certain embodiments, the esterase of the present disclosure is carboxylesterase from *Pseudomonas citronellolis*, which has the amino acid sequence set forth in SEQ ID NO: 12, provided below.

[SEQ ID NO: 12]
MSQPLLLEPTQPADSCVIWLHGLGADRYDFEPVAR

MLQKVLPRTRFILPQAPTRPVTVFNGMPAPSWYDI

KAMAPARAIDEAQLDASADAVIALIEGQLAEGIAQ

RRIVLAGFSQGGAVVLHTGYLRWPGELGGVMALST

YGPTFDDDLQLPEAKKQQPALCLHGTYDDVVAPAM

GRAAYDFLQRQGVAVQWRDYPMAHEVSNQEIADIA

AWLRERL.

In certain embodiments, the esterase of the present disclosure is beta-lactamase from *Myxococcus fulvus*, which has the amino acid sequence set forth in SEQ ID NO: 13, provided below.

[SEQ ID NO: 13]
MNGLRWRLTGVVMAWVLVAPLAEAANVKQEVDRYI

SGFHQKGLFNGTVLVANERGILLKKGYGAANLEWK

VPNAPDTKFRIGSITKSFTATVILQLAAEGKLQLD

DPITKHLPDYRKDTGDRVTITHLLNHTSGIPSYTS

KPAIMKDADGFESVAAFVKKACSDDLEFEPGTKYA

YNNSGYFLLGAIIEKLTGQTYAEAVQARILGPLGM

KDTGYDVSATVLPKRASGYAQAPGGIVNAAWLDMN

LPYAAGSLYSTVEDLYRWERAFHGDTLLPAALKQK

MLTPGLAHYGFGWVMSDMTLHDGKTKLPGIFHTGG

INGFSSILVRVPERKEAVILLDNMTHGGLQELAGG

VLSILHGLTPRPARMPIGNVMMESLGKGSVAQATA

TYRTLKKTKQAEYDFSERHLNTVGYHLLRSGRAAD

AIEVFKLNVEMEPEAANCHDSLGEAYAAHGDKARA

ITSYRKALELAPKNEHAVKMLEQLEEPAAKR.

In certain embodiments, the esterase of the present disclosure is carboxylesterase from *Pseudomonas saudiphocaensis*, which has the amino acid sequence set forth in SEQ ID NO: 14, provided below.

[SEQ ID NO: 14]
MTDPLIIEPAQTADSCVIWLHGLGADRYDEQPVAE

MLQQRLLHTREVLPQAPTRAVTINGGWAMPSWYDI

QAMSPARAIDQAQLEQSAQTVIELIEQQRDSGIDP

RRIFLAGESQGGAVVYHTAFLRWAGPLGGVLALST

YAPTEGDDLKLSPLQAGLPVLCLHGSRDDVVPPAM

GRAAHDCLQQNQVQTQWKEYPMAHEVQPTEIQDIG

DWLASRLG.

In certain embodiments, the esterase of the present disclosure is carboxylesterase from *Ventosimonas gracilis*, which has the amino acid sequence set forth in SEQ ID NO: 15, provided below.

[SEQ ID NO: 15]
MTEPLIIEPSQPADSAVIWLHGLGADRFDFEPVARLLGQHLPSTRFILPQ

APTRPVTFNMGHAMPSWYDILALDGSERAINPADLEASSETLIALINAQQ

QSGIDSKRIVLAGFSQGGAVVLHTALLRFDEKLAGVLALSTYAPTFNAET

QFAESKQNLPVLCMHGSEDAVLPISMGRAVYDKLSEQGIKANWRDYPMGH

EVRPEQLRDILDWLKNTLPSLP.

3.1.2 Modified Esterases

The disclosure also features modified esterases useful for catalyzing the hydrolysis of an ester bond in an anthocyanin. A modified esterase can include modifications that either maintain the activity of the naturally occurring enzyme or enhances it, e.g., by increasing the rate of conversion or by increasing the percent completion of the reaction. Modifications can be made at the active site of the native sequence, or at any other location within the native sequence of the naturally occurring enzyme. In certain embodiments, a modified esterase of the present disclosure includes those containing an active site motif(s) having at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity, or having at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acid substitutions relative to the reference sequence, i.e., the naturally occurring counterpart to the modified esterase.

For example, the active site of a naturally occurring enzyme can be the active site of a carboxylesterase from *Pseudomonas fluorescens* having the amino acid sequence of SEQ ID NO: 2. The active site of the carboxylesterase from *P. fluorescens* having the amino acid sequence of SEQ ID NO: 2 is comprised of catalytically relevant amino acids at position numbers 25, 28, 29, 30, 31, 38, 39, 63, 65, 70, 73, 200, and 201. In certain embodiments, a modified esterase of the present disclosure is based on a scaffold of a carboxylesterase from *P. fluorescens* and includes an amino acid substitution at one or more amino acid position numbers of 25, 28, 29, 30, 31, 38, 39, 63, 65, 70, 73, 200, and 201 of the carboxylesterase from *P. fluorescens*. An amino acid substitution in a modified esterase relative to its naturally occurring counterpart can be a conservative or a nonconservative amino acid substitution as is known and understood in the art. For example, in certain embodiments, a modified esterase of the present disclosure is based on the carboxylesterase from *P. fluorescens* of SEQ ID NO: 2, and includes an amino acid substitution at amino acid position number 73 of SEQ ID NO: 2. The amino acid substitution at amino acid position number 73 can be, for instance, a methionine to histidine amino acid substitution. In one particular example, a modified esterase of the present disclosure comprises the amino acid sequence of SEQ ID NO: 16.

In another example, a modified esterase of the present disclosure is based on a scaffold of a carboxylesterase from *Chromohalobacter salexigens* having the amino acid sequence of SEQ ID NO: 1. The active site of the carboxylesterase from *C. salexigens* having the amino acid sequence of SEQ ID NO: 1 can be comprised of catalytically relevant amino acids at position numbers 23, 28, 75, 115, 117, 119, 121, 122, 125, 129, 168, 171, 173, 202, 209, and/or 212. In certain embodiments, a modified esterase of the present disclosure is based on a scaffold of a carboxylesterase from *C. salexigens* and includes an amino acid substitution at one or more amino acid position numbers of 23, 28, 75, 115, 117, 119, 121, 122, 125, 129, 168, 171, 173, 202, 209, or 212. An amino acid substitution in a modified esterase relative to its naturally occurring counterpart can be a conservative or a nonconservative amino acid substitution as is known and understood in the art. In other nonlimiting embodiments, the active site of a carboxylesterase of *C. salexigens* having the amino acid sequence of SEQ ID NO: 1 can be modified to include a I, V, or L at amino acid position 23; A, S, or T at amino acid position 28; I, V, or L at amino acid position 75; I, V, or L at amino acid position 115; A, G, P, or S (tiny residue) at amino acid position 116; G at amino acid position 117; S at amino acid position 119; G at amino acid position 121; G at amino acid position 122; V or A at amino acid position 125; A, G, or S at amino acid position 129; A, G, or S at amino acid position 168; D at amino acid position 171; I, V, or L at amino acid position 173; H at amino acid position 203; I, V, or L at amino acid position 209; and/or I, V, or L at amino acid position 212.

In some embodiments, the modified esterase of the present disclosure comprises an amino acid sequence having at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acid substitutions relative to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15. For instance, a modified esterase can include an amino acid substitution at, for example, an amino acid at position 25, 28, 29, 30, 31, 38, 39, 63, 65, 70, 73, 200, and/or 201 of SEQ ID NO: 2. In another example, a modified esterase can include an amino acid substitution at, for example, an amino acid at position 23, 28, 75, 115, 117, 119, 121, 122, 125, 129, 168, 171, 173, 202, 209, and/or 212 of SEQ ID NO: 1. Such an amino acid substitution can be a conservative or a nonconservative amino acid substitution as known in the art. In certain non-limiting embodiments, the modified esterase maintains the original active site motif of its naturally occurring counterpart. In other embodiments, the modified esterase maintains an active site having at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% sequence identity relative to the original active site motif of its naturally occurring counterpart, e.g., wherein the naturally occurring counterpart is an enzyme having the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15.

For example, in certain embodiments, the esterase of the present disclosure is a modified esterase comprising an amino acid sequence set forth in SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, or SEQ ID NO: 43. A modified esterase of the present disclosure (e.g., a modified esterase of any one of SEQ ID NO: 16-43) can optionally be tagged at the C-terminus with a hexahistidine tag having the sequence of SEQ ID NO: 90.

In certain embodiments, the esterase of the present disclosure is carboxylesterase from *Pseudomonas fluorescens* modified by an amino acid substitution at position 73, which has the amino acid sequence set forth in SEQ ID NO: 16, provided below.

[SEQ ID NO: 16]
MTEPLILQPAKPADACVIWLHGLGADRYDFMPVAEALQESLLTTRFVLPQ

APTRPVTINGGYEMPSWYDIKAHSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHE

VLPQEIHDIGAWLAARLG.

In certain embodiments, the esterase of the present disclosure is carboxylesterase from *Pseudomonas fluorescens* modified by an amino acid substitution at position 29, which has the amino acid sequence set forth in SEQ ID NO: 17, provided below.

[SEQ ID NO: 17]
MTEPLILQPAKPADACVIWLHGLGADRYGFMPVAEALQESLLTTRFVLPQ

APTRPVTINGGYEMPSWYDIKAMSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHE

VLPQEIHDIGAWLAARLG.

In certain embodiments, the esterase of the present disclosure is carboxylesterase from *Pseudomonas fluorescens* modified by an amino acid substitution at position 73, which has the amino acid sequence set forth in SEQ ID NO: 18, provided below.

[SEQ ID NO: 18]
MTEPLILQPAKPADACVIWLHGLGADRYDFMPVAEALQESLLTTRFVLPQ

APTRPVTINGGYEMPSWYDIKAVSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHE

VLPQEIHDIGAWLAARLG.

In certain embodiments, the esterase of the present disclosure is carboxylesterase from *Pseudomonas fluorescens* modified by an amino acid substitution at position 200, which has the amino acid sequence set forth in SEQ ID NO: 19, provided below.

[SEQ ID NO: 19]
MTEPLILQPAKPADACVIWLHGLGADRYDFMPVAEALQESLLTTRFVLPQ

APTRPVTINGGYEMPSWYDIKAMSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHS

VLPQEIHDIGAWLAARLG.

In certain embodiments, the esterase of the present disclosure is carboxylesterase from *Pseudomonas fluorescens* modified by an amino acid substitution at position 200, which has the amino acid sequence set forth in SEQ ID NO: 20, provided below.

[SEQ ID NO: 20]
MTEPLILQPAKPADACVIWLHGLGADRYDFMPVAEALQESLLTTRFVLPQ

APTRPVTINGGYEMPSWYDIKAMSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHT

VLPQEIHDIGAWLAARLG.

In certain embodiments, the esterase of the present disclosure is carboxylesterase from *Pseudomonas fluorescens* modified by an amino acid substitution at positions 65 and 73, which has the amino acid sequence set forth in SEQ ID NO: 21, provided below.

[SEQ ID NO: 21]
MTEPLILQPAKPADACVIWLHGLGADRYDFMPVAEALQESLLTTRFVLPQ

APTRPVTINGGYEMSSWYDIKAHSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHE

VLPQEIHDIGAWLAARLG.

In certain embodiments, the esterase of the present disclosure is carboxylesterase from *Pseudomonas fluorescens* modified by an amino acid substitution at position 63, which has the amino acid sequence set forth in SEQ ID NO: 22, provided below.

[SEQ ID NO: 22]
MTEPLILQPAKPADACVIWLHGLGADRYDFMPVAEALQESLLTTRFVLPQ

APTRPVTINGGYDMPSWYDIKAMSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHE

VLPQEIHDIGAWLAARLG.

In certain embodiments, the esterase of the present disclosure is carboxylesterase from *Pseudomonas fluorescens* modified by an amino acid substitution at positions 25, 70, and 73, which has the amino acid sequence set forth in SEQ ID NO: 23, provided below.

[SEQ ID NO: 23]
MTEPLILQPAKPADACVIWLHGLGGDRYDFMPVAEALQESLLTTRFVLPQ

APTRPVTINGGYEMPSWYDLKAVSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHE

VLPQEIHDIGAWLAARLG.

In certain embodiments, the esterase of the present disclosure is carboxylesterase from *Pseudomonas fluorescens* modified by an amino acid substitution at positions 70, 73, and 200, which has the amino acid sequence set forth in SEQ ID NO: 24, provided below.

[SEQ ID NO: 24]
MTEPLILQPAKPADACVIWLHGLGADRYDFMPVAEALQESLLTTRFVLPQ

APTRPVTINGGYEMPSWYDLKAVSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHS

VLPQEIHDIGAWLAARLG.

In certain embodiments, the esterase of the present disclosure is carboxylesterase from *Pseudomonas fluorescens* modified by an amino acid substitution at positions 200, and 201, which has the amino acid sequence set forth in SEQ ID NO: 25, provided below.

[SEQ ID NO: 25]
MTEPLILQPAKPADACVIWLHGLGADRYDFMPVAEALQESLLTTRFVLPQ

APTRPVTINGGYEMPSWYDIKAMSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHT

ILPQEIHDIGAWLAARLG.

In certain embodiments, the esterase of the present disclosure is carboxylesterase from *Pseudomonas fluorescens* modified by an amino acid substitution at positions 73, and 200, which has the amino acid sequence set forth in SEQ ID NO: 26, provided below.

[SEQ ID NO: 26]
MTEPLILQPAKPADACVIWLHGLGADRYDFMPVAEALQESLLTTRFVLPQ

APTRPVTINGGYEMPSWYDIKAVSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHS

VLPQEIHDIGAWLAARLG.

In certain embodiments, the esterase of the present disclosure is carboxylesterase from *Pseudomonas fluorescens* modified by an amino acid substitution at positions 25, 28, 70, and 73, which has the amino acid sequence set forth in SEQ ID NO: 27, provided below.

[SEQ ID NO: 27]
MTEPLILQPAKPADACVIWLHGLGAGRTDFMPVAEALQESLLTTRFVLPQ

APTRPVTINGGYEMPSWYDLKAVSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHE

VLPQEIHDIGAWLAARLG.

In certain embodiments, the esterase of the present disclosure is carboxylesterase from *Pseudomonas fluorescens* modified by an amino acid substitution at positions 25, 28, 29, 30, and 31, which has the amino acid sequence set forth in SEQ ID NO: 28, provided below.

[SEQ ID NO: 28]
MTEPLILQPAKPADACVIWLHGLGAGRTSHRPVAEALQESLLTTRFVLPQ

APTRPVTINGGYEMPSWYDIKAMSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHE

VLPQEIHDIGAWLAARLG.

In certain embodiments, the esterase of the present disclosure is carboxylesterase from *Pseudomonas fluorescens* modified by an amino acid substitution at position 31, which has the amino acid sequence set forth in SEQ ID NO: 29, provided below.

[SEQ ID NO: 29]
MTEPLILQPAKPADACVIWLHGLGADRYDFKPVAEALQESLLTTRFVLPQ

APTRPVTINGGYEMPSWYDIKAMSPARSISLEELEVSAKMVTDLIEAQKR

TGIDASRIFLAGFSQGGAVVFHTAFINWQGPLGGVIALSTYAPTFGDELE

LSASQQRIPALCLHGQYDDVVQNAMGRSAFEHLKSRGVTVTWQEYPMGHE

VLPQEIHDIGAWLAARLG.

In certain embodiments, the esterase of the present disclosure is carboxylesterase from *Pseudomonas fluorescens* modified by an amino acid substitution at position 31, which has the amino acid sequence set forth in SEQ ID NO: 30, provided below.

[SEQ ID NO: 30]
MTEPLILQPAKPADACVIWLHGLGADRYDERPVAEALQESLLTTRFVLP

QAPTRPVTINGGYEMPSWYDIKAMSPARSISLEELEVSAKMVTDLIEAQ

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at position 70, which has the amino acid sequence set forth in SEQ ID NO: 31, provided below.

[SEQ ID NO: 31]
MTEPLILQPAKPADACVIWLHGLGADRYDEMPVAEALQESLLTTRFVLP

QAPTRPVTINGGYEMPSWYDLKAMSPARSISLEELEVSAKMVTDLIEAQ

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at position 73, which has the amino acid sequence set forth in SEQ ID NO: 32, provided below.

[SEQ ID NO: 32]
MTEPLILQPAKPADACVIWLHGLGADRYDFMPVAEALQESLLTTRFVLP

QAPTRPVTINGGYEMPSWYDIKALSPARSISLEELEVSAKMVTDLIEAQ

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at positions 28, and 73, which has the amino acid sequence set forth in SEQ ID NO: 33, provided below.

[SEQ ID NO: 33]
MTEPLILQPAKPADACVIWLHGLGADRTDFMPVAEALQESLLTTREVLP

QAPTRPVTINGGYEMPSWYDIKAVSPARSISLEELEVSAKMVTDLIEAQ

KRTGIDASRIFLAGFSQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at positions 25, and 73, which has the amino acid sequence set forth in SEQ ID NO: 34, provided below.

[SEQ ID NO: 34]
MTEPLILQPAKPADACVIWLHGLGAGRYDFMPVAEALQESLLTTRFVLP

QAPTRPVTINGGYEMPSWYDIKAVSPARSISLEELEVSAKMVTDLIEAQ

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at positions 25, and 28, which has the amino acid sequence set forth in SEQ ID NO: 35, provided below.

[SEQ ID NO: 35]
MTEPLILQPAKPADACVIWLHGLGGDRTDFMPVAEALQESLLTTRFVLP

QAPTRPVTINGGYEMPSWYDIKAMSPARSISLEELEVSAKMVTDLIEAQ

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at positions 70, and 73, which has the amino acid sequence set forth in SEQ ID NO: 36, provided below.

[SEQ ID NO: 36]
MTEPLILQPAKPADACVIWLHGLGADRYDFMPVAEALQESLLTTREVLP

QAPTRPVTINGGYEMPSWYDLKAASPARSISLEELEVSAKMVTDLIEAQ

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at positions 70, and 73, which has the amino acid sequence set forth in SEQ ID NO: 37, provided below.

[SEQ ID NO: 37]
MTEPLILQPAKPADACVIWLHGLGADRYDFMPVAEALQESLLTTRFVLP

QAPTRPVTINGGYEMPSWYDLKALSPARSISLEELEVSAKMVTDLIEAQ

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at position 30, which has the amino acid sequence set forth in SEQ ID NO: 38, provided below.

[SEQ ID NO: 38]
MTEPLILQPAKPADACVIWLHGLGADRYDHMPVAEALQESLLTTRFVLP

QAPTRPVTINGGYEMPSWYDIKAMSPARSISLEELEVSAKMVTDLIEAQ

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at positions 138, and 139, which has the amino acid sequence set forth in SEQ ID NO: 39, provided below.

[SEQ ID NO: 39]
MTEPLILQPAKPADACVIWLHGLGADRYDFMPVAEALQESLLTTRFVLP

QAPTRPVTINGGYEMPSWYDIKAMSPARSISLEELEVSAKMVTDLIEAQ

KRTGIDASRIFLAGESQGGAVVFHTAFINWQGPLGGVIAVNTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at position 25, which has the amino acid sequence set forth in SEQ ID NO: 40, provided below.

[SEQ ID NO: 40]
MTEPLILQPAKPADACVIWLHGLGGDRYDFMPVAEALQESLLTTRFVLP

QAPTRPVTINGGYEMPSWYDIKAMSPARSISLEELEVSAKMVTDLIEAQ

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at positions 70, and 73, which has the amino acid sequence set forth in SEQ ID NO: 41, provided below.

[SEQ ID NO: 41]
MTEPLILQPAKPADACVIWLHGLGADRYDEMPVAEALQESLLTTRFVLP

QAPTRPVTINGGYEMPSWYDLKAVSPARSISLEELEVSAKMVTDLIEAQ

-continued

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at positions 70, and 73, which has the amino acid sequence set forth in SEQ ID NO: 42, provided below.

[SEQ ID NO: 42]
MTEPLILQPAKPADACVIWLHGLGADRYDFMPVAEALQESLLTTRFVLP

QAPTRPVTINGGYEMPSWYDLKASSPARSISLEELEVSAKMVTDLIEAQ

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHEVLPQEIHDIGAWLAARLG.

In certain embodiments, the esterase of the present disclosure is carboxylesterase from *Pseudomonas fluorescens* modified by an amino acid substitution at positions 25, 28, 29, 30, 31, 200, and 201, which has the amino acid sequence set forth in SEQ ID NO: 43, provided below.

[SEQ ID NO: 43]
MTEPLILQPAKPADACVIWLHGLGAGRTSHRPVAEALQESLLTTRFVLP

QAPTRPVTINGGYEMPSWYDIKAMSPARSISLEELEVSAKMVTDLIEAQ

KRTGIDASRIFLAGESQGGAVVFHTAFINWQGPLGGVIALSTYAPTFGD

ELELSASQQRIPALCLHGQYDDVVQNAMGRSAFEHLKSRGVTVTWQEYP

MGHTILPQEIHDIGAWLAARLG.

In certain embodiments, the present disclosure further includes a nucleic acid sequence (e.g., a DNA sequence or an RNA sequence, optionally comprised within a vector) encoding a modified esterase as disclosed herein, such as the modified esterase of any one of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, and SEQ ID NO: 43. Such a nucleic acid sequence may optionally be codon optimized for expression in a host organism.

3.2 Enzymatic Ester Hydrolysis to Obtain Compound I

To synthesize Compound I, an enzyme of any one of SEQ ID NO: 1-43 can be used to enzymatically treat a solution including an anthocyanin or a mixture of anthocyanins (i.e., a mixture of a mono- and/or a diacylated anthocyanins), such that the anthocyanin compounds in the solution are selectively deacylated, resulting in either Compound I or II as the product. The solution can be, e.g., a fruit of vegetable extract, such as red cabbage juice or extract. The anthocyanins in the solution can be, e.g., an anthocyanin compound of any one of Compounds A-F, I, and II.

In certain embodiments, the enzymatic treatment of a solution (e.g., red cabbage juice or extract) by contacting the solution with an esterase of any one of SEQ ID NO: 1-43 results in the increase of the amount of Compound I in the solution by about 1-fold, about 10-fold, about 20-fold, about 30-fold, about 40-fold, about 50-fold, about 60-fold, about 70-fold, about 80-fold, about 90-fold, or about 100-fold relative to the amount of Compound I occurring in the solution (e.g., red cabbage juice or extract) prior to the enzymatic treatment. In certain embodiments, following enzymatic treatment of the solution, Compound I is present in the solution in an amount of about 40%, about 45%, about 50%, about 55%, about 60%, about 65%, about 70%, about 75%, about 80%, about 85%, about 90%, about 95%, about 98%, or about 100% of the total anthocyanin content of the solution. In other embodiments, the solution further comprises an amount of Compound II, which can be separated from Compound I according to the procedures disclosed herein.

The ester hydrolysis of an anthocyanin to Compound I can be catalyzed by a solution including one particular enzyme of SEQ ID NO: 1-43, or a mixture of enzymes selected from one of SEQ ID NO: 1-43. In certain embodiments, one or more enzymes of SEQ ID NO: 1-43 can be used to convert one or more diacylated anthocyanins in red cabbage juice to Compound I. In certain embodiments, one enzyme of SEQ ID NO: 1-43 is used to convert one or more diacylated anthocyanins in red cabbage juice to Compound I. In certain other embodiments, two enzymes of SEQ ID NO: 1-43 are used to convert one or more diacylated anthocyanins in red cabbage juice to Compound I. In certain other embodiments, three enzymes of SEQ ID NO: 1-43 are used to convert one or more diacylated anthocyanins in red cabbage juice to Compound I. In certain other embodiments, four or more enzymes of SEQ ID NO: 1-43 are used to convert one or more diacylated anthocyanins in red cabbage juice to Compound I.

The enzymatic ester hydrolysis of the solution can occur in a buffer solution having a pH of about 6.5-8 at a temperature of about 18-35° C. The amount of the enzyme of SEQ ID NO: 1-43 used for the enzymatic ester hydrolysis can be, for example, at least about 0.25 mg (e.g., at least about 0.30 mg, at least about 0.35 mg, at least about 0.40 mg, at least about 0.45 mg, at least about 0.50 mg, at least about 0.55 mg, at least about 0.60 mg, at least about 0.65 mg, at least about 0.70 mg, at least about 0.75 mg, at least about 0.80 mg, at least about 0.85 mg, at least about 0.90 mg, at least about 1.0 mg, at least about 1.5 mg, at least about 2.0 mg) enzyme per about 10 mg of substrate (e.g., a solution containing an anthocyanin, such as red cabbage juice or extract). An exemplary reaction is described in Example 1; however, one of ordinary skill in the art would recognize that reaction conditions other than those described below can be used for the enzymatic ester hydrolysis described herein, and would be able to determine the appropriate conditions for the reaction.

In certain embodiments, the one or more enzymes of SEQ ID NO: 1-43 catalyzes the hydrolysis of a compound of any one of Compounds A-C in a solution, e.g., of red cabbage juice or extract, to produce Compound II. In certain embodiments, the enzymatic treatment of a solution, e.g., red cabbage juice or extract, results in a solution where Compounds I and II make up the major anthocyanin content of the solution. In certain embodiments, Compounds I and II is present in an amount of at least about 40%, about 50%, about 60%, about 70%, about 80%, about 90%, about 95%, about 96%, about 97%, about 98%, about 99%, or about 100% of the total anthocyanin content of the solution, e.g., the red cabbage juice, that has undergone the enzymatic treatment disclosed herein. In certain embodiments, after the enzymatic treatment, Compound I is present in the solution in an amount of about 40%, about 45%, about 50%, about 55%, about 60%, about 65%, about 70%, about 75%, about 80%, about 85%, about 90%, about 95%, about 96%, about 97%, about 98%, about 99%, or about 100%, or from about 40% to about 100%, from about 40% to about 60%, from about 40% to about 80%, from about 60% to about 80%, from about 60% to about 100%, or from about 80% to about 100% by weight of the solution.

3.3 Isolation of Anthocyanins

In certain embodiments, the enzymatic treatment of fruit and/or vegetable juice and/or extract described herein provides a mixture of one or more anthocyanins, and further purification is necessary to isolate particular anthocyanins of interest. In certain embodiments, the purification process includes one or more of enzyme precipitation, solid-phase extraction, and preparatory HPLC. In some embodiments, the purification process includes (i) enzyme precipitation, followed by (ii) solid-phase extraction, optionally followed by (iii) preparatory HPLC.

In certain embodiments, the enzyme precipitation step comprises adjusting the pH of the mixture. In certain embodiments, the pH of the mixture is adjusted to a low pH of from about 1 to about 2.5, from about 1 to about 1.5, from about 1.25 to about 1.75, from about 1.5 to about 2, from about 1.75 to about 2.25, or from about 2 to about 2.5. In a particular embodiment the pH of the mixture is adjust to pH of about 1.10. In certain embodiments, a strong inorganic acid is used to adjust pH of the mixture. In certain embodiments, the acid can be hydrochloric acid, sulfuric acid, or orthophosphoric acid. In certain embodiments, after lowering pH of the mixture, the mixture is cooled in an ice bath for a time period of from about 1.5 hours to about 2.5 hours and the liquid can then be transferred to centrifuge tubes and centrifuged. In certain embodiments, the mixture is centrifuged for from about 2 to about 10 minutes. In a particular embodiment, the mixture is centrifuged for about 5 minutes. In certain embodiments, the mixture is centrifuged at from about 3000 rcf to about 4000 rcf. In a particular embodiment, the mixture is centrifuged at about 3540 rcf for about 5 minutes.

In certain embodiments, after the centrifugation step, the supernatant is decanted and subsequently vacuum filtered. In certain embodiments, the resulting material is further purified by using Solid Phase Extraction.

In certain embodiments, the mixture contains two or more anthocyanins that need to be separated from each other. In certain embodiments, the anthocyanins are separated by using High Performance Liquid Chromatography (HPLC). In certain embodiments, the HPLC system is equipped with a diode array detector (DAD). In certain embodiments, ethanol must be removed from the mixture prior to preparatory HPLC-DAD. In certain embodiments, the ethanol is removed by placing the mixture in a warm water bath at a temperature of from about 25° C. to about 45° C. with a steady stream of an inert gas such as nitrogen, argon, or helium passing over. In certain embodiments, deionized water is added to the mixture to account for the volume of ethanol removed.

LC columns of various length, diameter, particle size and pore size can be used to separate two or more anthocyanins, depending on the identity of the anthocyanin and the amount of the solution. In a specific embodiment, a 250 mm L×50 mm D Phenomenex Luna C18 (2) preparatory LC column with particle size of 10 microns and pore size of 100 Å is used to isolate Compound I from a mixture, wherein the major components are Compound I and Compound II.

4. Food Products

The non-artificial blue anthocyanin-containing colorants of the present disclosure, i.e., Compound I, can be used in a colorant composition and can be added to food products, for example, to alter the color characteristics of the food product. The colorant composition can be an edible colorant composition including Compound I with a metal ion at a pH of from about 6 to about 8. For example, and not by way of limitation, the colorant can be used within a coating (i.e., within an edible colorant composition comprising the colorant) for confections to produce a blue-colored coating. Alternatively, or additionally, the non-artificial blue anthocyanin-containing colorant, i.e., Compound I, can be combined with another colorant, e.g., a non-artificial yellow colorant, to produce a non-artificial green colorant.

In certain embodiments, the colorants of the present disclosure can color a food product or a portion thereof.

In certain embodiments, the non-artificial blue anthocyanin-containing colorants can be used in a wide variety of edible products. Non-limiting examples of suitable food products include chocolates, chewing gum compositions, hard and soft confectionery products, dairy products, food products of the beverage category where the product is at about a neutral pH, food products of the frozen food category including frozen dairy products, pharmaceuticals and food categories described herein.

As used herein, "beverage category" can refer to beverages, beverage mixes and concentrates, including but not limited to, alcoholic and non-alcoholic ready to drink and dry powdered beverages, where the beverage is at about a neutral pH. Additional non-limiting examples of beverages can include carbonated and non-carbonated beverages, e.g., sodas, fruit or vegetable juices.

As used herein, "frozen food category" refers to chilled or frozen food products that have a neutral pH. Non-limiting examples of food products of the frozen food category can include ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yogurt, artisanal ice cream, frozen ready meals, frozen pizza, chilled pizza, frozen soup, frozen pasta, frozen processed red meat, frozen processed poultry, frozen processed fish/seafood, frozen vegetables, frozen processed vegetables, frozen meat substitutes, frozen potatoes, frozen bakery products and frozen desserts.

As used herein, "snack food category" refers to any food that can be a light informal meal including, but not limited to sweet and savory snacks and snack bars, where the foods have a neutral pH. Examples of snack foods include, but are not limited to, fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

4.1 Confectionary Products

In certain embodiments, an edible colorant composition (e.g., comprising Compound I) of the presently disclosed subject matter can be incorporated into a confectionery product. Non-limiting examples of confectionery products include cakes, cookies, pies, candies, chocolates, chewing gums, gelatins, ice creams, sorbets, puddings, jams, jellies, cereal and other breakfast foods, canned fruits and fruit sauces.

In certain embodiments, an edible colorant composition of the present disclosure can be incorporated into the confections by admixing the edible colorant composition into a confectionery product, e.g., a hard or soft confectionery product. For example, and not by way of limitation, the present disclosure provides methods for enhancing or modulating the blue color of an edible product that comprises (a) providing at least one food product, or a precursor thereof, and (b) combining the food product or precursor thereof with one or more blue edible colorant compositions, disclosed herein, so as to form a modified edible food product. Additionally, the methods can be used for enhancing or modulating the green color of an edible product by (a) providing at least one food product, or a precursor thereof, and (b) combining the food product or precursor thereof with one or more green edible colorant compositions, e.g., an edible colorant composition comprising a blue colorant and a yellow colorant, so as to form a modified edible food product.

In certain embodiments, certain amounts of an edible colorant composition of the present disclosure can be incorporated into a confectionery product. The amount of the edible colorant composition that is used can depend on a number of factors including, but not limited to, the type of bulking agent or carrier employed, method of application, use rate, the type of colorant employed and the intensity of color desired.

In certain embodiments of the present disclosure, the edible colorant composition is admixed with a confection or a component of a confection, where the edible colorant composition is added in amounts to give blue color that can range in intensity from a very pale light cyan blue through to a very dark cyan blue color. The edible colorant composition can pure or nearly pure Compound I, e.g., with metal ion, or the edible colorant composition can contain other ingredients to aid in the incorporation of Compound I into various types of food products. In certain embodiments, the edible colorant composition may contain, for example, from about 0.01% to about 0.1% weight/weight (w/w), or from about 0.07% to about 10% (w/w), or from about 5% to about 35% (w/w) of Compound I. In other embodiments, the edible colorant composition may contain from about 0.005% to about 0.01% (w/w) of Compound I. Depending on the amount of Compound I contained in the colorant composition, more or less colorant composition can be used to achieve the desired color properties in the confection or component of the confection. Such amounts result in an effective use rate, which can be expressed as the percent (w/w) of Compound I added to the confection, confection component, food product or portion thereof. In certain embodiments, the effective use rate of Compound I is an amount of from about 0.0001% to about 10% (w/w), or from about 0.0005% to about 1.0% (w/w), or from about 0.001% to about 0.5% (w/w), or from about 0.005% to about 0.2% (w/w), or from about 0.01% to about 0.1% (w/w), or from about 0.02% to about 0.08% (w/w), and values in between.

In certain embodiments, the edible colorant composition of the present disclosure can be incorporated in a confectionery product of the dragée type, which can include a core and a layer of granulated sugar. Non-limiting examples of the type of cores in a dragée type confectionery product can include a non-artificial center (e.g., almond, hazelnut or groundnut) or a "confectionery" center (e.g., caramel, fondant or chocolate). The cores can then be coated with chocolate, with successive layers of sugars or other substances such as polyols (e.g., erythritol, xylitol, maltitol, or sorbitol), gums and non-artificial polymers, that can further include one or more color compositions of the present disclosure. In certain embodiments, the present disclosure provides for confectionery products that are coated with a blue edible color composition disclosed herein. In other embodiments, the present disclosure provides for confectionery products that are coated with a green edible color composition disclosed herein.

In certain embodiments, the methods for manufacturing compositions of the dragée type can comprise the deposition of a plurality of sublayers, for example between about 5 and about 30, by a succession of phases of application and drying carried out, for example, in a pan. In a hard panning process, multiple applications of a highly concentrated sugar syrup can be used to build up the uncolored portion of a sugar coating on an edible product center. This can be followed by multiple applications of a concentrated sugar syrup containing an edible colorant composition of the present disclosure. In certain embodiments, the hard panning process comprises the repetitive application of thin layers of a coating solution or composition onto an intermixed mass of centers, and the drying of each layer of coating solution or composition during which the sugar in the coating crystallizes between the applications of layers. Additional non-limiting examples of methods for producing hard panned confectionaries are provided in International Patent Publication Nos. WO 2014/150438 and WO 2014/152417, the disclosures of which are incorporated herein by reference.

In certain embodiments, where a coating is to be colored, an edible colorant composition of the present disclosure can be added to the coating solution in the later stages of the coating process. For example, and not by way of limitation, the edible colorant composition comprises a monoacylated anthocyanin, e.g., of Compound I, a metal ion, or salt form thereof, and a pH adjusting ingredient having a pH of about 6 to about 8. For a hard panned confectionery, following the application of a number of layers of the uncolored sugar syrup to build up the sugar coating, a number of applications of a sugar syrup comprising an edible colorant composition, disclosed herein, are applied to provide the color coat. In certain embodiments, the color coat can require 30 or more applications of a colored coating comprising the edible colorant composition solution to achieve the desired color.

In certain embodiments, when an edible colorant composition is included in one or more sugar syrups used for hard panned coating, the hard panned coating has a visible color provided by the edible colorant composition. A hard panned confection comprising an edible product center coated with this same hard panned coating also has a visible color provided by the edible colorant composition. In certain embodiments, the hard panned coating has a blue color, and a hard panned confection coated with this same hard panned coating has a blue color. The blue color can be provided, at least in part, by a blue edible colorant composition, disclosed herein, incorporated in the coating.

In certain embodiments, the hard panned coating has a green color, and a hard panned confection coated with this same hard panned coating has a green color. In certain embodiments, the green color can be provided by an edible colorant composition comprising the combination of a blue colorant (e.g., Compound I with a metal ion), disclosed herein, and a non-artificial yellow colorant incorporated in the coating. Examples of non-artificial yellow colorants can include, but are not limited to, curcuminoids (e.g., from turmeric), carotenoids (e.g., from saffron, gac fruit, and gardenia), annatto (e.g., from achiote) and combinations thereof. In certain embodiments, the non-artificial yellow colorant is derived from turmeric. In other embodiments, the non-artificial yellow colorant is gardenia yellow.

In certain embodiments, the present disclosure provides edible products in the form of a hard coated confectionery product comprising a center core and at least one coating layer that comprises the edible colorant composition disclosed herein and crystallized sugar. For example, and not by way of limitation, the present disclosure provides a hard panned confection that comprises (a) an edible core and (b) a hard panned coating that comprises a plurality of coating layers, wherein at least one of the coating layers comprises an edible colorant composition of the present disclosure. For example, and not by way of limitation, the edible core can comprise chocolate.

5. Methods of Preparation of the Colorant Compositions

Edible colorant compositions containing Compound I can be either liquid or solid preparations. In certain embodiments, Compound I is dissolved in water, and the pH is adjusted to a pH value in the range of about 6 to about 8, with about pH 7 being optimal. In certain embodiments, from about 0.3 to about 1.0 mol. equiv. (e.g., about ⅓ mol. equiv. or about 1 mol. equiv.) of an edible aluminum or iron salt is added to the solution. If the final format is to be a dispersible solid, then a suitable dissolved solid such as a maltodextrin is dissolved in the colorant solution. The total dissolved solids should be about 10-15% of the colorant solution, and this material can them be spray dried using an apparatus known in the art. The content of Compound I can be from about 1% to about 10% (e.g., about 2% to about 9%, about 3% to about 7%, about 4% to about 6%, about 2% to about 7%, about 2% to about 4%, about 5% to about 7%, or about 5% to about 9%) of the final dried colorant composition. When a liquid preparation is preferred, it may be preferable to maintain the solution at a low pH, about 2-3 to improve the long term stability of Compound I. From about 0.3 to about 1.0 mol. equiv. (e.g., about ⅓ mol. equiv. or about 1 mol. equiv.) of an edible aluminum or iron salt is added to the solution.

In certain embodiment, suitable excipients, known in the art, can be added to help maintain microbiological stability of the color composition. Refrigerated or frozen storage of a liquid color composition is preferred for maximum stability.

EXAMPLES

The presently disclosed subject matter will be better understood by reference to the following Examples, which are provided as exemplary of the disclosure and should not be construed as limiting the scope of the disclosure in any way.

Example 1: Design of Esterases for Selectively Deacylation of Anthocyanins

Compound I is a compound that can be used in food products as a non-artificial blue colorant, but challenges have arisen in isolating sufficient quantities of the pure product of Compound I from a mixture of similar compounds. It is contemplated herein that the amount of Compound I in a composition can be enriched by modifying an enzyme to specifically catalyze the synthesis of Compound I from a mixture of several anthocyanin compounds.

Database Mining and Sequence Comparison.

In the first round of database mining, we searched BRENDA for representative enzymes from a variety of enzyme classifications, favoring genes with crystal structures. In round 2 of mining, we looked specifically at genes active on substrates similar to anthocyanins, as well as enzymes that perform similar chemistry to the active gene found in round 1, #37 of Table 9. Genome mining in round 3 was completed using phmmer and jackhammer searches on HMMER, an online application that uses Hidden Markov Model to identify sequences similar to a submitted target sequence (Potter et al., "HMMER web server: 2018," *Nucleic Acids Research.* 46(W1):W200-W204, 2018). Sequences were selected from the PDB and Ensembl Genomes Bacteria databases. Sequences were aligned and percentage identities calculated using the MUSCLE Alignment tool on Geneious 10.1.3.

A table of the identified enzymes is provided below in Table 9. A table of the sequences of each of the enzymes tested is provided below in Table 10.

TABLE 9

Enzymes tested in study

| ID # | EC # | UniProt ID | PDB | Enzyme Classification | Domain |
|---|---|---|---|---|---|
| 1 | 3.1.1.1 | Q1QYJ5 | | Carboxylesterase | Bacteria |
| 2 | 3.1.1.1 | A0A1J8PUW1 | | Carboxylesterase | Bacteria |
| 3 | 3.1.01.- | Q5NI32 | 4F21 | Carboxylesterase/phospholipase | Bacteria |
| 4 | 3.1.1.57 | O87170 | 4DI9 | 2-pyrone-4,6-dicarbaxylate hydrolase | Bacteria |
| 5 | 3.1.1.45 | P0A114 | 1ZI8 | Dienelactonase mutant | Bacteria |
| 6 | 3.1.1.1 | Q06174 | 1TQH | Carboxylesterase | Bacteria |
| 7 | 3.1.3.1 | B8Y562 | 4RGY | Alkaline esterase | Bacteria |
| 8 | 3.1.1.91 | F8QQ74 | | 2-oxo-3-(5-oxofuran-2-ylidene) propanoate lactonase | Bacteria |
| 9 | 3.5.2.6 | F8CAF0 | | Beta-lactamase | Bacteria |
| 10 | 3.1.1.27 | Q988B9 | 3AJ3 | 4-pyridoxolactonase | Bacteria |
| 11 | 3.1.1.92 | A6XIG7 | | 4-sulfomuconolactone hydrolase | Bacteria |
| 12 | 3.5.2.6 | B2BSN6 | | Beta-lactamase | Bacteria |
| 13 | 3.5.2.6 | P00811 | 2FFY | Beta-lactamase | Bacteria |
| 14 | 3.1.1.65 | A3LZU8 | | L-rhamnono-gamma-lactonase | Eukaryote |
| 15 | 3.1.8.1 | P15034 | 2V3Z | Xaa-Pro aminopeptidase | Bacteria |
| 16 | 3.1.1.68 | R0CVD2 | | Xylono-1,4-lactonase | Bacteria |
| 17 | 3.1.1.1 | G4RFI7 | 5DWD | Esterase | Bacteria |
| 18 | 3.1.1.83 | Q9EX73 | | Monoterpene epsilon-lactone hydrolase | Bacteria |
| 19 | 3.1.1.15 | Q1JUP5 | | L-arabinolactonase | Bacteria |
| 20 | 3.2.1.8 | P51584 | 1GKK | Feruloyl esterase | Bacteria |

TABLE 9-continued

Enzymes tested in study

| ID # | EC # | UniProt ID | PDB | Enzyme Classification | Domain |
|---|---|---|---|---|---|
| 21 | 3.1.1.17 | B0RN69 | 3DR2 | Exported gluconolactonase | Bacteria |
| 22 | 3.1.1.73 | O42807 | 1USW | Ferulic acid esterase | Bacteria |
| 23 | 3.1.1.25 | B2LYJ5 | | Levo-lactonase | Eukaryote |
| 24 | 3.1.1.17 | A9CPS8 | | Lactonase | Eukaryote |
| 25 | 3.5.2.6 | Q8GCU7 | | Metallo-beta-lactamase VIM-6 | Bacteria |
| 26 | 3.5.2.6 | Q8KRJ3 | 2WHG | Beta-lactamase VIM-4 | Bacteria |
| 27 | 3.1.1.84 | Q9L9D7 | 1JU3 | Cocaine esterase | Bacteria |
| 28 | 3.1.1.31 | Q9GRG6 | 3EB9 | 6-phosphogluconolactonase | Eukaryote |
| 29 | 3.1.1.24 | Q13KT2 | 2XUA | 3-oxoadipate enol-lactonase | Bacteria |
| 30 | 3.1.1.1 | A0A0M3KKY6 | 4UHC | Carboxylesterase | Bacteria |
| 31 | 3.1.1.95 | Q54528 | 1QOR | Aclacinomycin methylesterase | Bacteria |
| 32 | 3.1.1.81 | P0CJ63 | 3DHA | N-acyl homoserine lactonase AiiA | Bacteria |
| 33 | 3.1.1.11 | P0C1A9 | 2NSP | Pectinesterase A | Bacteria |
| 34 | 3.1.1.1 | O28558 | 1JJI | Carboxylesterase | Archaea |
| 35 | 3.1.1.4 | A0A243LS46 | | Esterase | Bacteria |
| 36 | 3.1.1.1 | Q7SIG1 | 1EVQ | Carboxylesterase | Bacteria |
| 37 | 3.1.1.2 | B5BLW5 | 5L2P | Arylesterase | Archaea |
| 38 | 3.1.1.1 | F0NDQ1 | 5LK6 | Lipase carboxylesterase | Bacteria |
| 39 | 3.1.1.1 | Q976W8 | 3AIK | Carboxylesterase | Bacteria |
| 40 | 3.1.1.1 | A0A139SSC5 | | Carboxylesterase | Bacteria |
| 41 | 3.1.1.1 | A0A2U2AP80 | | Carboxylesterase | Bacteria |
| 42 | 3.1.1.1 | L8MEL5 | | Carboxylesterase | Bacteria |
| 43 | 3.1.1.1 | A0A127MYW2 | | Carboxylesterase | Bacteria |
| 44 | 3.1.1.1 | Q9HXE7 | 3CN9 | Carboxylesterase | Bacteria |
| 45 | 3.1.1.1 | A0A078LXQ1 | | Alpha/beta-hydrolase | Bacteria |
| 46 | 3.1.1.1 | Q53547 | 1AUR | Carboxylesterase | Bacteria |

TABLE 10

Amino acid sequences of enzymes tested in Example 1

| SEQ ID NO: | ID# | Sequence |
|---|---|---|
| 44 | 1 | MADSSPLIIEPRQARAADATVILLHGLGADGHDFEPLVPALPLAKDLAVRFVLP HAPRMPVTVNGGMEMPAWYDILDMNLGRRIDEAQLKASADMVHGLIDAEIA RGIDSRRIIVAGFSQGGAVAYHAALTYPKPLGGLLALSTYFATATSIEPSEANR ALPIEVHHGSFDPVVPEALGHEGAERAEALGYAVTYRTYPMQHALCPEQIEDI GQWLNARLGAKEAGGSLEHHHHHH |
| 45 | 2 | MTAPGELIIEPKDGQPADACVFIIHGLGADGHDFEPLVPALALPKDSRVRFIMP HAPRLPVTINGGMVMPAWYDILAMDLGRRVDERQLKQSAERIQALIQEQIDQ GIDSQRIIVAGFSQGGAVAYHAALTFPAPLGGLLAMSTYFATADNIDLAEANR QIPIEVQHGNFDPIVPESLGRSGADRLKEMGYAVNYRQYPMAHALCPQQVNDI GKWLSARLNGGSLEHHHHHH |
| 46 | 3 | MNYELMEPAKQARFCVIWLHGLGADGHDFVDIVNYFDVSLDEIRFIFPHADIIP VTINMGMQMRAWYDIKSLDANSLNRVVDVEGINSSIAKVNKLIDSQVNQGIAS ENIILAGFSQGGIIATYTAITSQRKLGGIMALSTYLPAWDNFKGKITSINKGLPIL VCHGTDDQVLPEVLGHDLSDKLKVSGFANEYKHYVGMQHSVCMEEIKDISNF IAKTFKIGGSLEHHHHHH |
| 47 | 4 | MTNDERILSWNETPSKPRYTPPPGAIDAHCHVFGPMAQFPFSPKAKYLPRDAG PDMLFALRDHLGFARNVIVQASCHGTDNAATLDAIARAQGKARGIAVVDPAI DEAELAALHEGGMRGIRFNFLKRLVDDAPKDKFLEVAGRLPAGWHVVIYFEA DILEELRPFMDAIPVPIVIDHMGRPDVRQGPDGADMKAFRRLLDSREDIWFKA TCPDRLDPAGPPWDDFARSVAPLVADYADRVIWGTDWPHPNMQDAIPDDGL VVDMIPRIAPTPELQHKMLVTNPMRLYWSEEMGGSLEHHHHHH |
| 48 | 5 | MLTEGISIQSYDGHTFGALVGSPAKAPAPVIVIAQEIFGVNAFMRETVSWLVDQ GYAAVCPDLYARQAPGTALDPQDERQREQAYKLWQAFDMEAGVGDLEAAIR YARHQPYSNGKVGLVGYCLGGALAFLVAAKGYVDRAVGYYGVGLEKQLKK VPEVKHPALFHMGGQDHFVPAPSRQLITEGFGANPLLQVHWYEEAGHSFART SSSGYVASAAALANERRLDFLAPLQSKKPGGSLEHHHHHH |
| 49 | 6 | MKIVPPKPFFFEAGERAVLLLHGFTGNSADVRMLGRFLESKGYTCHAPIYKGH GVPPEELVHTGPDDWWQDVMNGYEFLKNKGYEKIAVAGLSLGGVFSLKLGY TVPIEGIVTMCAPMYIKSEETMYEGVLEYAREYKKREGKSEEQIEQEMEKFKQ TPMKTLKALQELIADVRDHLDLIYAPTFVVQARHDEMINPD SANIIYNEIESPV KQIKWYEQSGHVITLDQEKDQLHEDIYAFLESLDWGGSLEHHHHHH |
| 50 | 7 | MALFQCDFFSDVLGLSTSMTVILPQETTGQIGMAGGSERREHPTLFLLHGLSDD HTIWLRRTSIERYVAEMGLAVVMPAVHRSFYTDMAHGLQYWTFISEELPALA |

TABLE 10-continued

Amino acid sequences of enzymes tested in Example 1

| SEQ ID NO: | ID# | Sequence |
|---|---|---|
| | | RSFFPLATAREDTFVAGLSMGGYGALKLGMRHPERFAAAASLSGALDITFDPA<br>EHIAMEDDVWVAEQRNIFGDLAALPGSDHDLFALAERMAQSDGPVPKLYQCC<br>GTEDFLYEDNVRFRDHVRGLGLDFMYEESPGEHEWGYWDAQIQRVLAWLPL<br>RPPGTAPAGGSLEHHHHHH |
| 51 | 8 | MATETIAMDWVDIGTNGESRLAYLARPVVTGRLPAVIVMPAIHGINTYIKDVA<br>IDLAKAGFVALLIDIHSPEQEPDLSNAEKIQIAVETLDDRKVLKDVDAAVRYLE<br>QHAAVRADRLGILGFCVGGTYALLAARTPAIRVSVGFYGLLEYQSRTDNKPVS<br>PLDSVAQFTAPILFHVGDKDPWIDSKMLAEFTKRMQQHQKSYELCIYRGAGH<br>AFHEHFRDAYRPIAAQSAWNNTLIYLRWHLCGKRTVGGSLEHHHHHH |
| 52 | 9 | MNGLRWRLTGVVMAWVLVAPLAEAANVKQEVDRYISGFHQKGLFNGTVLV<br>ANERGILLKKGYGAANLEWKVPNAPDTKFRIGSITKSFTATVILQLAAEGKLQL<br>DDPITKHLPDYRKDTGDRVTITHLLNHTSGIPSYTSKPAIMKDADGFESVAAFV<br>KKACSDDLEFEPGTKYAYNNSGYFLLGAIIEKLTGQTYAEAVQARILGPLGMK<br>DTGYDVSATVLPKRASGYAQAPGGIVNAAWLDMNLPYAAGSLYSTVEDLYR<br>WERAFHGDTLLPAALKQKMLTPGLAHYGFGWVMSDMTLHDGKTKLPGIFHT<br>GGINGFSSILVRVPERKEAVILLDNMTHGGLQELAGGVLSILHGLTPRPARMPI<br>GNVMMESLGKGSVAQAIATYRTLKKTQAEYDFSERHLNTVGYHLLRSGRA<br>ADAIEVFKLNVEMFPEAANCHDSLGEAYAAHGDKARAITSYRKALELAPKNE<br>HAVKMLEQLEEPAAKRGGSLEHHHHHH |
| 53 | 10 | MSDTKVYLLDGGSLVLDGYHVFWNRGPGGEVRFPVYSILIEHAEGRFLIDTGY<br>DYDHVMKVLPFEKPIQEKHQTIPGALGLLGLEPRDIDVVVNSHFHFDHCGGNK<br>YFPHAKKICHRSEVPQACNPQPFEHLGYSDLSFSAEAAEARGATAQLLEGTTR<br>ANSTFEGIDGDVDLARGVKLISTPGHSIGHYSLLVEFPRRKPILFTIDAAYTQKS<br>LETLCQAAFHIDPVAGVNSMRKVKKLAEDHGAELMYSHDMDNFKTYRTGTQ<br>FYGGGSLEHHHHHH |
| 54 | 11 | MLPADQAGIPPCQGPRARSAPISFAIPKGAWDTHLHVFGPTAVFPYAEKRPYTP<br>PDSPLEDYLALMERLGIERGVCVHPNVHGIDNSVTIDAVERSDRRLLGIIKPHR<br>VMTFTELRDLKTRGVRGVRFAFNPQHGSGALDTELFERMHGWCRELDWCIN<br>MHFAPDALEGLCDLIAGAETPIIIDHFGRVETAAGVNQLPFKILRDLATLDHVW<br>IKLTGADRISHSGVPYDDVVPFAHALSEIAPDRLLWGSDWPHSGYFDPKRMPD<br>DGDLLNLVARFAPDVALRHKILVDNPARLFGVIGGSLEHHHHHH |
| 55 | 12 | MKQRIALSLLALGPLLLVPRVYAAADEPMANIVEKAVQPLLEEYRIPGMAVAV<br>LKEGKPHYFNYGVANRESGRRISERTLFEIGSVSKTFTATLGTYAVVKGGFRLD<br>DKVSQHAPWLQNSAFDRVTMAQLATYSAGGLPLQFPDAVDSNERMRQYYRQ<br>WSPLYAAGTHREYSNPSIGLFGHLAASTLGQPFRQLMSQTLLPKLDLQHTYLE<br>VPDAAMVDYAYGYSKEDKPVRVNPGVLADEAYGIKTSAADLIKFVGANMTG<br>SGDKAVQQALAMTRTGFYSVGEMTQGLGWESYAYPVTEQALLAGNSPAVSF<br>KANPVKPFVAPRVMGNERLYNKTGSTNGFGAYVVFVPARGVGIVMLANRNY<br>PIEARVKAAYAIMRHLAPGGSLEHHHHHH |
| 56 | 13 | MFKTTLCALLITASCSTFAAPQQINDIVHRTITPLIEQQKIPGMAVAVIYQGKPY<br>YFTWGYADIAKKQPVTQQTLFELGSVSKTFTGVLGGDAIARGEIKLSDPTTKY<br>WPELTAKQWNGITLLHLATYTAGGLPLQVPDEVKSSSDLLRFYQNWQPAWAP<br>GTQRLYANSSIGLFGALAVKPSGLSFEQAMQTRVFQPLKLNHTWINVPPAEEK<br>NYAWGYREGKAVHVSPGALDAEAYGVKSTIEDMARWVQSNLKPLDINEKTL<br>QQGIQLAQSRYWQTGDMYQGLGWEMLDWPVNPDSIINGSDNKIALAARPVK<br>AITPPTPAVRASWVHKTGATGGFGSYVAFIPEKELGIVMLANKNYPNPARVDA<br>AWQILNALQGGSLEHHHHHH |
| 57 | 14 | MSKYKILDSHIHLYSLANIPLLHWDEGNPLHGNRRLDEYIENSQSTQFDVEGV<br>VWIECDAKIDLTQGLKGLENPIEEYLYICRNINGKLLPEEGVSTPFKRRLIKAMI<br>PFAPMPLGSAGVEEYVKALKTRNSSEFHLVKGFRYLIQDKPPLTISDPHFVSSF<br>QWLDSNGYVFDLGIDMRSGGLWQFKETLEVFKKVPNLKYIINHLTKPCLDFDP<br>ETIDSNPDFLSWKRLVTEMYITTPNSYMKLSGGFSEVEQDVALDVTSTSRHVY<br>PWFKVVYELWGPERTIFASNWPVCAIPAGQNLTEKWFQVCETLFDSIGMDEDT<br>RRKIYYSNAFKAYNIGGSLEHHHHHH |
| 58 | 15 | MSEISRQEFQRRRQALVEQMQPGSAALIFAAPEVTRSADSEYPYRQNSDFWYF<br>TGFNEPEAVLVLIKSDDTHNHSVLFNRVRDLTAEIWFGRRLGQDAAPEKLGVD<br>RALAFSEINQQLYQLLNGLDVVYHAQGEYAYADVIVNSALEKLRKGSRQNLT<br>APATMIDWRPVVHEMRLFKSPEEIAVLRRAGEITAMAHTRAMEKCRPGMFEY<br>HLEGEIHHEFNRHGARYPSYNTIVGSGENGCILHYTENECEMRDGDLVLIDAG<br>CEYKGYAGDITRTFPVNGKFTQAQREIYDIVLESLETSLRLYRPGTSILEVTGEV<br>VRIMVSGLVKLGILKGDVDELIAQNAHRPFFMHGLSHWLGLDVHDVGVYGQ<br>DRSRILEPGMVLTVEPGLYIAPDAEVPEQYRGIGIRIEDDIVITETGNENLTASVV<br>KKPEEIEALMVAARKQGGSLEHHHHHH |
| 59 | 16 | MNAVTCVWDLKATLGEGPIWYDDSLWFVDIKSHKIHNYNPATDERFSFDAPE<br>PVTFIAPLAPNARAGFVVGLKSGLHRFHPVMGGFKPLIQVESAELNNRPNDAT<br>VDHGGRLWFGTMHDDEEAKSGSLYRMDSTGVARMDKDICITNGPCVSPDGK |

TABLE 10-continued

Amino acid sequences of enzymes tested in Example 1

| SEQ ID NO: | ID# | Sequence |
|---|---|---|
| | | TLYHTDTLEKIIWAYDLAEDGTLSNKRGFVNFQGENAVYPDGSVVDSEGYLW<br>TALWGGFGVVRISPAGELVARIELPAPNVTKPCFGGPDLKTLYFTTARKGLSDE<br>TLAQYPLSGGLFGVRVDVAGQPQHEVRLVGGSLEHHHHHH |
| 60 | 17 | MTEPVKLSGPMLPAVSGAAKSLVVLLHGYGSDGRDLIALGQFWRDSFPDTMF<br>VAPNAPHVCGGNPFGYEWFPLDLERDRTLARLAGAETAHPVLDAFLADLWA<br>QTGLGPADTILVGFSQGAMMALYTGLRLPEPLKAIIAFSGLIVAPEKLEAEIASK<br>PPVLLIHGDLDDVVPVIGSETALPKLIDLGIDARLHISQGSGHTIAQDGLDTATA<br>FLREILGGSLEHHHHHH |
| 61 | 18 | MSATDTARAKELLASLVSMPDATIDDFRALYEQVCATFELPDDAQVEPVDAN<br>GADALWVSAPGVSADTVAVVVHGGGFTMGSAHGYRELGYRLSKSGNLRALV<br>VDYRLAPESPFPAPVDDVVAAYRYARSLDGVENVFLVGDSAGGGIAMSALITL<br>RDAGEQLPDAAVVLSPLVDLAGESPSLVDRAHLDPLPAAVLVNGMGGLYLNG<br>LDVRHPVASPMHGDLTGLPATLVLVGTDEGLHDDSTRLVDKLKAADVEVQLE<br>IGEGLPHIWPIFSFHPDAVAATDRIGEFLRSHVAAPRGGSLEHHHHHH |
| 62 | 19 | MQQIHPAGQATLLADTRNTLGEGATWCDRTRALYWVDIEGAQLWRCRADGS<br>DLTPWPMPERLACFALTDDPDVLLVGLATHLAFFDLRSGAFTRIVEVEPELPTR<br>LNDGRCDGSGAFVFGMKDEGAEPPRAVGGFYRLNADLTLERLALPPAAIANSI<br>GFSPDGSKMYFCDSLVREIFVCDYRPGGEVANVRPFARLTDPDGDPDGSIVDR<br>DGGLWNAQWGGRRVVRYGPDGVETDRVAVPTAQPSCTALDGEGRLYVTSA<br>RVGLSDDALADDPHAGGVFVAQTRHAGMATARFAGTPRGGSLEHHHHHH |
| 63 | 20 | MKNKRVLAKITALVVLLGVFFVLPSNISQLYADYEVVHDTFEVNFDGWCNLG<br>VDTYLTAVENEGNNGTRGMMVINRSSASDGAYSEKGFYLDGGVEYKYSVFV<br>KHNGTGTETFKLSVSYLDSETEEENKEVIATKDVVAGEWTEISAKYKAPKTAV<br>NITLSITTDSTVDFIFDDVTITRKGMAEANTVYAANAVLKDMYANYFRVGSVL<br>NSGTVNNSSIKALILREFNSITCENEMKPDATLVQSGSTNTNIRVSLNRAASILN<br>FCAQNNIAVRGHTLVWHSQTPQWFFKDNFQDNGNWVSQSVMDQRLESYIKN<br>MFAEIQRQYPSLNLYAYDVVNEAVSDDANRTRYYGGAREPGYGNGRSPWVQ<br>IYGDNKFIEKAFTYARKYAPANCKLYYNDYNEYWDHKRDCIASICANLYNKG<br>LLDGVGMQSHINADMNGFSGIQNYKAALQKYINIGCDVQITELDISTENGKFSL<br>QQQADKYKAVFQAAVDINRTSSKGKVTAVCVWGPNDANTWLGSQNAPLLFN<br>ANNQPKPAYNAVASIIPQSEWGDGNNPAGGGGGGKPEEPDANGYYYHDTFEG<br>SVGQWTARGPAEVLLSGRTAYKGSESLLVRNRTAAWNGAQRALNPRTFVPG<br>NTYCFSVVASFIEGASSTTFCMKLQYVDGSGTQRYDTIDMKTVGPNQWVHLY<br>NPQYRIPSDATDMYVYVETADDTINFYIDEAIGAVAGTVIEGPAPQPTQPPVLL<br>GDVNGDGTINSTDLTMLKRSVLRAITLTDDAKARADVDKNGSINSTDVLLLSR<br>YLLRVIDKFPVAENPSSSFKYESAVQYRPAPDSYLNPCPQAGRIVKETYTGING<br>TKSLNVYLPYGYDPNKKYNIFYLMHGGGENENTIFSNDVKLQNILDHAIMNGE<br>LEPLIVVTPTFNGGNCTAQNFYQEFRQNVIPFVESKYSTYAESTTPQGIAASRM<br>HRGFGGGFSMGGLTTWYVMVNCLDYVAYFMPLSGDYWYGNSPQDKANSIAE<br>AINRSGLSKREYFVFAATGSDHIAYANMNPQIEAMKALPHFDYTSDFSKGNFY<br>FLVAPGATHWWGYVRHYIYDALPYFFHEGGSLEHHHHHH |
| 64 | 21 | MDSHCRVRPAGPAVPADCDPPRITHAALAARLGDARLLTLYDQATWSEGPA<br>WWEAQRTLVWSDLVGRRVLGWREDGTVDVLLDATAFTNGNAVDAQQRLV<br>HCEHGRRAITRSDADGQAHLLVGRYAGKRLNSPNDLIVARDGAIWFTDPPFGL<br>RKPSQGCPADPELAHHSVYRLPPDGSPLQRMADLDHPNGLAFSPDEQTLYVSQ<br>TPEQGHGSVEITAFAWRDGALHDRRHFASVPDGLPDGFCVDRGGWLSSSGT<br>GVCVFDSDGQLLGHIPTPGTASNCTFDQAQQRLFITGGPCLWMLPLPGGSLEH<br>HHHHH |
| 65 | 22 | MKQFSAKYALILLATAGQALAASTQGISEDLYNRLVEMATISQAAYADLCNIP<br>STIIKGEKIYNAQTDINGWILRDDTSKEIITVFRGTGSDTNLQLDTNYTLTPFDTL<br>PQCNDCEVHGGYYIGWISVQDQVESLVKQQASQYPDYALTVTGHSLGASMA<br>ALTAAQLSATYDNVRLYTFGEPRSGNQAFASYMNDAFQVSSPETTQYFRVTH<br>SNDGIPNLPPADEGYAHGGVEYWSVDPYSAQNTFVCTGDEVQCCEAQGGQG<br>VNDAHTTYFGMTSGACTWGGSLEHHHHHH |
| 66 | 23 | MPSSISVLAAGILVPVLGAVAAKLPPTAQIIDQKSFNVLKDVPPPAVANDSLVF<br>TWPGVTEESLVEKPFHVYDEEFYDVIGKDPSLTLIATSDTDPIFHEAVVWYPPT<br>EEVFFVQNAGAPAAGTGLNKSSIIQKISLKEADEVRKGKKDEVKVTVVDSNPQ<br>VINPNGGTYYKGNIIFAGEGQGDDVPSALYLMNPLPPYNTTTLLNNYFGRQFN<br>SLNDVGINPRNGDLYFTDTLYGYLQDFRPVPGLRNQVYRYNFDTGAVTVVAD<br>DFTLPNGIGFGPDGKKVYVTDTGIALGFYGRNLSSPASVYSFDVNQDGTLQNR<br>KTFAYVASFIPDGVHTDSKGRVYAGCGDGVHVWNPSGKLIGKIYTGTVAANF<br>QFAGKGRMIITGQTKLFYVTLGASGPKLYDGGSLEHHHHHH |
| 67 | 24 | MRTLATVASQTDAWTGEGPVWCAARRCLYYVDLGDTRPGKLHVYHPERCVE<br>EIHDLPAMTKDFTQVTAVTVVQNEPHRLAVATEAGVFLYDCQSGDLRRLTGE<br>LQPELPKGSYRSNDGKCDPRGRFLIGTMLFSADAPSGGLFSVAGSTIQQLLTGV |

TABLE 10-continued

Amino acid sequences of enzymes tested in Example 1

| SEQ ID NO: | ID# | Sequence |
|---|---|---|
|  |  | TIGNGLAWSANGRTMYFIDSPLKRIDAFEYHLDAGTLGARRTAFDFADYFAQQ AGWEEAAPDGMTIDAEGLLWVAIYGGGAALRVDPAKEEVVCRVDCPAKYTT SVALGGPARDTLYITSFRRGDAGPDAGAVFQCRAPAPGPPPAEFRLGGSLEHH HHHH |
| 68 | 25 | MFKLLSKLLVYLTASIMAIASPLAFSVDSSGEYPTVSEIPVGEVRLYQIADGVW SHIATRSFDGAVYPSNGLIVRDGDELLLIDTAWGAKNTAALLAEIEKQIGLPVT RAVSTHFHDDRVGGVDVLRAAGVATYASPSTRRLAEVEGSEIPTHSLEGLSSS GDAVRFGPVELFYPGAAHSTDNLVVYVPSASVLYGGCAIYELSRTSAGNVAD ADLAEWPTSIERIQQHYPEAQFVIPGHGLPGGLDLLKHTTNVVKAHTNRSVVE GGSLEHHHHHH |
| 69 | 26 | MLKVISSLLVYMTASVMAVASPLAHSGEPSGEYPTVNEIPVGEVRLYQIADGV WSHIATQSFDGAVYPSNGLIVRDGDELLLIDTAWGAKNTAALLAEIEKQIGLPV TRAVSTHFHDDRVGGVDVLRAAGVATYASPSTRRLAEAEGNEIPTHSLEGLSS SGDAVRFGPVELFYPGAAHSTDNLVVYVPSANVLYGGCAVHELSRTSAGNVA DADLAEWPTSVERIQKHYPEAEVVIPGHGLPGGLDLLQHTANVVKAHKNRSV AEGGSLEHHHHHH |
| 70 | 27 | MVDGNYSVASNVMVPMRDGVRLAVDLYRPDADGPVPVLLVRNPYDKFDVF AWSTQSTNWLEFVRDGYAVVIQDTRGLFASEGEFVPHVDDEADAEDTLSWIL EQAWCDGNVGMFGVSYLGVTQWQAAVSGVGGLKAIAPSMASADLYRAPWY GPGGALSVEALLGWSALIGTGLITSRSDARPEDAADFVQLAAILNDVAGAASV TPLAEQPLLGRLIPWVIDQVVDHPDNDESWQSISLFERLGGLATPALITAGWYD GFVGESLRTFVAVKDNADARLVVGPWSHSNLTGRNADRKFGIAATYPIQEAT TMHKAFFDRHLRGETDALAGVPKVRLFVMGIDEWRDETDWPLPDTAYTPFYL GGSGAANTSTGGGTLSTSISGTESADTYLYDPADPVPSLGGTLLFHNGDNGPA DQRPIHDRDDVLCYSTEVLTDPVEVTGTVSARLFVSSSAVDTDFTAKLVDVFP DGRAIALCDGIVRMRYRETLVNPTLIEAGEIYEVAIDMLATSNVFLPGHRIMVQ VSSSNFPKYDRNSNTGGVIAREQLEEMCTAVNRIHRGPEHPSHIVLPIIKRGGSL EHHHHHH |
| 71 | 28 | MSFKPTISVHATPQELSAAGCRKIVEHEASGSQQWPLSIALAGGSTPKMTYARL HDEHLNLLREKRALRFFMGDERMVPADSTDSNYNMAREVLLHDIPDDLVPPF DTSAVTPSAEATSADAMRVAEAYGKQLASLLPLKSVGEAGPKVPVFDVVLLG LGSDGHTASIFPGSQAEKETDGKVVVSVGFPSETMKPKVWRVTLSPATIMQAR NVIVLATGAEKKWVVDGILADTAHKAPVARFLRGCEGNVSFLLDKEIAENLA KFGGSLEHHHHHH |
| 72 | 29 | MPYAAVNGTELHYRIDGERHGNAPWIVLSNSLGTDLSMWAPQVAALSKHFR VLRYDTRGHGHSEAPKGPYTIEQLTGDVLGLMDTLKIARANFCGLSMGGLTG VALAARHADRIERVALCNTAARIGSPEVWVPRAVKARTEGMHALADAVLPR WFTADYMEREPVVLAMIRDVFVHTDKEGYASNCEAIDAADLRPEAPGIKVPA LVISGTHDLAATPAQGRELAQAIAGARYVELDASHISNIERADAFTKTVVDFLT EQKGGSLEHHHHHH |
| 73 | 30 | MAQRVKITTTATPGEIELAFEDTGTGLPVLLVHGFPLDRTMWKAQREELCDEF RVIVPDLRGFGESQVIPGVATMEAMADDLAGLCNHLGLTGKIVLGGLSMGGY VAFAFARKYRDRLAGLILCDTRARPDSPEAKENRRRVAERVRREGPGFIAEEM IPRLCCESTFRNHPEVIEKIRQMILSAPPEGVAAAALGMAERPDSTDLLPALSCP TLVLVGQFDAISPPEEMEAMARTIPQSQFVVIPDAGHLPPMEQPERVTQAIREW LRKVHTEAGGSLEHHHHHH |
| 74 | 31 | MSERIVPSGDVELWSDDFGDPADPALLLVMGGNLSALGWPDEFARRLADGGL HVIRYDHRDTGRSTTRDFAAHPYGFGELAADAVAVLDGWGVDRAHVVGLSM GATITQVIALDHHDRLSSLTMLLGGGLDIDFDANIERVMRGEPTLDGLPGPQQP FLDALALMNQPAEGRAAEVAKRVSKWRILSGTGVPFDDAEYARWEERAIDHA GGVLAEPYAHYSLTLPPPSRAAELREVTVPTLVIQAEHDPIAPAPHGKHLAGLI PTARLAEIPGMGHALPSSVHGPLAEVILAHTRSAAGGSLEHHHHHH |
| 75 | 32 | MTVKKLYFIPAGRCMLDHSSVNSALTPGKLLNLPVWCYLLETEEGPILVDTGM PESAVNNEGLFNGTFVEGQILPKMTEEDRIVNILKRVGYEPDDLLYIISSHLHFD HAGGNGAFTNTPIIVQRTEYEAALHREEYMKECILPHLNYKIIEGDYEVVPGVQ LLYTPGHSPGHQSLFIETEQSGSVLLTIDASYTKENFEDEVPFAGFDPELALSSIK RLKEVVKKEKPIIFFGHDIEQEKSCRVFPEYIGGSLEHHHHHH |
| 76 | 33 | MLKTISGTLALSLIIAASVHQAQAATTYNAVVSKSSSDGKTFKTIADAIASAPA GSTPFVILIKNGVYNERLTITRNNLHLKGESRNGAVIAAATAAGTLKSDGSKW GTAGSSTITISAKDFSAQSLTIRNDFDFPANQAKSDSDSSKIKDTQAVALYVTKS GDRAYFKDVSLVGYQDTLYVSGGRSFFSDCRISGTVDFIFGDGTALFNNCDLV SRYRADVKSGNVSGYLTAPSTNINQKYGLVITNSRVIRESDSVPAKSYGLGRP WHPTTTFSDGRYADPNAIGQTVFLNTSMDNHIYGWDKMSGKDKNGNTIWFN PEDSRFFEYKSYGAGATVSKDRRQLTDAQAAEYTQSKVLGDWTPTLPGGSLE HHHHHH |

TABLE 10-continued

Amino acid sequences of enzymes tested in Example 1

| SEQ ID NO: | ID# | Sequence |
|---|---|---|
| 77 | 34 | MLDMPIDPVYYQLAEYFDSLPKFDQFSSAREYREAINRIYEERNRQLSQHERVE RVEDRTIKGRNGDIRVRVYQQKPDSPVLVYHGGGFVICSIESHDALCRRIARL SNSTVVSVDYRLAPEHKFPAAVYDCYDATKWVAENAEEELRIDPSKIFVGGDSA GGNLAAAVSIMARDSGEDFIKHQILIYPVVNFVAPTPSLLEFGEGLWILDQKIM SWFSEQYFSREEDKFNPLASVIFADLENLPPALIITAEYDPLRDEGEVFGQMLRR AGVEASIVRYRGVLHGFINYYPVLKAARDAINQIAALLVFDGGSLEHHHHHH |
| 78 | 35 | MTLDLQVQSFLAQGGNLNTLTGEEHGEAKAVFKVEDFYIPVKDGEIKLRVYTP NEKESLPVFVYLHGGGWVAGDIQAVDTLCQNIAHDAECIVVAVEYRLAPTHK FPVPLEDCYEATKWVAENSSMLNADKTKIAIGGDSAGGNIAAAVVIMAQKFN NLSLVAQVLVYPVVDLTLTFKAQSYRDNAEGYLLTTEGVFWATQMYLRDEID RYNVFASPSVNNELENLPPALIITAEYDPLRDDGAAYAKRLEAAGIPVEYKCYE GMVHGFFWMAGIMDKGLQARLQVSNYLKSVFVGKGGSLEHHHHHH |
| 79 | 36 | MPLDPVIQQVLDQLNRMPAPDYKHLSAQQFRSQQSLFPPVKKEPVAEVREFD MDLPGRTLKVRMYRPEGVEPPYPALVYHGGGWVVGDLETHDPVCRVLAKD GRAVVFSVDYRLAPEHKFPAAVEDAYDALQWIAERAADFHLDPARIAVGGDS AGGNLAAVTSILAKERGGPALAFQLLIYPSTGYDPAHPPASIEENAEGYLLTGG MMLWFRDQYLNSLEELTHPWFSPVLYPDLSGLPPAYIATAQYDPLRDVGKLY AEALNKAGVKVEIENFEDLIHGFAQFYSLSPGATKALVRIAEKLRDALAGGSLE HHHHHH |
| 80 | 37 | MPLDPEVRNFLQVYYKANIIDFTKYQFQEIRQKVNELLAKAVPKDPVGETRDM KIKLEDYELPIRIYSPIKRTNNGLVMHFHGGAWILGSIETEDAISRILSNSCECTVI SVDYRLAPEYKFPTAVYDCFNAIVWARDNAGELGIDKDKIATFGISAGGNLVA ATSLLARDNKLKLTAQVPVVPFVYLDLASKSMNRYRKGYFLDINLPVDYGVK MYIRDEKDLYNPLFSPLIAEDLSNLPQAIVVTAEYDPLRDQGEAYAYRLMESG VPTLSFRVNGNVHAFLGSPRTSRQVTVMIGALLKDIFKGSSLEHHHHHH |
| 81 | 38 | MMPLDPRIKELLESGFIVPIGKASVDEVRKIFRQLASAAPKVEVGKVEDIKIPGS EANINARVYLPKANGPYGVLIYLHGGGFVIGDVESYDPLCRAITNACNCVVVS VDYRLAPEYKFPSAVIDSFDATNWVYNNLDKFDGKMGVAIAGDSAGGNLAA VVALLSKGKLNLKYQILIYPAVGFDSVSRSMIEYSDGFFLTREHIEWFGSQYLR SPADLLLDFRFSPILAQDLSGLPPALIITAEYDPLRDQGEAYANRLLQAGVPVTSV RFNNVIHGFLSFFPLIEQGRDAISLIGSVLRRTFYDKSGGSLEHHHHHH |
| 82 | 39 | MIDPKIKKLLESTIQLPIGKASVEEIRSLFKQFSSLTPREEVGKIEDITIPGSETNIK ARVYYPKTQGPYGVLVYYHGGGFVLGDIESYDPLCRAITNSCQCVTISVDYRL APENKFPAAVVDSFDALKWVYNNSEKFNGKYGIAVGGDSAGGNLAAVTAILS KKENIKLKYQVLIYPAVSFDLITKSLYDNGEGFFLTREHIDWFGQQYLRSFADL LDFRFSPILADLNDLPPALIITAEHDPLRDQGEAYANKLLQSGVQVTSVRFNNVI HGFVSFFPFIEQGRDAIGLIGYVLRKVFYGKGGSLEHHHHHH |
| 83 | 40 | MTEPLIIEPSQPADSAVIWLHGLGADRFDFEPVARLLGQHLPSTRFILPQAPTRP VTFNMGHAMPSWYDILALDGSERAINPADLEASSETLIALINAQQQSGIDSKRI VLAGFSQGGAVVLHTALLRFDEKLAGVLALSTYAPTFNAETQFAESKQNLPVL CMHGSEDAVLPISMGRAVYDKLSEQGIKANWRDYPMGHEVRPEQLRDILDW LKNTLPSLPGGSLEHHHHHH |
| 84 | 41 | MDKPIILDPKQSADSAVIWLHGLGATKEDFLPVAQILQRDALPHTRFILPQAPV RPVTLNNGFPMPSWYDIIALTSPREIKLSELDESSQSIIALIEABIEKGIPLERIILA GFSQGGAVVLHTAFIAYPKNVGGVMALSTYSATFDEAITLDEKKKQIPTLHLH GSLDPVVKIELGRAAEQFLKAQGIDTRWHDYPMQHEVINDELQDIAKWLIERL GGGSLEHHHHHH |
| 85 | 42 | MSDTLILEPTHRADACVIWLHGLGADRYDFLPVAEALQDVLGTTRFVLPQAPT RAVTINGGWAMPSWYDILAMSPERAIDEAQLEASAQQVMALAQAQVDGGIEP RRIFLAGFSQGGAVVLHTAFLRWEDELGGVLALSTYGPTFTDGMTLPDAKRQ LPVLCLHGTLDDVVLPAMGRAAHDRLAAAGVPVGWRDYPMAHEVLPQQVR DIGAWLVERLHSGGSLEHHHHHH |
| 86 | 43 | MSQPLLLEPTQPADSCVIWLHGLGADRYDFEPVARMLQKVLPRTRFILPQAPT RPVTVFNGMPAPSWYDIKAMAPARAIDEAQLDASADAVIALIEGQLAEGIAQR RIVLAGFSQGGAVVLHTGYLRWPGELGGVMALSTYGPTFDDDLQLPEAKKQQ PALCLHGTYDDVVAPAMGRAAYDFLQRQGVAVQWRDYPMAHEVSNQEIADI AAWLRERLGGSLEHHHHHH |
| 87 | 44 | MSEPLILDAPNADACIIWLHGLGADRTDFKPVAEALQMVLPSTRFILPQAPSQA VTVNGGWVMPSWYDILAFSPARAIDEDQLNASADQVIALIDEQRAKGIAAERII LAGFSQGGAVVLHTAFRRYAQPLGGVLALSTYAPTFDDLALDERHKRIPVLHL HGSQDDVVDPALGRAAHDALQAQGVEVGWHDYPMGHEVSLEEIHDIGAWLR KRLGGSLEHHHHHH |
| 88 | 45 | MTDPLIIEPAQTADSCVIWLHGLGADRYDFQPVAEMLQQRLLHTRFVLPQAPT RAVTINGGWAMPSWYDIQAMSPARAIDQAQLEQSAQTVIELIEQQRDSGIDPR |

TABLE 10-continued

Amino acid sequences of enzymes tested in Example 1

| SEQ ID NO: | ID# | Sequence |
|---|---|---|
|  |  | RIFLAGFSQGGAVVYHTAFLRWAGPLGGVLALSTYAPTFGDDLKLSPLQAGLP VLCLHGSRDDVVPPAMGRAAHDCLQQNQVQTQWKEYPMAHEVQPTEIQDIG DWLASRLGGGSLEHHHHHH |
| 89 | 46 | MTEPLILQPAKPADACVIWLHGLGADRYDFMPVAEALQESLLTTRFVLPQAPT RPVTINGGYEMPSWYDIKAMSPARSISLEELEVSAKMVTDLIEAQKRTGIDASR IFLAGFSQGGAVVFHTAFINWQGPLGGVIALSTYAPTFGDELELSASQQRIPAL CLHGQYDDVVQNAMGRSAFEHLKSRGVTVTWQEYPMGHEVLPQEIHDIGAW LAARLGGGSLEHHHHHH |

Molecular Modeling and Design.

Designs were built using Compound D as the model's substrate. Compound D was selected to represent the diacylated anthocyanins we sought to transform to Compound I. A conformer library of 5,000 conformations was generated using Spartan (Spartan '14 Wavefunction, Inc. Irvine, Calif.). This library was docked into the active site of crystal structure model using RosettaDock (Meiler et al., "ROSETTALIGAND: Protein—small molecule docking with full side-chain flexibility," *Proteins: Structure, Function, and Bioinformatics.* 65(3):538-548, 2006). To ensure the docked interface were bound in a catalytically competent orientation for the esterase chemistry to occur, catalytic constraints were added to ensure that the catalytic residues (S114, D168, H199, L23, Q115) were within the appropriate distances and angles to one another and to the ester bond of the anthocyanin we aimed to cleave. Eight rounds of design were done, each running the modeling protocol 5,000 times. The top 20 designs from each round were examined in FoldIt and subsets of mutations were chosen for characterization based on the beneficial interactions being introduced.

Of the active enzymes, enzyme 46 of Tables 9 and 10 (referred to herein as 1AUR; corresponding to SEQ ID NO: 89) was amongst the most active enzymes that also had a previously determined crystal structure, making it the top lead from database mining efforts for further optimization. To enhance functionality, we docked Compound F into the crystal structure while employing catalytic constraints to ensure catalytically relevant orientations were modeled. A total of 3,000 models were generated from which the lowest energy was selected to run Rosetta Design simulations around, and the 15 lowest-energy designs were selected to examine manually using FoldIt (Kleffner et al., "Foldit Standalone: a video game-derived protein structure manipulation interface using Rosetta," *Bioinformatics.* 33(17): 2765-2767, 2017)). Given the native enzyme's specific activity toward fatty acid chains, we focused on adding polar residues to the active site to promote hydrogen bonding between the enzyme and the highly polar anthocyanins. Focus was placed on residues surrounding the active site, which occurs at the interface of the protein dimer. A total of 53 unique designed protein sequences were chosen over three rounds to characterize for degradation of di-acylated anthocyanins (Table 10). Upon completion of each round of design, residue sites that positively altered activity were targeted for further mutagenesis, with individual residues being replaced by amino acids with similar characteristics. Positive mutations were also combined to probe for combinatorial enhancement of activity.

Protein Purification and Enzymatic Assay of Esterases.

An *E. coli* codon optimized gene encoding each protein, i.e., one of the enzymes of Table 9, was purchased from Twist Biosciences and transferred into pET29b+ to encode a C-terminal hexahistidine tag (SEQ ID NO: 91). Mutants plasmids were produced by Kunkel mutagenesis (Kunkel et al., "Rapid and efficient site-specific mutagenesis without phenotypic selection," *Proceedings of the National Academy of Sciences.* 82(2):488-492, 1985). Plasmids were incorporated into *Escherichia coli* BL21(DE3) via electroporation. 500 mL cultures were grown in Terrific Broth at 37° C., induced with 1 mM isopropyl-β-D-1-thiogalactopyranoside (IPTG), and allowed to express at 18° C. for 24 hours. Proteins were purified with immobilized metal affinity chromatography and eluted in HEPES buffer pH 8.0 to 1 mg/mL. 90 μL of buffered enzyme was mixed with 10 μL red cabbage extract (RCE) suspended in 1% HCl (100 mg/mL). To detect the presence of activity, assays were allowed to run for 24 at room temperature, after which they were quenched with 5% HCl. Assays to determine the rate of reactions were conducted using an enzyme concentration of 0.5 mg/mL. Reaction products were analyzed by liquid chromatography (HPLC) on an Agilent 1100 Series. The column (Phenomenex pentafluorophenyl propyl 2.6 μm core, 100×4.6 mm) was held at room temperature. The mobile phase was a gradient mixture of solvent A (4.5% formic acid in Milli-Q water) and solvent B (acetonitrile) as follows: 100% A (0 min), 0% to 30% B (25 min), 30% to 95% B (1 min), 95% B (5 min), 95% to 0% B (1 min), 100% A (13 min). Products were monitored at 530 nm, the maximum absorbance of Compound I. The experiment was repeated for enzymes that demonstrated activity on RCE anthocyanins. For these enzymes, the reaction size was increased 5-fold, and a portion was withdrawn and quenched at timed intervals in order to evaluate the rate of the reactions.

Gram Scale Protein Production & Purification.

The M73H point-mutant was created from the 1AUR Wild type plasmid via Kunkel Mutagenesis. The sequence of the M73H point-mutant corresponds to the amino acid sequence of SEQ ID NO: 16 tagged with a hexahistidine tag of SEQ ID NO: 90 attached at the C-terminus of the protein. Then transformed into chemically competent *Escherichia coli* BLR cells and plated on agar (Fisher BP1423500) plates containing 50 μg/mL kanamycin (Fisher AC450810500). Single colonies were picked and used to inoculate 10 mL Terrific Broth (TB) (Fisher BP2468-2) in 50 mL Falcon tubes (Fisher 14-959-49A). These were incubated at 37° C. while shaking at 300 RPM for 12-16 hours. For long term storage of the inoculated cells, a glycerol stock was made with 500 μL of the cell culture and 500 μL of 50% autoclaved glycerol (Fisher G33-4) in Mili-Q water and stored in −80° C. freezer. To begin protein production, the starting culture consisted of a 50 mL Terrific Broth (TB) with 50 µg/mL kanamycin and 15 µg/mL tetracycline hydrochloride (Fisher 5834625GM) in a 250 mL Erlenmeyer baffled flask. This was inoculated with a swab of cells from the glycerol stock and shaken at 250 RPM at 37° C. After 14-16 hours, the starter culture was poured into a 1 L Erlenmeyer baffled flask containing 450 mL TB with 50 µg/mL kanamycin and 15 µg/mL tetracycline hydrochloride. These flasks were covered with breathable seals (Fisher 12-567-05) and shaken at 300 RPM, at 37° C. for 4-6 hours until the $OD_{600}$ reached 0.7-1.0. The 500 mL cultures were then cooled at 4° C. for 30 minutes, and enough isopropyl-β-D-1-thiogalactopyranoside (IPTG) (Fisher 420322-25GM) was added for a final concentration of 1 mM and shaken again at 300 RPM, at 18° C. for 24 hours to induce expression of the M73H mutant enzyme. After expression, the cultures were pelleted by being spun down for 10 minutes at 4700 RPM at 4° C. The supernatant was poured out and the pelleted cells were resuspended in 10 mL 1× phosphate buffered saline (PBS) buffer pH 7.4 (135 mM NaCl, 2.7 mM KCl, 4.3 mM $Na_2HPO_4$, and 1.4 mM $KH_2PO_4$) (diluted from pre-made 20×PBS buffer (VWR Int. 100218-160)) and stored in 50 mL falcon tubes at −20° C. For purification, the frozen cells containing enzyme were thawed on ice and brought up to a volume of 40 mL with 1×PBS buffer. Then sonicated at an amplitude of 50 with a process time of 3 minutes, with 30 seconds on and 30 seconds off. The lysed cells were spun down for 1 hour at 4700 RPM, at 4° C. The supernatant lysate is then collected and used for the reaction.

Gram Scale Peak B Enzyme Reaction & Product Validation.

To determine the yield of enzyme in the lysate, 500 µL of lysate was purified from every batch. A 1 mL column with 200 µL Cobalt beads (Fisher PI89966) was washed with 1 mL Wash buffer pH 7.4 (same as the 1×PBS buffer with 10 mM Imidazole (Fisher AC122020020) added). Then 500 µL of lysate was poured through the column, the His-tagged M73H mutant enzyme became immobilized on the beads via metal ion affinity chromatography and washed with 5 mL of Wash buffer. Enzyme was eluted with 250 µL Elution buffer pH 7.4 (same as the 1×PBS buffer with 200 mM Imidazole added) and protein yield was determined by A280 using a BioTek Epoch spectrophotometer.

To set up the reaction, the substrate, Red Cabbage (RC-B), was dissolved in 1×PBS buffer pH 7.4 at 50 mg/mL and brought up to pH 7.5 with 6M NaOH (Fisher S318-500) in a 1 L glass bottle. This was combined with an appropriate amount of lysate for a final ratio of 1 mg of enzyme for every 200 mg of RC-B substrate. For example, 150 mL of lysate at 1 mg/mL of enzyme would be combined with 30 g RC-B substrate dissolved in 600 mL of 1×PBS. The assay reaction proceeded for 4 days in a 1 L Nalgene Amber bottle (Thermo 967-10936-357), all while gently agitated on a rocker (Neta BMK-B3D1308). The reaction was then quenched by bring down the pH to 2.8 with 6M HCl (Fisher BP1756100) and then frozen at −20° C. To verify reaction completion, 500 µL of product was combined with 500 µL of Acetonitrile (Millipore Sigma 439134-4L) in a 2 mL centrifuge tube and spun down at 10,000 RPM for 10 minutes at 4° C. Then 100 µL of the supernatant was placed in a vial (Fisher 0339115) and run on a High-Performance Liquid Chromatography (HPLC) machine at a wavelength of 530 nm to check for reaction completion. The HPLC run method begins by injecting 2 µL of sample, then starts a flow rate of 0.5 mL/min consisting of 4.5% formic acid (Millipore Sigma 27001-500ML-R) in Mili-Q water. For the first 25 minutes, the flow of 4.5% formic acid was slowly decreased to 70%, while acetonitrile was slowly increased to 30% of the mobile phase. This continued until the acetonitrile and 4.5% formic acid reached 95% and 5% of the mobile phase, respectively, at 26 minutes. The mobile phase stayed constant until 31 minutes into the run. At 32 minutes, the acetonitrile decreased back down to 0%, while the 4.5% formic acid increased back up to being 100% of the mobile phase. This continued until the end of the run at 45 minutes. During the run, the column was at 20° C., and was a Phenomenex Kinetex PFP column, particle size of 2.6 µm, pore size of 100 Å, and the dimensions were 100×4.6 mm.

Figure 4A:
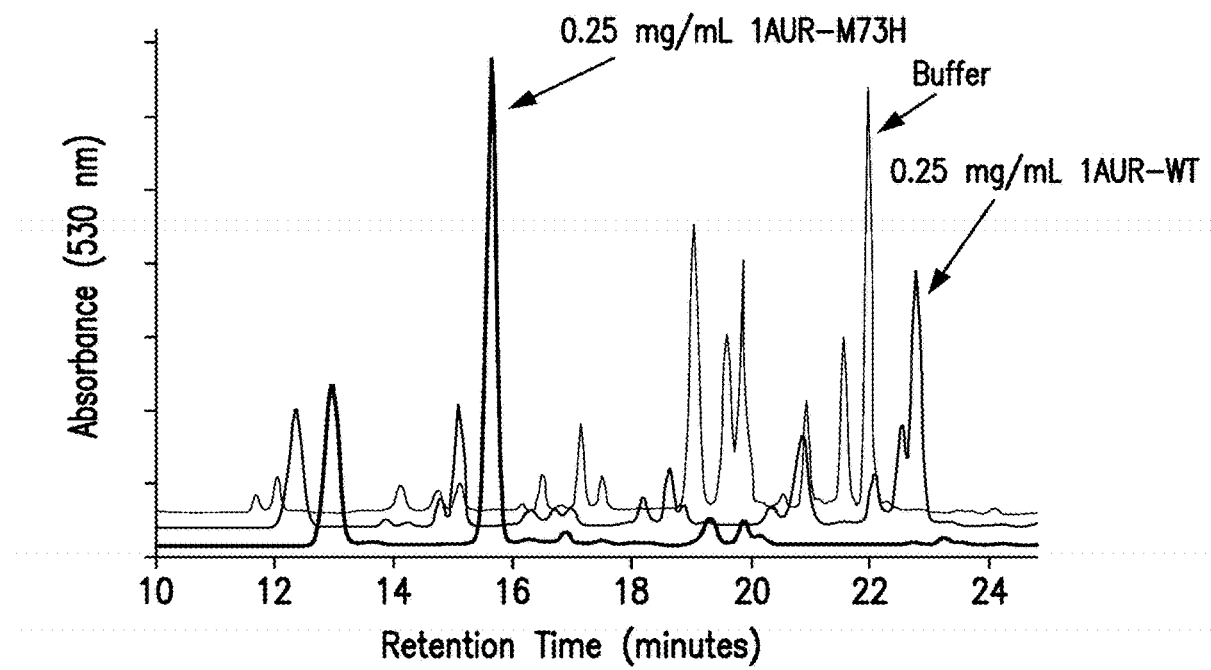
FIG. 4A provides a high performance liquid chromatography (HPLC) trace of red cabbage extract in buffer (red), incubated with 0.25 mg/mL 1AUR-WT (blue), and incubated with 0.25 mg/mL 1AUR-M73H (black) after 24 hours.
Figure 4B:
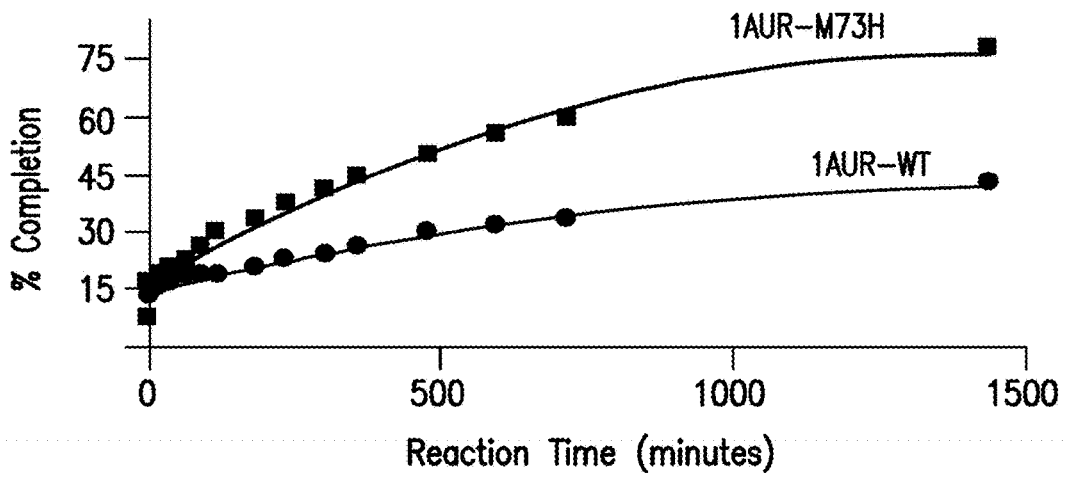
FIG. 4B provides a graph showing the completion of conversion to Compounds I and II over a 24 hour reaction with enzymes 1AUR-WT and 1AUR-M73H. Each data point of the 24 hour HPLC trace of FIG. 4A corresponds with a data point in FIG. 4B.

It was observed that the mutant with the best conversion rates of Compounds A-F to Compounds I and II was the M73H mutant of 1AUR, which yielded 84% more Compound I than the native enzyme over 24 hours (FIGS. 4A and 4B).

Example 2: Isolation of Compound I

The present Example provides for a protocol to isolate Compound I from a red cabbage juice and/or extract that has undergone enzymatic treatment described herein.

First, the enzymes were precipitated from the reaction mixture. Hydrochloric acid was added to the reaction mixture to adjust the pH to about 1.10, and the reaction mixture was left to sit in an ice bath for about 2 hours. The liquid was then transferred to centrifuge tubes and centrifuged at 3540 rcf for 5 minutes. After this time, the supernatant was decanted and subsequently vacuum filtered through a Buchner funnel and Whatman 1 filter paper.

The resulting material was then further purified by Solid Phase Extraction using a Phenomenex Strata C18 SPE cartridge. The cartridge was activated with 2 column volumes of 190 proof ethanol, followed by 2 column volumes of acidified water (0.01% HCl). The material was then loaded onto the cartridge. The SPE cartridge was washed with 2 column volumes of acidified water, then the anthocyanin compounds were eluted using acidified ethanol (0.01% HCl).

The ethanol was then removed from the solution containing the anthocyanins by placing the solution in a warm water bath at 34° C. with a steady stream of nitrogen gas passing over. For every 10 mL of ethanol evaporated, an equal volume of Milli-Q 18.2 MOhm deionized water was added to the sample.

Compound I was then purified by using reverse phase preparatory HPLC-DAD. The HPLC-DAD parameters were as follows: 250 mm L×50 mm D Phenomenex Luna C18 (2) preparatory LC column with 10 micron particle size and 100 Å pore size; mobile phases A: 5% acetic acid in deionized water and B: 5% acetic acid in 190 proof ethanol; flow rate of 60 mL/min; wavelength detection set to 280 nm and 520 nm. The gradient method used is: (1) B: 0%-12%, 0-30 min. (2) B: 12%-50%, 30-35 min. (3) B: 50% isocratic, 35-45 min. (4) B: 50%-0%, 45-46 min. Fractions were collected manually based on the elution of Compound I observed using visible signal, 520 nm.

Example 3: Lyophilization of Compound I

The present Example provides for procedures used to lyophilize Compound I.

Fractions comprising Compound I as isolated in Example 2 were collected. Ethanol was removed from the combined fraction using rotary evaporation, where the water bath was set to 37° C. and the pressure was 60 mbar. These conditions allowed for removal of ethanol, as well as some acetic acid and water.

The resulting aqueous sample was transferred to a polypropylene container and immersed in liquid nitrogen until fully frozen. The container was then placed into the lyophilizer with pressure set to 0.03 mbar and the condenser temperature set to −80° C.

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods or steps.

Patents, patent applications publications product descriptions, and protocols are cited throughout, the disclosures of which are incorporated herein by reference in their entireties for all purposes.

What is claimed is:

1. A method of producing Compound I:

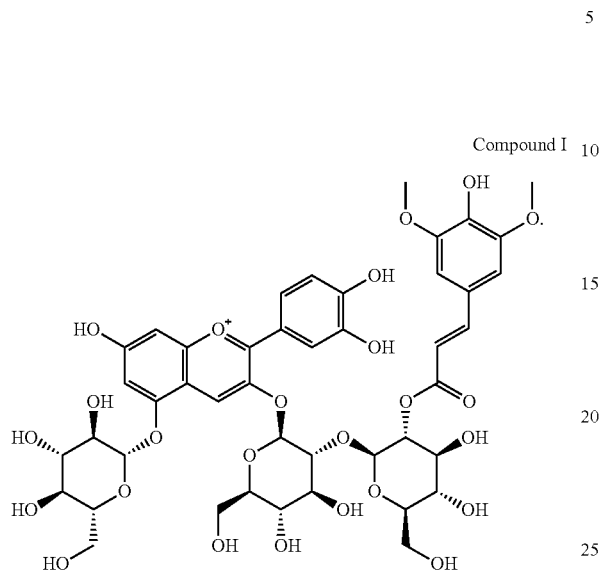

Compound I comprising contacting a fruit or vegetable juice or extract comprising a diacylated anthocyanin with a carboxylesterase, wherein the carboxylesterase selectively hydrolyzes the diacylated anthocyanin to produce Compound I.

2. The method of claim 1, wherein the carboxylesterase comprises the amino acid sequence of any one of SEQ ID NO: 1-43.

3. The method of claim 1, wherein the diacylated anthocyanin has the structure of Formula 1:

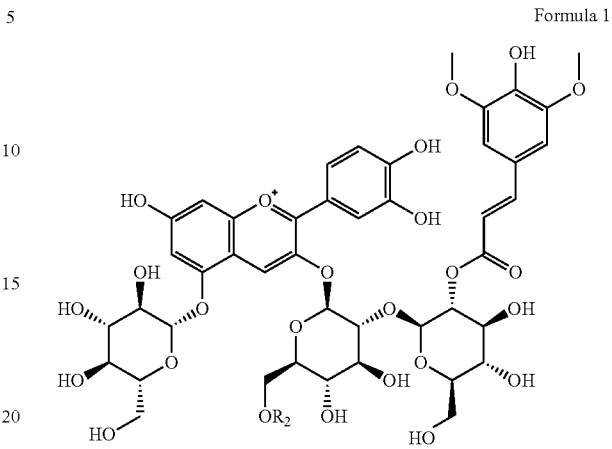

Formula 1 wherein $R_2$ is an acyl group.

4. The method of claim 3, wherein the acyl group of $R_2$ has the structure

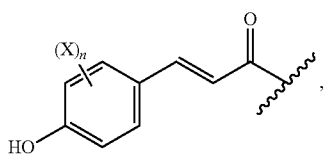

wherein X is a $C_{1-4}$ alkoxy group, and
n is an integer from 0-2.

5. The method of claim 1, wherein the fruit or vegetable juice or extract is a vegetable juice or extract.

6. The method of claim 1, wherein Compound I is present in an amount of from about 40% to about 100% by weight of a total anthocyanin content of the solution at least about 24 hours after the solution is contacted with the enzyme.

7. The method of claim 2, wherein the carboxylesterase comprises the amino acid sequence of any one of SEQ ID NO: 16-43.

8. The method of claim 7, wherein the carboxylesterase comprises the amino acid sequence of SEQ ID NO: 16.

9. The method of claim 5, wherein the vegetable juice or extract is red cabbage juice or extract.

* * * * *